US009724370B2

(12) United States Patent
Tseng et al.

(10) Patent No.: US 9,724,370 B2
(45) Date of Patent: *Aug. 8, 2017

(54) AMNIOTIC MEMBRANE PREPARATIONS AND PURIFIED COMPOSITIONS AND THERAPY FOR SCAR REVERSAL AND INHIBITION

(71) Applicant: TissueTech, Inc., Doral, FL (US)

(72) Inventors: Scheffer Tseng, Pinecrest, FL (US); Hua He, Miami, FL (US); Wei Li, Shenzhen (CN)

(73) Assignee: TISSUETECH, INC., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/848,148

(22) Filed: Sep. 8, 2015

(65) Prior Publication Data

US 2016/0129050 A1    May 12, 2016

Related U.S. Application Data

(63) Continuation of application No. 13/802,359, filed on Mar. 13, 2013, now Pat. No. 9,161,955, which is a continuation of application No. 13/453,765, filed on Apr. 23, 2012, now Pat. No. 8,440,235, which is a continuation of application No. 11/528,902, filed on Sep. 27, 2006, now Pat. No. 8,182,840.

(60) Provisional application No. 60/720,760, filed on Sep. 27, 2005.

(51) Int. Cl.

| | |
|---|---|
| *A61K 35/50* | (2015.01) |
| *A61K 9/00* | (2006.01) |
| *A61K 31/738* | (2006.01) |
| *A61L 15/40* | (2006.01) |
| *C07K 14/47* | (2006.01) |
| *A61K 38/17* | (2006.01) |
| *A61K 35/48* | (2015.01) |
| *A61K 38/39* | (2006.01) |
| *A61K 38/48* | (2006.01) |
| *C07K 14/78* | (2006.01) |
| *C07K 14/81* | (2006.01) |
| *A61K 9/06* | (2006.01) |
| *A61K 9/08* | (2006.01) |
| *A61L 15/44* | (2006.01) |

(52) U.S. Cl.
CPC ............ *A61K 35/50* (2013.01); *A61K 9/0014* (2013.01); *A61K 9/0048* (2013.01); *A61K 9/0053* (2013.01); *A61K 9/06* (2013.01); *A61K 9/08* (2013.01); *A61K 31/738* (2013.01); *A61K 35/48* (2013.01); *A61K 38/1709* (2013.01); *A61K 38/39* (2013.01); *A61K 38/4886* (2013.01); *A61L 15/40* (2013.01); *A61L 15/44* (2013.01); *C07K 14/4702* (2013.01); *C07K 14/4718* (2013.01); *C07K 14/78* (2013.01);
*C07K 14/8114* (2013.01); *A61L 2300/412* (2013.01); *A61L 2300/64* (2013.01)

(58) Field of Classification Search
CPC ........ A61K 35/50; A61K 9/08; A61K 31/738; A61K 9/0053; A61K 9/0048; A61K 9/0014; A61K 9/06; A61K 38/4886; A61K 38/39; A61K 38/1709; A61K 35/48; A61L 15/40; A61L 15/44; C07K 14/8114; C07K 14/78; C07K 14/4718; C07K 14/4702

See application file for complete search history.

(56) References Cited

U.S. PATENT DOCUMENTS

| | | | |
|---|---|---|---|
| 3,598,122 A | 8/1971 | Zaffaroni | |
| 3,598,123 A | 8/1971 | Zaffaroni | |
| 3,710,795 A | 1/1973 | Higuchi et al. | |
| 3,731,683 A | 5/1973 | Zaffaroni | |
| 3,742,951 A | 7/1973 | Zaffaroni | |
| 3,814,097 A | 6/1974 | Ganderton et al. | |
| 3,909,816 A | 9/1975 | Teeters | |
| 3,921,636 A | 11/1975 | Zaffaroni | |
| 3,972,995 A | 8/1976 | Tsuk et al. | |
| 3,993,072 A | 11/1976 | Zaffaroni | |

(Continued)

FOREIGN PATENT DOCUMENTS

| | | |
|---|---|---|
| CN | 1193515 A | 9/1998 |
| CN | 1203794 A | 1/1999 |

(Continued)

OTHER PUBLICATIONS

Yoshida. Placenta Power: For Health and Beauty—A useful guide for those seeking placenta-based remedies. Aug. 2001. p. 1-41; downloaded from http://www.melsmon.co.jp/img/commom/PlacentaPowerp002-121_04-09-08.pdf.*

Sur et al. Anti-inflammatory and anti-platelet aggregation activity of human placental extract. Acta Pharmacol Sin Feb. 2003; 24(2):187-192.*

Drug Administration and Drug Effectiveness. Chapter 2. Drug Delivery—Engineering Principles for Drug Therapy. W. M. Saltzman. Oxford Press. 2001. p. 9-19.*

(Continued)

*Primary Examiner* — Taeyoon Kim
(74) *Attorney, Agent, or Firm* — Wilson Sonsini Goodrich & Rosati

(57) ABSTRACT

Compositions having a combination of specific biological components have been found to exert a number of useful effects in mammalian cells, including modulating TGF β signaling, apoptosis, and proliferation of mammalian cells, as well as decreasing inflammation in mice. These components can be obtained commercially, or can be prepared from biological tissues such as placental tissues. Placental amniotic membrane (AM) preparations described herein include AM pieces, AM extracts, AM jelly, AM stroma, and mixtures of these compositions with additional components. The compositions can be used to treat various diseases, such as wound healing, inflammation and angiogenesis-related diseases.

11 Claims, 29 Drawing Sheets

(56) References Cited

U.S. PATENT DOCUMENTS

| | | | |
|---|---|---|---|
| 3,993,073 A | 11/1976 | Zaffaroni |
| 3,996,934 A | 12/1976 | Zaffaroni |
| 4,031,894 A | 6/1977 | Urquhart et al. |
| 4,060,084 A | 11/1977 | Chandrasekaran et al. |
| 4,069,307 A | 1/1978 | Higuchi et al. |
| 4,077,407 A | 3/1978 | Theeuwes et al. |
| 4,100,022 A | 7/1978 | Ogasa et al. |
| 4,120,649 A | 10/1978 | Schechter |
| 4,201,211 A | 5/1980 | Chandrasekaran et al. |
| 4,230,105 A | 10/1980 | Harwood |
| 4,292,299 A | 9/1981 | Suzuki et al. |
| 4,292,303 A | 9/1981 | Keith et al. |
| 4,305,502 A | 12/1981 | Gregory et al. |
| 4,327,725 A | 5/1982 | Cortese et al. |
| 4,347,841 A | 9/1982 | Benyo et al. |
| 4,361,552 A | 11/1982 | Baur, Jr. |
| 4,405,616 A | 9/1983 | Rajadhyaksha |
| 4,476,116 A | 10/1984 | Anik |
| 4,599,084 A | 7/1986 | Nashef |
| 4,599,226 A | 7/1986 | Fox, Jr. et al. |
| 4,624,848 A | 11/1986 | Lee |
| 4,801,586 A | 1/1989 | Minaskanian et al. |
| 4,829,000 A | 5/1989 | Kleinman et al. |
| 4,861,764 A | 8/1989 | Samour et al. |
| 4,871,549 A | 10/1989 | Ueda et al. |
| 4,886,783 A | 12/1989 | Minaskanian et al. |
| 4,968,509 A | 11/1990 | Radebaugh et al. |
| 4,983,396 A | 1/1991 | Bodor et al. |
| 4,997,425 A | 3/1991 | Shioya et al. |
| 5,002,071 A | 3/1991 | Harrell |
| 5,011,692 A | 4/1991 | Fujioka et al. |
| 5,017,381 A | 5/1991 | Maruyama et al. |
| 5,033,252 A | 7/1991 | Carter |
| 5,052,558 A | 10/1991 | Carter |
| 5,093,487 A | 3/1992 | Brown et al. |
| 5,116,817 A | 5/1992 | Anik |
| 5,118,845 A | 6/1992 | Peck et al. |
| 5,135,915 A | 8/1992 | Czarniecki et al. |
| 5,192,744 A | 3/1993 | Bouck et al. |
| 5,196,410 A | 3/1993 | Francoeur et al. |
| 5,229,135 A | 7/1993 | Philippon et al. |
| 5,260,068 A | 11/1993 | Chen |
| 5,260,069 A | 11/1993 | Chen |
| 5,294,446 A | 3/1994 | Schlameus et al. |
| 5,323,907 A | 6/1994 | Kalvelage |
| 5,336,168 A | 8/1994 | Sibalis |
| 5,352,668 A | 10/1994 | Burgeson et al. |
| 5,436,135 A | 7/1995 | Tayot et al. |
| 5,437,287 A | 8/1995 | Phillips et al. |
| 5,456,923 A | 10/1995 | Nakamichi et al. |
| 5,461,140 A | 10/1995 | Heller et al. |
| 5,508,040 A | 4/1996 | Chen |
| 5,516,527 A | 5/1996 | Curatolo |
| 5,554,593 A | 9/1996 | Nakaya et al. |
| 5,567,441 A | 10/1996 | Chen |
| 5,622,721 A | 4/1997 | Dansereau et al. |
| 5,665,378 A | 9/1997 | Davis et al. |
| 5,686,105 A | 11/1997 | Kelm et al. |
| 5,700,410 A | 12/1997 | Nakamichi et al. |
| 5,837,280 A | 11/1998 | Kenealy et al. |
| 5,837,284 A | 11/1998 | Mehta et al. |
| 5,840,329 A | 11/1998 | Bai |
| 5,869,090 A | 2/1999 | Rosenbaum |
| 5,932,545 A | 8/1999 | Henkin et al. |
| 5,948,766 A | 9/1999 | Milan et al. |
| 5,977,175 A | 11/1999 | Lin |
| 6,152,142 A | 11/2000 | Tseng |
| 6,203,755 B1 | 3/2001 | Odland |
| 6,326,019 B1 | 12/2001 | Tseng |
| 6,391,452 B1 | 5/2002 | Antonsen et al. |
| 6,465,014 B1 | 10/2002 | Moroni et al. |
| 6,521,179 B1 | 2/2003 | Girardot et al. |
| 6,573,249 B2 | 6/2003 | Lezdey et al. |
| 6,632,648 B1 | 10/2003 | Kampinga et al. |
| 6,923,983 B2 | 8/2005 | Morgan et al. |
| 6,929,801 B2 | 8/2005 | Klose et al. |
| 6,932,983 B1 | 8/2005 | Straub et al. |
| 6,946,144 B1 | 9/2005 | Jordan |
| 7,476,221 B2 | 1/2009 | Sun et al. |
| 7,494,802 B2 | 2/2009 | Tseng et al. |
| 8,093,365 B2 | 1/2012 | Wisniewski et al. |
| 8,105,634 B2 | 1/2012 | Liu et al. |
| 8,153,162 B2 | 4/2012 | Tseng et al. |
| 8,182,840 B2 | 5/2012 | Tseng et al. |
| 8,182,841 B2 | 5/2012 | Tseng et al. |
| 8,187,639 B2 | 5/2012 | Tseng et al. |
| 8,323,701 B2 | 12/2012 | Daniel et al. |
| 8,372,438 B2 | 2/2013 | Daniel et al. |
| 8,420,126 B2 | 4/2013 | Tseng et al. |
| 8,440,235 B2 | 5/2013 | Tseng et al. |
| 8,455,009 B2 | 6/2013 | Tseng et al. |
| 8,460,714 B2 | 6/2013 | Tseng et al. |
| 8,486,374 B2 | 7/2013 | Tamarkin et al. |
| 8,741,265 B2 | 6/2014 | Tamarkin et al. |
| 2001/0041684 A1 | 11/2001 | Lezdey et al. |
| 2002/0192272 A1 | 12/2002 | Popp |
| 2003/0064093 A1* | 4/2003 | Jordan ............... A61K 9/0014 424/449 |
| 2003/0180181 A1 | 9/2003 | Greib et al. |
| 2004/0048796 A1 | 3/2004 | Hariri et al. |
| 2004/0057938 A1 | 3/2004 | Ghinelli |
| 2004/0126323 A1 | 7/2004 | Shevchuk et al. |
| 2005/0064391 A1 | 3/2005 | Segal et al. |
| 2006/0153928 A1 | 7/2006 | Kinoshita et al. |
| 2007/0202189 A1 | 8/2007 | Ahlfors et al. |
| 2008/0046095 A1 | 2/2008 | Daniel |
| 2008/0069895 A1 | 3/2008 | Liu et al. |
| 2008/0102135 A1 | 5/2008 | Ollivier |
| 2008/0131522 A1 | 6/2008 | Liu et al. |
| 2008/0181935 A1 | 7/2008 | Bhatia et al. |
| 2008/0181967 A1 | 7/2008 | Liu et al. |
| 2008/0193554 A1 | 8/2008 | Dua et al. |
| 2008/0241211 A1 | 10/2008 | Han et al. |
| 2009/0130162 A2 | 5/2009 | Pathak et al. |
| 2009/0226499 A1 | 9/2009 | Wisniewski et al. |
| 2010/0047214 A1 | 2/2010 | Abramson et al. |
| 2010/0104539 A1 | 4/2010 | Daniel et al. |
| 2010/0272782 A1 | 10/2010 | Owens et al. |
| 2011/0212158 A1 | 9/2011 | Tom et al. |
| 2011/0256202 A1 | 10/2011 | Tom et al. |
| 2012/0083445 A1 | 4/2012 | Tseng et al. |
| 2012/0141595 A1 | 6/2012 | Tseng et al. |
| 2012/0189583 A1 | 7/2012 | Liu et al. |
| 2013/0156863 A1 | 6/2013 | Tseng et al. |
| 2013/0195992 A1 | 8/2013 | Tseng et al. |
| 2013/0195993 A1 | 8/2013 | Tseng et al. |
| 2013/0195994 A1 | 8/2013 | Tseng et al. |
| 2013/0280344 A1 | 10/2013 | Tseng et al. |
| 2013/0344163 A1 | 12/2013 | Tseng et al. |
| 2014/0067058 A1 | 3/2014 | Koob et al. |
| 2014/0112998 A1 | 4/2014 | Tseng et al. |
| 2014/0147511 A1 | 5/2014 | Tseng et al. |
| 2015/0166624 A1 | 6/2015 | Tseng |
| 2015/0342998 A1 | 12/2015 | Tseng et al. |
| 2016/0120912 A1 | 5/2016 | Tseng |

FOREIGN PATENT DOCUMENTS

| | | |
|---|---|---|
| EP | 0669138 A2 | 8/1995 |
| EP | 1604695 A1 | 12/2005 |
| JP | 74043153 B | 11/1974 |
| JP | H01256967 A | 10/1989 |
| KR | 20010098716 A | 11/2001 |
| WO | WO-9837903 A1 | 9/1998 |
| WO | WO-0180844 A2 | 11/2001 |
| WO | WO-03077794 A2 | 9/2003 |
| WO | WO-03097809 A2 | 11/2003 |
| WO | WO-2004026244 A2 | 4/2004 |
| WO | WO-2004060388 A1 | 7/2004 |
| WO | WO-2005060988 A1 | 7/2005 |
| WO | WO-2006094247 A2 | 9/2006 |
| WO | WO-2007038686 A2 | 4/2007 |
| WO | WO-2008060377 A2 | 5/2008 |
| WO | WO-2011031489 A2 | 3/2011 |

(56) References Cited

FOREIGN PATENT DOCUMENTS

| | | |
|---|---|---|
| WO | WO-2012149486 A1 | 11/2012 |
| WO | WO-2012170905 A1 | 12/2012 |
| WO | WO-2013032938 A1 | 3/2013 |
| WO | WO-2013103413 A1 | 7/2013 |
| WO | WO-2014011813 A1 | 1/2014 |
| WO | WO-2015187812 A1 | 12/2015 |
| WO | WO-2016010984 A2 | 1/2016 |
| WO | WO-2016073667 A1 | 5/2016 |
| WO | WO-2016187555 A1 | 11/2016 |

OTHER PUBLICATIONS

Wu et al. Wound healing effects of porcine placental extracts on rats with thermal injury. British Journal of Dermatology 2003; 148: 236-245.*
Adatia et al. Correlation Between Corneal Sensitivity, Subjective Dry Eye Symptoms and Corneal Staining in Sjogren's Syndrome. Can I Ophthalmol 39:767-771 (2004).
Brophy. Gas Chromatographic Quality Control for Oil of Melaleuca Terpinen-4-ol Type (Australian Tea Tree). J. Agric. Food Chem. 37:1330-1335 (1989).
Budavari et al. The Merck Index, Thirteenth Edition, Merck & Co., Inc., Rahway, NJ (4 pgs) (2001).
Co-pending U.S. Appl. No. 15/051,477, filed Feb. 23, 2016.
Co-pending U.S. Appl. No. 15/160,487, filed May 20, 2016.
Co-pending U.S. Appl. No. 15/214,706, filed Jul. 20, 2016.
Co-pending U.S. Appl. No. 15/215,228, filed Jul. 20, 2016.
CTFA (Cosmetic, Toiletry, and Fragrance Association) International Cosmetic Ingredient Dictionary and Handbook, 10th Ed. (2004) (abstract only).
He et al. Inhibition of Proliferation and Epithelial Mesenchymal Transition via Wnt and TGF-β Signaling Pathway in an in vitro Cell Culture Based-PVR Model by HC-HA/PTX3 Purified from Amniotic Membrane. The Association for Research in Vision and Ophthalmology (ARVO) 2016 on May 1-May 5 (Washington State Convention Center, Seattle, Washington) Abstract No. 5384-B005 (2 pgs).
Inactive Ingredient Guide, U.S. Food and Drug Administration (FDA) Center for Drug Evaluation and Research (CDER) Office of Management, http://www.accessdata.fda.gov/scripts/cder/iig/index.cfm (8 pgs.) (2012).
Kuriyan et al. A potential novel therapy for PVR: HC-HA/PTX3, an active matrix component of amniotic membrane, inhibits proliferation of rabbit RPE cells and is non-toxic intravitreally. The Association for Research in Vision and Ophthalmology (ARVO) 2015 meeting on May 3-May 7 (Colorado Convention Center Denver, CO) Abstract No. 1126-B029 (2 pgs).
Kuriyan et al. HC-HA/PTX3, an active matrix component of amniotic membrane, inhibits proliferation and epithelial mesenchymal transition of RPE cells: a potential novel therapy for PVR. The Association for Research in Vision and Ophthalmology (ARVO) 2015 meeting on May 3-May 7 (Colorado Convention Center Denver, CO) Abstract No. 2287-B0192 (2 pgs).
Merck Manuals Online Medical Library, Age-Related Macular Degeneration (ARMD), originally printed Aug. 13, 2008/reprinted 2016 from http://www.merck.com/mmpe/print/sec09/ch106/ch106b.html (9 pgs.).
Mondello et al. In vivo activity of terpenin-4-ol, the main bioactive component of Melaleuca alternifolia Cheel (tea tree) oil against azole-susceptible and -resistant human pathogenic Candida species. BMC Infectious Diseases 6:158 (2006).
PCT/US2015/033955 International Search Report and Written Opinion dated Aug. 19, 2015.
PCT/US2015/059142 International Search Report and Written Opinion dated Jan. 19, 2016.
PCT/US2015/040315 International Search Report and Written Opinion dated Dec. 29, 2015.
Rennie et al. Applications of Amniotic Membrane and Fluid in Stem Cell Biology and Regenerative Medicine. Stem Cells International (ID 721538):1-13 (2012).
Trommer et al. Overcoming the Stratum Corneum: Modulation of Skin Penetration. A review. Skin Pharmacol Physiol 19(2):106-121 (2006).
U.S. Appl. No. 13/704,231 Office Action dated Aug. 2, 2016.
Co-pending U.S. Appl. No. 15/195,189, filed Jun. 28, 2016.
Moalli et al. Pathogen Recognition by the Long Pentraxin PTX3. Journal of Biomedicine and Biotechnology 2011:Article ID 830421 (15 pgs.) (2011).
U.S. Appl. No. 14/004,992 Office Action dated Jun. 6, 2016.
U.S. Appl. No. 14/125,301 Office Action dated May 10, 2016.
U.S. Appl. No. 14/414,047 Office Action dated Jul. 8, 2016.
U.S. Appl. No. 14/886,946 Office Action dated Apr. 18, 2016.
Azuara-Blanco et al. Amniotic Membrane Transplantation for Ocular Surface Reconstruction. Invest. Ophthalmol. Vis. Sci. 39(4):5428 (1998).
Azuara-Blanco et al. Amniotic Membrane Transplantation for Ocular Surface Reconstruction. Br. J. Ophthalmol. 83(4):399-402 (1999).
Badawy et al. Evaluation of Tissue Healing and Adhesion Formation After an Intraabdominal Amniotic Membrane Graft in the Rat. J. Reproductive Med. 34:198 (1989).
Bae et al. Characterization of the Promoter Region of the Human Transforming Growth Factor-β Type II Receptor Gene,. J. Biol. Chem. 270(49):29460-29468 (1995).
Barton et al. Amniotic membrane transplantation in glaucoma surgery. Invest Ophthalmol Vis Sci 1997; 38:S473.
Bhutto et al. Localization of Collagen XVIII and the Endostatin Portion of Collagen XVIII in Ages Human Control Eyes and Eyes with Age-Related Macular Degeneration. Invest. Ophthalmol. Vis. Sci. 45(5):1544-1552 (2004).
Border et al. Transforming Growth Factor-β in Disease: The Dark Side of Tissue Repair. J. Clin. Invest. 90:1-7 (1992).
Budenz et al. Amniotic Membrane Transplantation for Repair of Leaking Glaucoma Filtering Blebs. Am. J. Ophthalmol. 130:580-588 (2000).
Chen et al. Amniotic Membrane Transplantation for Severe Neurotrophic Corneal Ulcers. Br. J. Ophthalmol. 84:826-833 (2000).
Chen et al. Recombinant Adenovirus Coexpressing Covalent Peptide/MHC Class II Complex and B7-1: In Vitro and In Vivo Activation of Myelin Basic Protein-Specific T Cells, J. Immunol. 167:1297-1305 (2001).
Chen et al. Functions of hyaluronan in wound repair, Wound Rep. Reg. 7:79-89 (1999).
Cho et al. Conjunctival Epithelial Cells Cultured on Human Amniotic Membrane Fail to Transdifferentiate into Corneal Epithelial-type Cells. Cornea, 18:216-224 (1999).
Cho et al. Conjunctival Epithelial Cells Cultured on Human Amniotic Membrane Do Not Transdifferentiate into Corneal Epithelial Type Cells. Invest. Ophthalmol. Vis. Sci. 39(4):S428 (1998).
Choi et al. Effect of the Application of Human Amniotic Membrane on Rabbit Corneal wound Healing After Excimer Laser Photorefractive Keratectomy. Cornea, 17:389-395 (1998).
Colon et al. Transfer of Inter-α-inhibitor Heavy Chains to Hyaluronan by Surface-linked Hyaluronan-TSG-6 Complexes. J. Biol. Chem. 2009. 284:2320-2331.
Cooke et al. Comparison of cryopreserved amniotic membrane and umbilical cord tissue with dehydrated amniotic membrane/chorion tissue. J Wound Care 23(10):465-474 (2014).
Co-pending U.S. Appl. No. 14/848,143, filed Sep. 8, 2015.
Co-pending U.S. Appl. No. 14/848,153, filed Sep. 8, 2015.
Day et al. Hyaluronan cross-linking: a protective mechanism in inflammation? Trends in Immunology 26(12):637-643 (2005).
Derotth. Plastic Repair of Conjunctival Defects with Fetal Membranes. Archives of Ophthalmology 23:522-525 (1940).
Derynk et al. TGF-β receptor signaling, Biochem. Biophys. Acta. 1333:F105-F150 (1997).
Diaz-Prado et al. Potential use of the human amniotic membrane as a scaffold in human articular cartilage repair. Cell Tissue Bank 11:183-195 (2010).
Dua et al. Amniotic Membrane Transplantation. Br. J. Ophthalmol. 83:748-752 (1999).

(56) References Cited

OTHER PUBLICATIONS

Fortunato et al. Interleukin-10 and transforming growth factor-β inhibit amniochorion tumor necrosis factor-α production by contrasting mechanisms of action: Therapeutic implications in prematurity. Am. J. Obstet. Gynecol. 177(4):803-809 (1997).
Fortunato et al. Interleukin-10 inhibition of interleukin-6 in human amniochorionic membrane: Transcriptional regulation. Am. J. Obstet. Gynecol. 175:1057-1065 (1996).
Fortunato et al. The effect of transforming growth factor and interleukin-10 on interleukin-8 release by human amniochorion may regulate histologic chorioamnionitis. Am. J. Obstet. Gynecol. 179(3):794-799 (1998).
Franch et al. Human Amniotic Membrane Transplantation. Invest. Ophthalmol. Vis. Sci. 39(4):S90 (1998).
Fries et al. Intera-a-inhibitor, hyaluronan and inflammation, Acta Biochim. Polonica 50(3):735-742 (2003).
Fujishima et al. Trabeculectomy With the Use of Amniotic Membrane for Uncontrolled Glaucoma, Ophthalmic. Surg. Lasers 29:428-431 (1998).
Fukuda et al. Differential Distribution of Subchains of the Basement Membrane Components Type IV Collagen and Laminin Among the Amniotic Membrane, Cornea, and Conjunctiva. Cornea 18:73-79 (1999).
Gabbiani. The myofibroblast in wound healing and fibrocontractive diseases. J. Pathol. 200:500-503 (2003).
Grande. Role of Transforming Growth Factor-β in Tissue Injury and Repair. Proc. Soc. Exp. Biol. Med. 214:27-40 (1997).
Guo. Carbopol® Polymers for Pharmaceutical Drug Delivery Applications. Drug Delivery Technology 3(6):1-4 (2003).
Hales et al. TGF-β-1 induces lens cells to accumulate α-smooth muscle actin, a marker for subcapsular cataracts. Curr. Eye Res. 13:885-890 (1994).
Hanada et al. Regulation of cytokine signaling and inflammation. Cytokine & Growth Factor Reviews 13(4-5):413-421 (2002).
Hao et al. Identification of Antiangiogenic and Antiinflammatory Proteins in Human Amniotic Membrane. Cornea 19(3):348-352 (2000).
Hatano et al. Transplantation of amniotic membrane and limbal autograft in the treatment of recurrent pterygium. Clinical Ophthalmology 50(6):1101-1104 (1996) (English Abstract).
He et al. A simplified system for generating recombinant adenoviruses, PNAS USA 95:2509-2514 (1998).
He et al. Biochemical Characterization and Function of Complexes formed by Hyaluronan and the Heavy Chains of Inter-α-inhibitor (HC-HA) Purified from Extracts of Human Amniotic Membrane. J. Biol. Chem., 284 (30):20136-20146 (Jul. 24, 2009).
Heiligenhaus et al. Improvement of HSV-1 Necrotizing Keratitis with Amniotic Membrane Transplantation, Invest. Ophthalmol. Vis. Sci. 42(9):1969-1974 (2001).
Hilmy et al. Physical and chemical properties of freeze-dried amnio-chorion membranes sterilized by y irradiation. Atom Indonesia 13(2):1-3 (1987) Abstract only.
Hori. Amniotic Membrane Transplantation and Immune Reaction. Folia Ophthalmologica Japonica 56(9):722-727 (2005) (English Abstract).
Howes et al. Receptor for Advanced Glycation End Products and Age-Related Macular Degeneration. Invest. Ophthalmol. Vis. Sci. 45(10):3713-3720 (2004).
Jadin et al. Characterization of a Novel Recombinant Hyaluronan Binding Protein for Tissue Hyaluronan Detection. Journal of Histochemistry & Cytochemistry 62(9):672-683 (2014).
Jester et al. Corneal Stromal Wound Healing in Refractive Surgery: the Role of Myofibroblasts. Prog. Retin. Eye Res. 18(3):311-356 (1999).
Jester et al. Induction of α-Smooth Muscle Actin Expression and Myofibroblast Transformation in Cultured Cornea Keratocytes. Cornea 15(5):505-516 (1996).
Keelan et al. Activin A Exerts both Pro- and -Anti-inflammatory Effects on Human Term Gestational Tissues. Placenta 31:38-43 (2000).

Kim et al. Amniotic Membrane Patching Promotes Healing and Inhibits Protease Activity on Wound Healing Following Acute Corneal Alkali Burns. Exp. Eye Res. 70:329-337 (1998).
Kim et al. Clinical Uses of Human Amniotic Membrane for Ocular Surface Diseases. In: Advances in Corneal Research, Lass, J.H. ed. (NY: Plenum Press), pp. 117-134 (1997).
Kim et al. Temporary Amniotic Membrane Graft Promotes Healing and Inhibits Protease Activity in Corneal Wound Induced by Alkali Burn in Rabbits. Invest. Ophthalmol. Vis. Sci. 39(4):590 (1998).
Kim et al. The Effects on Inhibition of Corneal Neovascularization After Human Amniotic Membrane Transplantation in Severely Damaged Rabbit Corneas. Korean J. Ophthalmol. 9:32-46 (1995).
Kim et al. Transplantation of Preserved Human Amniotic Membrane for Surface Reconstruction in Severely Damaged Rabbit Corneas. Cornea 15:473-84 (1995).
Klen. Influence of Ionizing Sterilization on the Permeability of Human Chorio-Amniotic, Dermo-Epidermal and Fascial Grafts. Res. Exp. Med. 167(1):15-21 (1976).
Koizumi et al. Amniotic Membrane as a Substrate for Cultivating Limbal Corneal Epithelial Cells for Autologous Transplantation in Rabbits. Cornea, 19:65-71 (2000).
Koizumi et al. Cultivation of Corneal Epithelial Cells on Intact and Denuded Human Amniotic Membrane. Invest. Ophthalmol. Vis. Sci. 41:2506-2513 (2000).
Koizumi et al. Growth Factor mRNA and Protein in Preserved Human Amniotic Membrane. Curr. Eye Res. 20:173-177 (2000).
Kopp et al. Abrogation of Transforming Growth Factor-beta Signaling by SMAD7 Inhibits Collagen Gel Contraction of Human Dermal Fibroblasts. J. Biol. Chem. 280(22):21570-21576 (2005).
Kruse et al. Cryoperserved Human Amniotic Membrane for Ocular Surface Reconstruction. Graefe's Arch. Clin. Exp. Ophthalmol. 238:68-75 (2000).
Kruse et al. Multilayer Amniotic Membrane Transplantation for Reconstruction of Deep Corneal Ulcers. Ophthalmology 106:1504-1511 (1999).
Lawrence, D.A., Transforming Growth Factor-β: a general review. Eur. Cytokine Netw. 7:363-374 (1996).
Lee et al Amniotic Membrane Transplantation for Persistent Epithelial Defects with Ulceration. Am. J. Ophthalmol. 123:303-312 (1997).
Lee et al. An Agarose Gel Electrophoretic Method for Analysis of Hyaluronan Molecular Weight Distribution. Anal. Biochem. 219:278-287 (1994).
Lee et al. Suppression of TGF-β signaling in both normal conjunctival fibroblasts and pterygial body fibroblasts by amniotic membrane. Curr. Eye Res. 20(4):325-334 (2000).
Li et al. An Experimental Study of the Effects of Human Amniotic Membrane on Human Retinal Pigment Epithelial Cell Proliferation in vitro. Acta Acadamiae Medicinae Militaris Tertia, 2003. 25(5):407-409 (with English Abstract).
Lieberman et al. Pharmaceutical Dosage Forms. 2 Ed. 1:209-214 (1990).
Liu et al. Biocompatibility and stability of disulfide-crosslinked hyaluronan films. Biomaterials 26(23):4737-4746 (2005).
Liu et al. E-cadherin engagement stimulates proliferation via Rac1. Journal of Cell Biology, 2006, 173(3):431-441.
Logan et al. Decorin Attenuates Gliotic Scar Formation in the Rat Cerebral Hemisphere. Exp. Neurol. 159:504-510 (1999).
Ma et al. Amniotic Membrane Graft for Primary Pterygium: Comparison with Conjunctival Autograft and Topical Mitomycin C Treatment. Br. J. Ophthalmol. 84:973-978 (2000).
Marek et al. TGF-β- (transforming growth factor-β) in chronic inflammatory conditions-a new diagnostic and prognostic marker? Med. Sci. Monitl 8(7):RA145-RA151 (2002).
Massague et al. Controlling TGF-β signaling. Genes and Development 14:627-644 (2000).
Meller et al. Amniotic Membrane Transplantation for Acute Chemical or Thermal Burns. Ophthalmology. 107:980-990 (2000).
Meller et al. Amniotic Membrane Transplantation for Symptomatic Conjunctivochalasis Refractory to Medical Treatments. Cornea 19:796-803 (2000).

(56) References Cited

OTHER PUBLICATIONS

Meller et al. In Vitro Conjunctival Epithelial Differentiation on Preserved Human Amniotic Membrane. Invest. Ophthalmol. Vis. Sci. 39(4):S428 (1998).
Meller et al. Conjunctival Epithelial Cell Differentiation on Amniotic Membrane. Invest. Ophthalmol. Vis. Sci. 40:878-886 (1999).
Milner et al. TSG-6: a multifunctional protein associated with inflammation, J. Cell Sci. 116(10):1863-1873 (2003).
Moller-Pedersen et al. Neutralizing antibody to TGF-β modulates stromal fibrosis but not regression of photoablative effect following PRK, Curr. Eye Res. 17:736-747 (1998).
Monteleone et al. SMAD7 in TGF-b-mediated negative regulation of gut inflammation. Trends in Immunology 25(10):513-517 (2004).
Mukhopadhyay et al. Two distinct populations of tumor necrosis factor-stimulated gene-6 protein in the extracellular matrix of expanded mouse cumulus cell-oocyte complexes. Archives of Biochemistry and Biophysics 394(2):173-181 (2001).
Na et al. Analysis of Human Amniotic Membrane Components as Proteinase Inhibitors for Development of Therapeutic Agent of Recalcitrant Keratitis. Invest. Ophthalmol. Vis. Sci. 39(4):S90 (1998).
Na et al. Analysis of Human Amniotic Membrane Components as Proteinase Inhibitors for Development of Therapeutic Agent for Recalcitrant Keratitis. Trophoblast Res. 13:453-466 (1999).
Nakao et al. SMAD7: a new key player in TGF-b-associated disease. Trends in Molecular Medicine 8(8):361-363 (2002).
Neumann et al. High molecular weight hyaluronic acid inhibits advanced glycation endproduct-induced NF-kB activation and cytokine expression. FEBS Ltrs. 453:283-287(1999).
Ochsner et al. Decreased expression of tumor necrosis factor-alpha-stimulated gene 6 in cumulus cells of the cyclooxygenase2 and EP2 null mice. Endocrinology 144: 1008-1019 (2003).
Oikawa et al. Inhibition of Angiogenesis by 15-Deoxyspergualin. J. Antibiotics 44(9):1033-1035 (1991).
Park et al. Modulation of Acute Inflammation and Keratocyte Death by Suturing, Blood and Amniotic Membrane in PRK. Invest. Ophthalmol. Vis. Sci. 41:2906-2914 (2000).
Park et al. Temperature Cooling Reduces Keratocyte Death in Excimer Laser Ablated Corneal and Skin Wounds. Invest. Ophthalmol. Vis. Sci. 39(4):S449 (1998).
PCT/US1998/03665 International Search Report mailed Jun. 23, 1998.
PCT/US2006/37906 International Preliminary Report on Patentability mailed Apr. 1, 2008.
PCT/US2006/37906 International Search Report and Written Opinion mailed Jul. 11, 2007.
PCT/US2010/032452 International Preliminary Report on Patentability and Written Opinion mailed Oct. 25, 2011.
PCT/US2010/032452 International Search Report mailed Dec. 27, 2010.
PCT/US2010/46675 International Preliminary Report on Patentability mailed Feb. 28, 2012.
PCT/US2010/46675 International Search Report and Written Opinion mailed May 30, 2011.
PCT/US2011/042679 International Preliminary Report on Patentability mailed Jan. 8, 2013.
PCT/US2011/042679 International Search Report and Written Opinion mailed Mar. 9, 2012.
PCT/US2012/035678 International Preliminary Report on Patentability mailed Oct. 29, 2013.
PCT/US2012/035678 International Search Report and Written Opinion mailed Oct. 1, 2012.
PCT/US2012/041685 International Preliminary Report on Patentability mailed Dec. 10, 2013.
PCT/US2012/041685 International Search Report and Written Opinion mailed Aug. 14, 2012.
PCT/US2013/049983 International Preliminary Report on Patentability dated Jan. 22, 2015.
PCT/US2013/049983 International Search Report and Written Opinion dated Nov. 29, 2013.
Petraglia et al. Inhibin and Activin in Human Fetal Membranes: Evidence of a Local Effect on Prostaglandin Release. J. Clin. Endocrinol. Metab. 77(2):542-548 (1993).
Pires et al. Amniotic Membrane Transplantation for Symptomatic Bullous Keratopathy. Arch. Ophthalmol. 117(10):1291-1297 (1999).
Pires et al. Amniotic Membrane Transplantation or Limbal Conjunctival Autograft for Limbal Stem Cell Deficiency Induced by 5-fluorouracil in Glaucoma Surgeries. Cornea 19:284-287 (2000).
Prabhasawat et al. Comparison of Conjunctival Autografts, Amniotic Membrane Grafts, and Primary Closure for Pterygium Excision. Ophthalmology 104:974-985 (1997).
Prabhasawat et al. Impression Cytology Study of Epithelial Phenotype of Ocular Surfaces Reconstructed by Preserved Human Amniotic Membrane. Arch Ophthalmol. 115:1360-1367 (Nov. 1997).
Riley et al. Production of inhibin forms by the fetal membranes, decidua, placenta and fetus at parturition. Hum. Reprod. 15:578-583 (2000).
Rodriguez-Ares et al. Repair of Scleral Perforation with Preserved Scleral and Amniotic Membrane in Marfan's Syndrome. Ophthalmic Surg. Lasers 30(6):485-487 (1999).
Romero et al. The natural interleukin-1 receptor antagonist in the fetal, maternal, and amniotic fluid compartments: The effect of gestational age, fetal gender, and intrauterine infection. Am. J. Obstet. Gynecol. 171:912-921 (1994).
Ronnov-Jessen et al. Induction of α-Smooth Muscle Actin by Transforming Growth Factor-β1 in Quiescent Human Breast Gland Fibroblasts. Lab. Invest. 68:696-707 (1993).
Rovere et al. The long pentraxin PTX3 binds to apoptotic cells and regulates their clearance by antigen-presenting dendritic cells. Blood 96(13):4300-4306 (2000).
Rugg et al, Characterization of complexes formed between TSG-6 and inter-alpha-inhibitor that act as intermediates in the covalent transfer of heavy chains onto hyaluronan. J Biol Chem 280(27):25674-25686 (2005).
Sakurai et al. Characterization of the Role of PTX2 in Enhancing the Anti-angiogenci Action of HC.HA Purified From the Chorion. Arvo Annual Meeting Abstract Search and Program Planner. 2011:4881 (May 2011).
Sanggaard et al, The transfer of heavy chains from bikunin proteins to hyaluronan requires both TSG-6 and HC2. J Biol Chem 283(27)1 8530-18537 (2008).
Sato et al. Role of Growth Factors for Ocular Surface Reconstruction After Amniotic Membrane Transplantation. Invest. Ophthalmol. Vis. Sci. 39(4):S428 (1998).
Serini et al. The Fibronectin Domain ED-A Is Crucial for Myofibroblastic Phenotype Induction by Transforming Growth Factor-β1. J. Cell. Biol. 142:873-881 (1998).
Shah et al. Control of scarring in adult wounds by neutralising antibody to transforming growth factor β Lancet 339:213-214 (1992).
Shimazaki et al. Amniotic Membrane Transplantation for Ocular Surface Reconstruction in Patients with Chemical and Thermal Burns. Ophthalmology. 104(12):2068-2076 (1997).
Shimazaki et al. Transplantation of Amniotic Membrane and Limbal Autograft for Patients with Recurrent Pterygium Associated with Symblepharon. Br. J. Ophthalmol. 82(3):235-240 (1998).
Singh et al. Encyclopedia of Pharmaceutical Technology 2nd Ed. pp. 751-753 (2002).
Solomon et al. Suppression of Interleukin 1a and interleukin 1b in human limbal epithelial cells cultured on the amniotic membrane stromal matrix. Br. J. Ophthalmol 85:444-449 (2001).
Sorsby Amniotic Membrane Grafts in Burns. In: Modern Trends in Ophthalmology. Sorsby, A. ed. (NY: Paul B. Hoeber, Inc.), pp. 504-510 (1947).
Sorsby et al. Amniotic Membrane Grafts in Caustic Burns of the Eye (Burns of the Second Degree. Br. J. Ophthalmology 30:337-345 (1946).
Sorsby et al. Further Experience with Amniotic Membrane Grafts in Caustic Burns of the Eye. Br. J. Ophthalmology 31:409-18 (1947).
Tan et al. Structural and Biological Comparison of Cryopreserved and Fresh Amniotic membrane Tissues. Journal Biomaterial and Tissue Engineering 4:379-388 (2014).

(56) References Cited

OTHER PUBLICATIONS

Taylor et al. Rate of Re-epithelialization Following Amniotic Membrane Transplantation. Invest. Ophthalmol. Vis. Sci. 39(4):S1038 (1998).
Travis et al. Hyaluronan Enhances Contraction of Collagen by Smooth Muscle BCells and Adventitial Fibroblasts Role of CD44 and Implications for Constrictive Remodeling, Cir. Res. 88:77-83 (2001).
Trelford. The Amnion in Surgery, Past and Present. Am J. Obstet. Gynecol 134:833 (1979).
Tsai. Corneal Surfaces Reconstruction by Amniotic Membrane with Cultivated Autologous Limbo-Corneal Epithelium. Invest. Ophthalmol. Vis. Sci. 39(4):S429 (1998).
Tsai et al. Reconstruction of Damaged Corneas by Transplantation of Autologous Limbal Epithelial cells. New Eng. J. Med., 343(2): 86-93 (2000).
Tseng et al. Down-regulation of TGF-.beta.1, .beta.2, .beta.3 and TGF-.beta. Receptor II Expression in Human Corneal Fibroblasts by Amniotic Membrane. Invest. Ophthalmol. Vis. Sci. 39(4):5428 (1998).
Tseng et al. Amniotic Membrane Transplantation with or without Limbal Transplantation for Corneal Surface Reconstruction in Patients with Limbal Stem Cell Deficiency. Arch Ophthalmol. 124(6):765-774 (Apr. 1998).
Tseng et al. Amniotic Membrane Transplantation for Conjunctival Surface Reconstruction. Am. J. Ophthalmol. 124:765-774 (Dec. 1997).
Tseng et al. How Does Amniotic Membrane Work? Ocular Surface J. 2(3):177-187 (2004).
Tseng et al. Suppression of Transforming Growth Factor-Beta Isoforms, TGF-βReceptor Type II, and Myofibroblast Differentiation in Cultured Human Corneal and Limbal Fibroblasts by Amniotic Membrane Matrix. J. Cell Physiol., 179:325-335 (1999).
Tsubota et al. Surgical Reconstruction of the Ocular Surface in Advanced Ocular Cicatricial Pemphigoid and Stevens-Johnson Syndrome. Am J. Ophthalmology 122:38-52 (1996).
U.S. Appl. No. 09/027,109 Office Action mailed Dec. 7, 1999.
U.S. Appl. No. 09/027,109 Office Action mailed Jun. 5, 2000.
U.S. Appl. No. 11/528,902 Office Action mailed Apr. 2, 2009.
U.S. Appl. No. 11/528,902 Office Action mailed Dec. 16, 2009.
U.S. Appl. No. 11/528,902 Office Action mailed Jan. 27, 2011.
U.S. Appl. No. 11/528,902 Office Action mailed Sep. 8, 2010.
U.S. Appl. No. 11/528,980 Office Action mailed Aug. 11, 2009.
U.S. Appl. No. 11/528,980 Office Action mailed Jan. 10, 2011.
U.S. Appl. No. 11/528,980 Office Action mailed Nov. 13, 2008.
U.S. Appl. No. 11/528,980 Office Action mailed Oct. 15, 2010.
U.S. Appl. No. 11/529,658 Office Action mailed Apr. 3, 2009.
U.S. Appl. No. 11/529,658 Office Action mailed Dec. 16, 2009.
U.S. Appl. No. 11/529,658 Office Action mailed Jan. 27, 2011.
U.S. Appl. No. 11/529,658 Office Action mailed Sep. 3, 2010.
U.S. Appl. No. 11/535,924 Office Action mailed Dec. 16, 2009.
U.S. Appl. No. 11/535,924 Office Action mailed Jan. 31, 2011.
U.S. Appl. No. 11/535,924 Office Action mailed Mar. 31, 2009.
U.S. Appl. No. 11/535,924 Office Action mailed Sep. 8, 2010.
U.S. Appl. No. 13/262,725 Office Action dated Feb. 25, 2015.
U.S. Appl. No. 13/262,725 Office Action mailed Jul. 17, 2014.
U.S. Appl. No. 13/322,896 Office Action dated Jul. 6, 2015.
U.S. Appl. No. 13/322,896 Office Action mailed Oct. 22, 2014.
U.S. Appl. No. 13/453,840 Office Action mailed Aug. 21, 2012.
U.S. Appl. No. 13/704,231 Office Action dated Jun. 4, 2015.
U.S. Appl. No. 13/796,761 Office Action dated Dec. 9, 2014.
U.S. Appl. No. 13/802,204 Office Action dated Aug. 7, 2015.
U.S. Appl. No. 13/802,204 Office Action dated Feb. 26, 2015.
U.S. Appl. No. 13/802,264 Office Action dated Jul. 16, 2015.
U.S. Appl. No. 13/802,264 Office Action mailed Nov. 28, 2014.
U.S. Appl. No. 13/802,359 Office Action dated Dec. 10, 2014.
U.S. Appl. No. 13/802,447 Office Action dated Dec. 15, 2014.
Verbeek et al. Induction of alpha-smooth muscle actin expression in cultured human brain pericytes by transforming growth factor-beta 1. Am. J. Pathol. 144:372-382 (1994).

Wang et al. Corneal Haze is Reduced by Amniotic Membrane Matrix in Excimer Laser Photoablation in Rabbits. Invest Ophthalmol Vis Sci 38:S405 (1997).
Yamaguchi et al. Negative regulation of transforming growth factor-β by the proteoglycan decorin. Nature 346(6281):281-284 (1990).
Yokomori et al. Advantages and Pitfalls of Amnion Inversion Repair for the Treatment of Large Unruptured Omphalocele: Results of 22 Cases. Journal of Pediatric Surgery 23:882-884.
Co-pending U.S. Appl. No. 14/869,609, filed Sep. 29, 2015.
Co-pending U.S. Appl. No. 14/880,135, filed Oct. 9, 2015.
Co-pending U.S. Appl. No. 14/886,946, filed Oct. 19, 2015.
Co-pending U.S. Appl. No. 14/996,051, filed Jan. 14, 2016.
U.S. Appl. No. 13/322,896 Office Action dated Jan. 20, 2016.
U.S. Appl. No. 13/704,231 Office Action dated Feb. 11, 2016.
U.S. Appl. No. 13/802,204 Office Action dated Jan. 22, 2016.
U.S. Appl. No. 14/004,992 Office Action dated Nov. 23, 2015.
Ahmed et al. Expression and localization of alphavbeta6 integrin in extraplacental fetal membranes: possible role in human parturition. Mol Hum Reprod 10(3):173-179 (2004).
Co-pending U.S. Appl. No. 15/348,736, filed Nov. 10, 2016.
He et al. Role of Hyaluronan, Inter-Alpha-Trypsin Inhibitor, and TSG-6 Complex in Amniotic Membrane in Inhibiting TFG-Beta Transcription. ARVO Annual Meeting Abstract. Investigative Ophthalmology & Visual Science 47:599 (May 2006).
Kuznetsova et al. The N-terminal module of thrombospondin-1 interacts with the link domain of TSG-6 and enhances its covalent association with the heavy chains of inter-alpha-trypsin inhibitor. J Biol Chem 280:30899-30908 (2005).
Lee et al. Adhesion between Amniotic Membrane and Retinal Tissue and Inhibition of Amniotic Membrane on Cell Transformation. J Korean Ophthalmol Soc. 44(2):459-471 (2003) (Abstract Only).
PCT/US2016/033558 International Search Report and Written Opinion dated Oct. 25, 2016.
Temma et al. Effects of 4-hydroxy-2-nonenal, a marker of oxidative stress, on the cyclooxygenase-2 of human placenta in chorioamnionitis. Mol Hum Reprod 10(3):167-171 (2004).
U.S. Appl. No. 13/322,896 Office Action dated Oct. 4, 2016.
U.S. Appl. No. 13/704,231 Office Action dated Jan. 19, 2017.
U.S. Appl. No. 13/802,204 Office Action dated Oct. 4, 2016.
U.S. Appl. No. 14/125,301 Office Action dated Aug. 19, 2016.
U.S. Appl. No. 14/240,712 Office Action dated Nov. 28, 2016.
U.S. Appl. No. 14/729,489 Office Action dated Dec. 7, 2016.
U.S. Appl. No. 14/848,143 Office Action dated Oct. 20, 2016.
U.S. Appl. No. 14/848,153 Office Action dated Oct. 25, 2016.
U.S. Appl. No. 14/869,609 Office Action dated Oct. 17, 2016.
U.S. Appl. No. 14/880,135 Office Action dated Dec. 23, 2016.
U.S. Appl. No. 14/886,946 Office Action dated Oct. 5, 2016.
U.S. Appl. No. 15/348,736 Office Action dated Jan. 23, 2017.
Wu et al. Wound healing effects of porcine placental extracts on rats with thermal injury. Br J Dermatol 148(2):236-245 (2003).
Zhang et al. Constitutive Expression of Pentraxin 3 (PTX3) Protein by Human Amniotic Membrane Cells Leads to Formation of the Heavy Chain (HC)-Hyaluronan (HA)-PTX3 Complex. J Biol Chem 289(19):13531-13542 (2014).
English Translation of JP74043153B (App. S45-107284) (9 pgs.) (Pub. Nov. 19, 1974).
Relucenti et al. Cumulus oophorus extracellular matrix in the human oocyte: a role for adhesive proteins. Ital J Anat Embryol 110(2 Supp 1):219-224 (2005).
Salustri et al. PTX3 plays a key role in the organization of th ecumulus oophorus extracellular matrix and in in vivo fertilization. Development 131:1577-1586 (2004).
U.S. Appl. No. 14/414,047 Office Action dated Feb. 13, 2017.
Wisniewski et al. Cytokine-induced gene expression at the crossroads of innate immunity, inflammation and fertility: TSG-6 and PTX3/TSG-14. Cytokine Growth Factor Rev 15(2-3):129-146 (2004).
Co-pending U.S. Appl. No. 15/588,331, filed May 5, 2017.

(56) References Cited

OTHER PUBLICATIONS

Hirashima et al. Inter-alpha-trypsin inhibitor is concentrated in the pericellular environment of mouse granulosa cells through hyaluronan-binding. Eur J Obstet Gynecol Reprod Biol. 73 :79-84 (1997).
Kobayashi et al. Identification of structural domains in inter-alpha-trypsin inhibitor involved in calcium oxalate crystallization. Kidney Int 53:1727-1735 (1998).
Sun et al. Link protein as an enhancer of cumulus cell-oocyte complex expansion. Mol Reprod Dev 63:223-231 (2002).
U.S. Appl. No. 14/848,153 Office Action dated Apr. 21, 2017.
U.S. Appl. No. 14/869,609 Office Action dated Jun. 2, 2017.
U.S. Appl. No. 14/886,946 Office Action dated May 19, 2017.

\* cited by examiner

P Value Comparison on Two Sides

|  | PL | FRO/P | FRO/F | FRE/P | FRE/F |
|---|---|---|---|---|---|
| PL | X | x | x | x | x |
| FRO/P | 0.007692 | x | x | x | x |
| FRO/F | 0.007268 | 0.30195 | x | x | x |
| FRE/P | 0.012165 | 0.024442 | 0.2375045 | x | x |
| FRE/F | 0.500177 | 0.115462 | 0.1283315 | 0.1481262 | x |

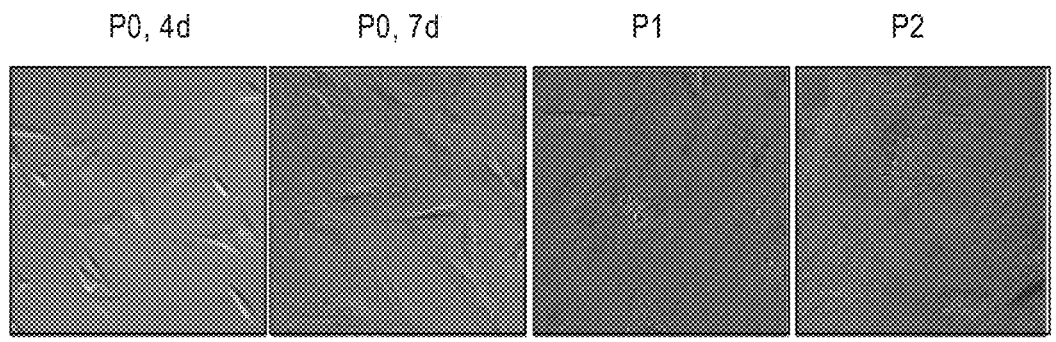
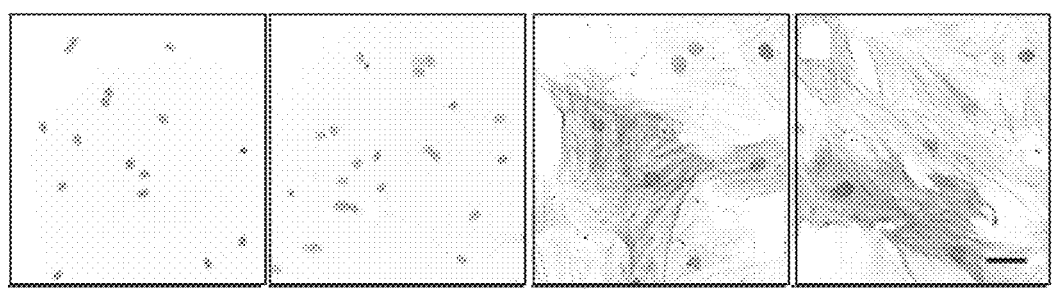
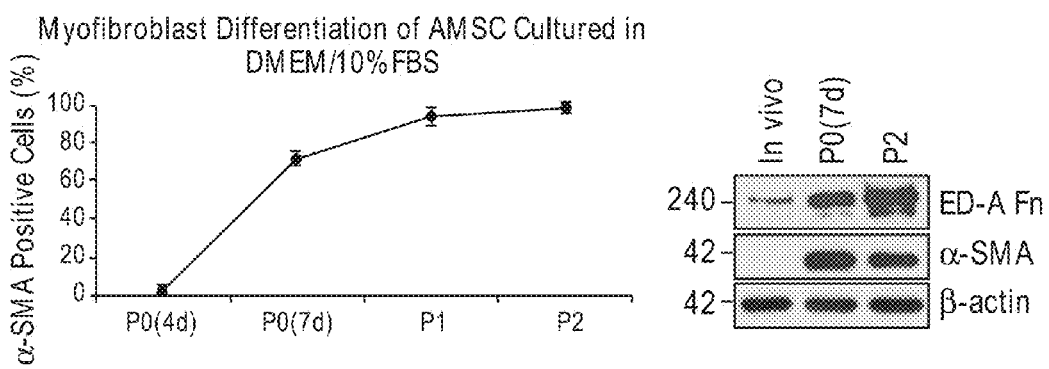
FIG. 22A  FIG. 22B  FIG. 22C  FIG. 22D
FIG. 22E  FIG. 22F  FIG. 22G  FIG. 22H
FIG. 22I  FIG. 22J

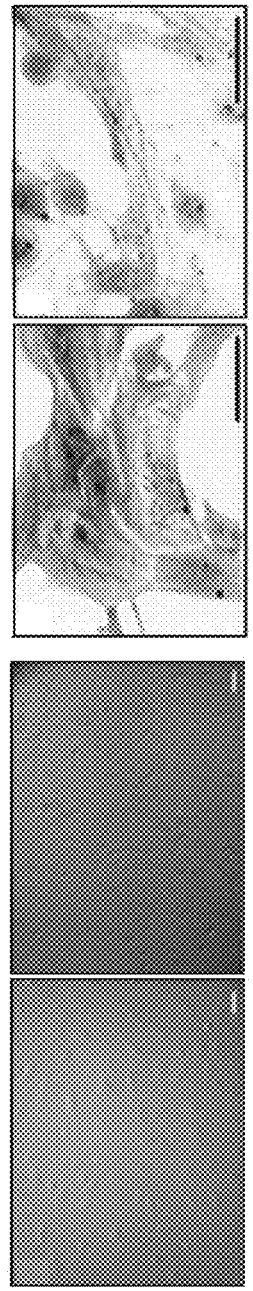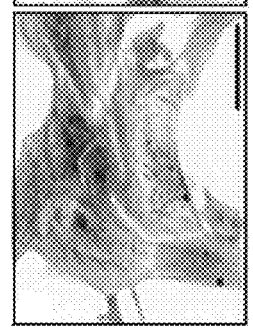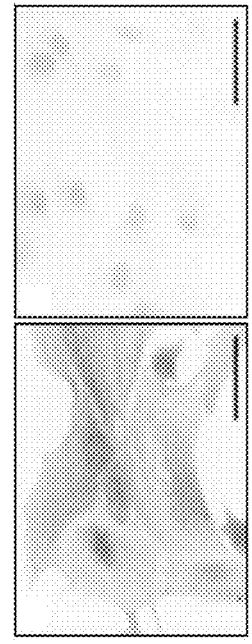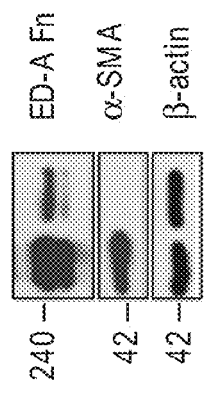

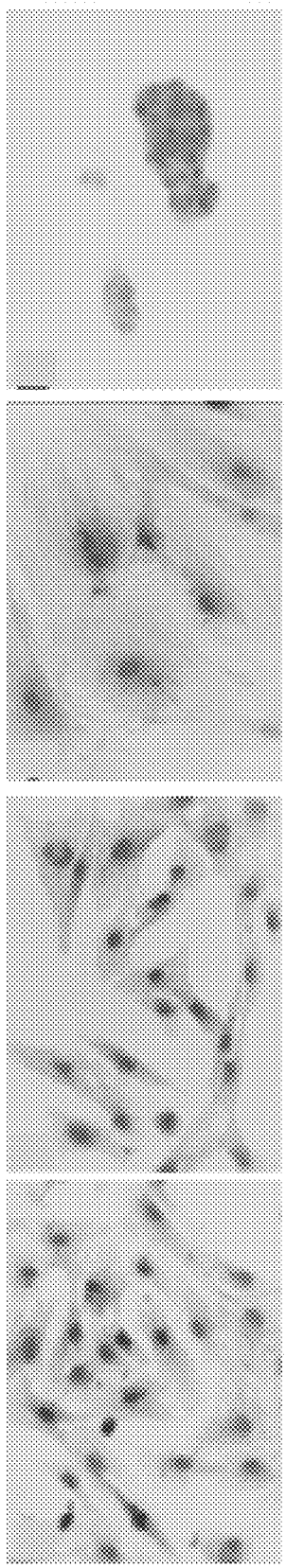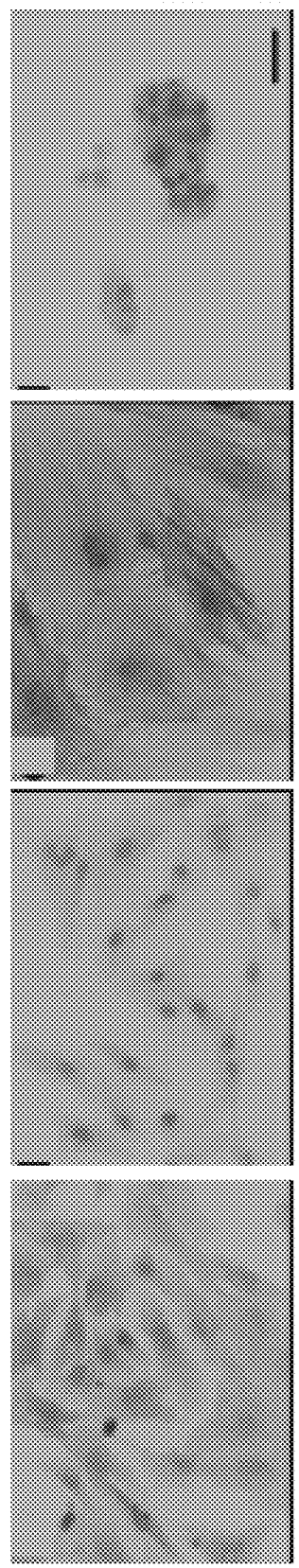

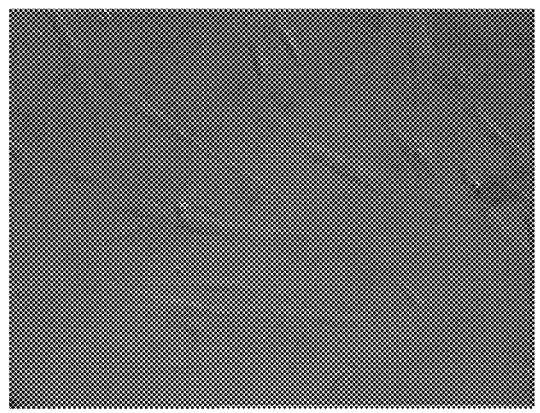 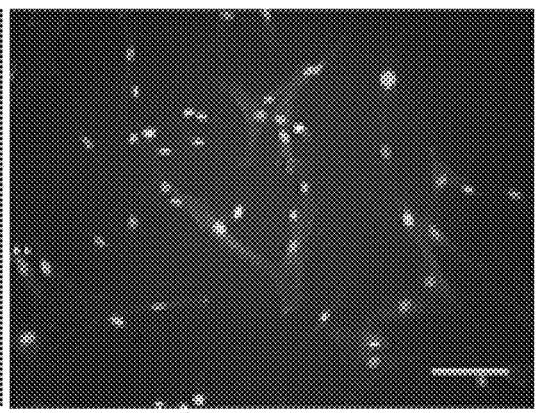
FIG. 25A  FIG. 25B
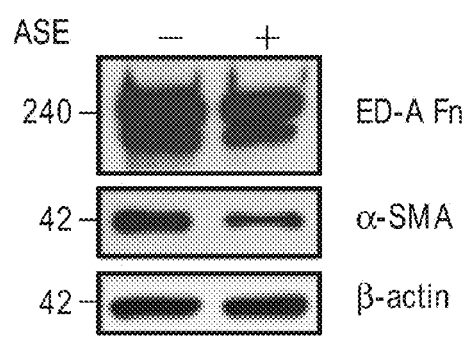
FIG. 25C

AMNIOTIC MEMBRANE PREPARATIONS AND PURIFIED COMPOSITIONS AND THERAPY FOR SCAR REVERSAL AND INHIBITION

CROSS-REFERENCE

This application is a continuation application of U.S. application Ser. No. 13/802,359, filed Mar. 13, 2013, which issued as U.S. Pat. No. 9,161,955 on Oct. 20, 2015, which is a continuation of U.S. application Ser. No. 13/453,765, filed Apr. 23, 2012, which issued as U.S. Pat. No. 8,440,235 on May 14, 2013, which is a continuation of U.S. application Ser. No. 11/528,902, filed Sep. 27, 2006, which issued as U.S. Pat. No. 8,182,840 on May 22, 2012, which claims priority to U.S. Provisional Patent Application No. 60/720,760, filed on Sep. 27, 2005, all of which are incorporated herein by reference in their entireties.

STATEMENT AS TO FEDERALLY SPONSORED RESEARCH

The invention was made with United States government support under grant number RO1 EY06819 awarded by the National Institutes of Health. The United States government may have certain rights in the invention.

FIELD OF THE INVENTION

The invention relates generally to the fields of biology and pharmaceuticals. More particularly, the invention relates to compositions and methods for modulating cellular physiology and pathological processing using a combination of compounds that can be found in amniotic membrane preparations.

BACKGROUND OF THE INVENTION

The placenta is a temporary organ that surrounds the fetus during gestation. The placenta allows for transport of gases and nutrients, and also provides other metabolic and endocrine functions. The placenta is composed of several tissue types. The umbilical cord connects the placenta to the fetus, and transports oxygen to the fetus. The umbilical cord has two arteries and a vein. Wharton's jelly, a specialized gelatinous connective tissue material, surrounds the umbilical cord to protect it from damage during fetal movement and development. The outer "shell" of the placenta is known as the "chorion." Much of the placental disc is composed of chorionic villi, which are extensions of the chorionic villous tree. Through these structures, fetal nutrition exchange occurs. The amniotic membrane (AM) is an avascular membranous sac that is filled with amniotic fluid. This membrane is the innermost membrane surrounding a fetus in the amniotic cavity. This tissue consists of an epithelial layer and a subadjacent avascular stromal layer.

SUMMARY OF THE INVENTION

Described herein are purified compositions and amniotic membrane preparations (that is, compositions that are prepared from amniotic membrane materials, including the amniotic membrane, amniotic stroma and amniotic jelly). In some embodiments, at least one component of the purified compositions are obtained from amniotic membrane preparations. Also described herein are purified compositions in which at least one component of the purified composition is obtained from human placenta and chorion. Also described herein are methods for preparing any of the aforementioned purified compositions and preparations. Also described herein are methods for storing and preserving any of the aforementioned purified compositions and preparations. Also described herein are methods for using any of the aforementioned purified compositions and preparations, including preservative methods, cell culture methods, tissue culture methods, therapeutic methods, prophylactic methods and cosmetic methods.

Various AM preparations exert a number of physiologically significant effects in mammalian cells and intact mammalian tissues. Such effects include suppressing TGF-β signaling, increasing apoptosis of macrophages, decreasing cellular proliferation of, decreasing cellular migration of, and increasing apoptosis of vascular endothelial cells, protecting corneal and limbal epithelial cells and keratocytes from apoptosis induced by storage or by dispase treatment, and decreasing inflammation in tissues. In addition to pieces of intact AM, other preparations described herein include pieces of AM stroma, processed (e.g., ground or pulverized) AM or AM stroma, and various extracts of intact AM and AM stroma. AM extracts can be in liquid or lyophilized powder form. The compositions also include thickened or gel forms of AM extracts which can be made by mixing the AM extracts with a thickener such as one or more extra cellular matrix components (ECM). A large number of ECM components are known such as collagen, hyaluronic acid (HA), and fibrin.

In certain embodiments, a method for inhibiting scar formation in a subject is presented, by providing an effective amount of a scar formation inhibition composition to a subject in need of scar formation inhibition, where the composition has at least one component prepared from a human amniotic material selected from a human amniotic membrane, a human amniotic jelly, a human amniotic stroma, or a combination thereof extracted from an amniotic membrane. The component can be extracted from the human amniotic material. The human amniotic material can be, for example, human amniotic stroma. The extraction procedure can involve, for example, obtaining a frozen or previously-frozen human placenta, thawing the placenta and isolating the human amniotic material from the thawed placenta, homogenizing the human amniotic material in a suitable buffer, optionally lyophilizing the homogenate to a powder, and admixing the homogenate or the powder with a pharmaceutically acceptable carrier for a non-solid dosage form or an extended release solid dosage form. The preparation procedure can substitute the step of lyophilizing the homogenate with the step of: centrifuging the homogenate, isolating the supernatant from the centrifuged homogenate, and optionally lyophilizing the supernatant to a powder.

In further embodiments, a method for reversing scar formation in a subject is presented, by providing an effective amount of a scar reversal composition to a scarred subject, where the composition has at least one component prepared from a human amniotic material selected from a human amniotic membrane, a human amniotic jelly, a human amniotic stroma, or a combination thereof extracted from an amniotic membrane. The component can be extracted from the human amniotic material. The human amniotic material can be human amniotic stroma. In some embodiments, the extraction procedure can involve obtaining a frozen or previously-frozen human placenta, thawing the placenta and isolating the human amniotic material from the thawed placenta, homogenizing the human amniotic material in a suitable buffer, optionally lyophilizing the homogenate to a powder, and admixing the homogenate or the powder with a pharmaceutically acceptable carrier for a non-solid dosage form or an extended release solid dosage form. The preparation procedure can substitute the step of lyophilizing the homogenate with the step of: centrifuging the homogenate, isolating the supernatant from the centrifuged homogenate, and optionally lyophilizing the supernatant to a powder.

Although preparations, materials, and methods similar or equivalent to those described herein can be used in the practice or testing of the present invention, suitable preparations, methods and materials are described herein. All publications mentioned herein are incorporated by reference in their entirety. In the case of conflict, the present specification, including definitions will control. In addition, the particular embodiments discussed below are illustrative only and not intended to be limiting.

Certain Definitions

The term "acceptable" with respect to a formulation, composition or ingredient, as used herein, means having no persistent detrimental effect on the general health of the subject being treated.

"Antioxidants" include, for example, butylated hydroxytoluene (BHT), sodium ascorbate, ascorbic acid, sodium metabisulfite and tocopherol. In certain embodiments, antioxidants enhance chemical stability where required.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

The term "carrier," as used herein, refers to relatively nontoxic chemical compounds or agents that facilitate the incorporation of a compound into cells or tissues.

"Carrier materials" include any commonly used excipients in pharmaceutics and should be selected on the basis of compatibility with compounds disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

The terms "co-administration" or the like, as used herein, are meant to encompass administration of the selected therapeutic agents to a single patient, and are intended to include treatment regimens in which the agents are administered by the same or different route of administration or at the same or different time.

The term "delayed release" as used herein refers to the delivery so that the release can be accomplished at some generally predictable location more distal to that which would have been accomplished if there had been no delayed release alterations.

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), non-crystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein, is an amount effective to achieve a desired pharmacologic effect or therapeutic improvement without undue adverse side effects. It is understood that "an effect amount" or "a therapeutically effective amount" can vary from subject to subject, due to variation in metabolism of the composition, age, weight, general condition of the subject, the condition being treated, the severity of the condition being treated, and the judgment of the prescribing physician.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

By "pharmaceutically acceptable," as used herein, refers to a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutical combination" as used herein, means a product that results from the mixing or combining of more than one active ingredient and includes both fixed and non-fixed combinations of the active ingredients. The term "fixed combination" means that the active ingredients, e.g. the AM preparations and purified compositions described herein and a co-agent, are both administered to a patient simultaneously in the form of a single entity or dosage. The term "non-fixed combination" means that the active ingredients, e.g. the AM preparations and purified compositions described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

The term "polypeptide" or "protein" as used herein can be the full length polypeptide, or a fragment or segment of a polypeptide, and can encompass a stretch of amino acid residues of at least about 8 amino acids, generally at least 10 amino acids, more generally at least 20 amino acids, often at least 30 amino acids, more often at least 50 amino acids or more of the full length polypeptide.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Substantially pure" or "purified" when used in the context of a biological material, amniotic materia and/or a protein context typically means that the material is isolated from other contaminating proteins, nucleic acids, and other biologicals derived from the original source organism. Purity, or "isolation" may be assayed by standard methods, and will ordinarily be at least about 10% pure, more ordinarily at least about 20% pure, generally at least about 30% pure, and more generally at least about 40% pure; in further embodiments at least about 50% pure, or more often at least about 60% pure; in still other embodiments, at least about 95% pure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

As used herein, the term "subject" is used to mean an animal, preferably a mammal, including a human or non-human. The terms patient and subject may be used interchangeably.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 22A-H is a non-limiting example of rapid myofibroblast differentiation of AMSCs in vitro. P0=primary AMSC cells. P1=Passage 1; P2=Passage 2. P0, P1, P2 refer to Passage 0, 1, and 2 respectively. A and E: P0 (4 days); B and F: P0 (7 days); C and G: P1; D and H: P2. Cells in E, F, G, H were immunostained with mouse anti-αSMA monoclonal antibody; A: AMSCs cultured on plastic in DMEM with 10% FBS exhibited a typical fibroblast cell shape. Bar represents 100 µm.

FIG. 22 I is a non-limiting example of a line graph demonstrating that α-SMA-positive myofibroblasts dramatically increased from 71.9±3.7% at 1 week primary culture to 93.9±4.1% at passage 1 and 98.5±1.7% at passage 2.

FIG. 22 J is a non-limiting example of an immunoblot analysis demonstrating the increase of protein expression of α-SMA and ED-A fibronetin (Fn). P0 and P2 refer to Passage 0 and Passage 2, respectively. B-actin is used as a control.

FIGS. 23A through 23I are non-limiting examples of microscopic images demonstrating that differentiated myofibroblast from AMSCs reversed to fibroblasts when cultured back on AM stromal matrix. Myofibroblasts derived from AMSCs at P2 were subcultured on type I collagen (A, C, E, G) or AM stromal matrix (B, D, F, H) in DMEM with 10% FBS for 7 days. Bars represent 100 µm. Live and Dead assay showed cells on both collagen (C) and AM stroma matrix (D) remained 100% viability, but exhibited a different cell shape. Phalloidin and α-SMA double staining showed vivid stress fibers (E) and strong α-SMA expression (G) in myofibroblasts on collagen cultures. In contrast, phalloidin staining became weak and spotty (F), and α-SMA became obscured in cells subcultured on AM stromal matrix (H). I: An immunoblot analysis showed decreased expression of ED-A fibronectin (Fn) and undetectable expression of α-SMA of AMSCs seeded on AM stromal matrix as compared to those seeded on type I collagen.

FIGS. 24A through 24H are non-limiting examples of microscopic images demonstrating that AM Stromal Extracts (ASE) Prevented Myofibroblast Differentiation of AMSCs. Phalloidin staining (upper panel) and α-SMA staining (lower panel) were performed. A and E: cells cultured without ASE for 4 days; B and F: cells cultured for 4 days with ASE; C and G: cells cultured without ASE for 10 days; D and H: Cells cultured with ASE for 10 days. Cells in A, B, C, and D were stained with FITC conjugated phalloidin while cells in E, F, G, and H were stained with mouse anti-α-SMA monoclonal antibody. AMSCs maintained a spindle fibroblastic shape after 4 days cultivation on plastic in DMEM/10% FBS without (A) or with (B) ASE. However, at that time, cells already started to express α-SMA without ASE (E), but did not express α-SMA when ASE was added (F). When cultures were extended for 10 days, cells became enlarged and exhibited prominent stress fibers (C), and strong expression of α-SMA (G) without ASE. In contrast, AMSCs aggregated into spheres of varying sizes with addition of ASE. These spheres did not express stress fibers (D), but expressed weak α-SMA staining (H). Bar represents 100 μm.

FIGS. 25A-C are non-limiting examples of microscopic images demonstrating that amniotic stromal extract (ASE) reverses differentiated myofibroblasts. Myofibroblasts differentiated from AMSCs on plastic in DMEM/10% FBS at passage 2 were cultured with addition of ASE for 1 week. A: Cells reverted from a squamous shape to an elongated or spindle shape B: α-SMA staining became notably decreased. C: An immunoblot analysis demonstrating that ED-A fibronectin and α-SMA levels were reduced as compared to the control without ASE. Bar represents 100 μm.

DETAILED DESCRIPTION OF THE INVENTION

Compositions

Figures 1A, 1B:
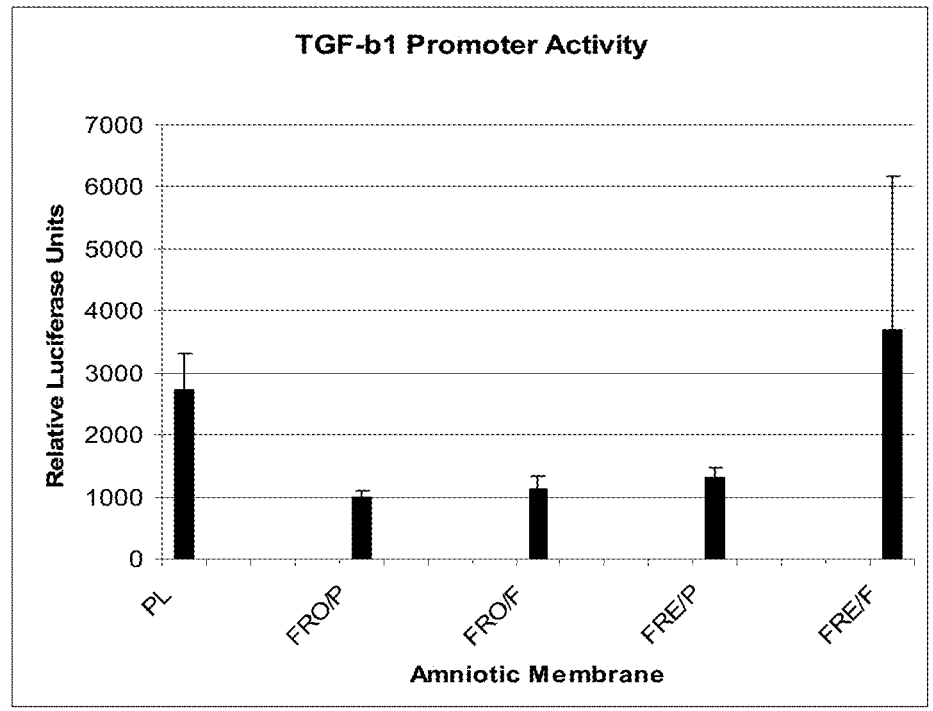
FIG. 1A is a non-limiting example of a bar graph showing the suppression of TGF-β1 promoter activity by various AM Extracts. PL: plastic control. FRO/P: frozen amniotic membrane, placental portion. FRO/F: frozen amniotic membrane, fetal portion. FRE/P: Fresh amniotic membrane, placental portion. FRE/F: Fresh amniotic membrane, fetal portion.
FIG. 1B is a table comparing the P values of the various placental preparations.

Described herein are purified compositions that exert a number of physiologically significant effects in mammalian cells and intact mammalian tissues. The purified compositions comprise at least four components:
Cross-linked high molecular weight hyaluronan (HA);
Tumor necrosis factor-stimulated gene 6 (TSG-6);
Pentraxin (PTX-3); and
Thrombospondin (TSP-1).

Additional components may also be included in purified compositions that have these four components, including: Smad7.

Any or all of the components of the purified compositions described herein can be prepared from a human amniotic material, including human amniotic jelly preparations and extracts (as described herein), human amniotic membrane preparations and extracts (as described herein), and human amniotic stroma preparations and extracts (as described herein).

Together, these four components (with or without Smad7) can suppress TGF-β promoter activity; increase apoptosis in macrophages; decrease proliferation, decrease migration, and increase apoptosis of human vascular endothelial cells; decrease viability of human fibroblasts; decrease inflammation; and prevent apoptosis of epithelial cells exposed to storage and injury.

Hyaluronic acid (HA) is a natural sugar found in the synovial joint fluid, the vitreous humor of the eye, the cartilage, blood vessels, extra-cellular matrix, skin, and umbilical cord. The cross-linking of HA can be through a covalent bound to another molecule, such as a protein. For example, HA can be covalently bound to the heavy chain of inter-α-trypsin inhibitor. The ratio of protein to HA in the AM preparations and purified compositions described herein can be less than about 200:1, less than about 100:1, less than about 50:1, or less than about 10:1.

TSG-6 is a hyaluronan binding protein that plays a role in extracellular matrix remodeling, cell proliferation, and leucocyte migration. TSG-6 can form a complex with the serine protease inhibitor inter-α-inhibitor. PTX-3 (Pentraxins) are $Ca^{2+}$ dependent ligand binding proteins that have a pentameric discoid structure and are present in plasma. TSP-1 (Thrombospondin I) is a homotrimeric glycoprotein having a potent anti-angiogenic and other biological activities. TSP-1 is secreted into the extracellular matrix by a variety of cell types.

These components can be obtained from any suitable source. For example, at least one of the components can be obtained from human tissues, such as amniotic membrane, amniotic jelly, amniotic stroma, or a combination thereof. At least one of the components can be obtained from commercial sources. At least one of the components can be isolated from a transgenic organism. The protein sequences can have a similarity of at least 90%, 93%, 95%, 97%, 99% or 99.5% to the human protein sequence. The components can be purified, substantially purified, partially purified, or can also be present in crude extracts. The components can also be prepared from mammalian amniotic membrane tissues, as each of the four components is present in amniotic membrane tissues.

In additional aspects, the protein Smad7 is also present in the composition. The Smad7 can be obtained from any suitable source, such as from amniotic membrane, from a commercial source, isolated from a transgenic organism.

The Smad7 protein can be purified, substantially purified, partially purified, or can be present in a crude extract.

AM Preparations Derived from Placental Material

In some aspects, at least one of the components HA, TSG-6, PTX-3, TSP-1, optionally Smad7 can be obtained from preparations of amniotic membrane. Alternatively, crude amniotic membrane preparations containing the combination of HA, TSG-6, PTX-3, TSP-1 and optionally Smad7 can be prepared. Exemplary methods of preparing various AM preparations are described herein.

Human placental material can be obtained, for example, from sources such as Bio-Tissue, Inc. (Miami, Fla.) and Baptist Hospital (Miami, Fla.) (under IRB approval). The tissue is typically obtained in either a fresh or frozen state. The tissue can be washed to remove excess storage buffer, blood, or contaminants. The excess liquid can be removed, for example, using a brief centrifugation step, or by other means. The tissue can be frozen, using, for example, liquid nitrogen or other cooling means, to facilitate the subsequent homogenization. The source of the AM tissue can be a human. However, other sources of AM tissue, such as bovine or porcine AM tissue, can be used.

The AM can be used to prepare the composition. AM preparations can include components or portions purified from or extracted from intact AM, AM stromal matrix, HA, AM jelly, and inter-alpha trypsin inhibitor (HA-ITI)). If desired, certain components of the AM preparation can be isolated from the preparation at any time during the process. For example, an extract enriched for a specific protein or set of AM proteins can be isolated from the preparation. After homogenization of the tissue, the larger particles can be separated out, or they can be left in the preparation. The preparation can be dried, if desired. An exemplary preparation method is described in Example 1.

The compositions can also be obtained from AM jelly. AM jelly can be obtained from the fresh AM tissue, or can be obtained before or after the freezing process. The AM jelly can be frozen, and can also be freeze-ground following the procedure for AM preparations as described herein. The jelly can be centrifuged, and can also be lyophilized.

In additional embodiments, a composition made substantially from the stromal layer is prepared. To prepare this composition, the stromal layer is separated from the layer of fresh, frozen, thawed, or otherwise treated AM membrane. The stromal removal can occur, for example, by enzymatic methods, mechanical methods, or by other means. The stromal layer material can be fresh or frozen. The stromal material can be ground or freeze-ground following the procedure for AM preparations as described herein. If desired, the stromal matrix material can be centrifuged, and can also be lyophilized.

The tissue can be frozen prior to the grinding process. The freezing step can occur by any suitable cooling process. For example, the tissue can be flash-frozen using liquid nitrogen. Alternatively, the material can be placed in an isopropanol/dry ice bath or can be flash-frozen in other coolants. Commercially available quick freezing processes can be used. Additionally, the material can be placed in a freezer and allowed to equilibrate to the storage temperature more slowly, rather than being flash-frozen. The tissue can be stored at any desired temperature. For example, −20° C. or −80° C. or other temperatures can be used for storage.

Pulverizing the tissue while frozen, rather than grinding the tissue prior to freezing, is one optional method for preparing the tissue. Alternatively, fresh, partially thawed, or thawed tissue can be used in the grinding step. The tissue (fresh, frozen, or thawed) can then be sliced into pieces of a desired size with a suitable device, such as a scalpel, then ground to fine particles using a BioPulverizer (Biospec Products, Inc., Bartlesville, Okla.) or other suitable devices, and homogenized with a homogenization device such as a Tissue Tearor (Biospec Products, Inc., Dremel, Wis., in a suitable solution. Exemplary solutions include but are not limited to phosphate buffered saline (PBS), DMEM, NaCl solution, and water. The pH of the solution can be adjusted as needed. In some embodiments, the pH range is from about 5.5 or 6.0 to about 8.5. In some embodiments, the frozen tissue is ground in a solution having a pH of between about 6.3, about 6.6, or about 7.0 to about 7.4, about 7.6, or about 7.8.

Any suitable buffer or liquid can be used to prepare the formulations. Example 2 examines the use of various extraction buffers (high salt, low salt, PBS, etc.) on total protein content and HA in the preparation (Table 1). Example 2 further examines the levels of the specific proteins TSG-6 (FIG. 14), PTX-3 (FIG. 18), TSP-1 (FIG. 19), and Smad7 (FIG. 20) using several extraction methods.

The homogenate can then be mixed at any suitable speed, temperature, or other parameters. The mixing can occur, for example, at a temperature range of from about 1° C., or 3° C., to about 6° C., 10° C., 15° C., or 20° C. In some embodiments, the mixing occurs at about 4° C. The homogenate can be mixed, for example, from less than about 1 minute, 10 minutes, or 20 minutes to about 1, 2, 3 or more hours.

The homogenate can then be centrifuged to remove any remaining large particulates, if desired. The centrifugation can be performed using any suitable range of time, temperature, protein concentration, buffers, and speed as desired. The centrifugation can occur, for example, at a range of about 1,000, 5,000, or 10,000×g to about 20,000×g. In some embodiments, the centrifugation occurs at about 15,000×g. The centrifugation can occur for a duration of from less than 1 minute, 5 minutes, 10 minutes, 20 minutes, to about 40 minutes, 60 minutes, 1.5 hours, or more. The supernatant can then be collected and stored in aliquots at −80° C. The total protein can be quantitated, if desired, using any suitable commercial protein analysis kit, such as a BCA assay (Pierce, Rockford, Ill.). Example 2, Table 1, and FIG. 13 describe the analysis of AM preparations after low speed or high speed centrifugation.

For biochemical characterization and purification, the above solutions can be supplemented with protease inhibitors. An exemplary mixture of protease inhibitors is the following: 1 µg/ml aprotinin, 1 µg/ml leupeptin, 1 µg/ml pepstatin A, and 1 mM PMSF. Typically, however, a protease inhibitor is not added to the preparation if it is to be added to live cells or tissues.

The formulation can be tested to confirm the presence of specific components or proteins. For example, the formulation can be tested for the presence of molecules including but not limited to HA, TSG-6, PTX-3, TSP-1, Smad7, and the like. The formulation can also be tested to confirm the absence of pathogens at any point during the preparation process.

AM preparations can be in a liquid, suspension, or lyophilized powder (e.g., ground or pulverized), or other forms. Antimicrobial agents such as antibiotics or antifungal agents may be added. Other substances can be added to the compositions to stabilize and/or preserve the compositions. The material can be packaged and stored, for example, at room temperature, or for example, at −20° C. or −80° C. prior to use.

In some embodiments, the preparation is present as a dry powder formulation. A dry powder formulation can be stored in a smaller volume, and may not require the same low temperature storage requirements to keep the formulation from degrading over time. A dry powder formulation can be stored and reconstituted prior to use. The dry powder formulation can be prepared, for example, by preparing the freeze-ground AM tissue as described herein, then removing at least a portion of the water in the composition. The excess water can be removed from the preparation by any suitable means. An exemplary method of removing the water is by use of lyophilization using a commercially available lyophilizer or freeze-dryer. Suitable equipment can be found, for example, through Virtis, Gardiner, N.Y.; FTS Systems, Stone Ridge, N.Y.; and SpeedVac (Savant Instruments Inc., Farmingdale, N.Y.). The amount of water that is removed can be from about 5%, 10%, 20%, 30% to about 60, 70, 80, 90, 95 or 99% or more. In some embodiments, substantially all of the excess water is removed. The lyophilized powder can then be stored. The storage temperature can vary from less than about −196° C. −80° C., −50° C., or −20° C. to more than about 23° C. If desired, the powder can be characterized (weight, protein content, etc) prior to storage.

The lyophilized powder can be reconstituted in a suitable solution or buffer prior to use. Exemplary solutions include but are not limited to PBS, DMEM, and BSS. The pH of the solution can be adjusted as needed. The concentration of the AM can be varied as needed. In some procedures a more concentrated preparation is useful, whereas in other procedures, a solution with a low concentration of AM is useful. Additional compounds can be added to the composition. Exemplary compounds that can be added to the reconstituted formulation include but are not limited to pH modifiers, buffers, collagen, HA, antibiotics, surfactants, stabilizers, proteins, and the like. The lyophilized AM powder can also be added to a prepared cream, ointment or lotion to result in the desired concentration.

Additional components can be added to the composition as desired. In some embodiments, water soluble or powdered AM preparations can be mixed with an ECM component such as collagen, fibrin, or HA.

Collagen is a major structural protein found in the body. It provides support for tissues, connects tissue to bone, and provides the structure of the body. When the body is in the healing process, collagen plays a role in helping to build a cellular structure. Hyaluronic acid is a natural sugar found in the synovial joint fluid, the vitreous humor of the eye, the cartilage, blood vessels, extra-cellular matrix, skin, and umbilical cord. Fibrin is a protein involved in the clotting of blood.

Water-soluble AM preparation can be mixed with collagen, fibrin or with HA Similarly, lyophilized powder AM preparation can be mixed with collagen, fibrin or HA. Collagen, fibrin and HA can be are suitable delivery vehicles, as AM preparations mixed with collagen or HA were shown to exert a suppressive effect upon TGF-β promoter activity. Although AM preparations were mixed with collagen gel and HA gel in the experiments described herein, any soluble forms (e.g., liquid) of collagen and HA or other ECM components (e.g., fibrin) can be used. The collagen, fibrin or HA can be derived from any suitable source organism. When collagen, fibrin or HA are added, the ratio of these compounds to AM can be varied as desired. For example, a ratio of AM to collagen (or fibrin or HA) of less than about 0.001:1, 0.01:1, 0.05:1, or 0.1:1, to about 1:1, 1.5:1, 2:1, 5:1, 10:1, 100:1 or 1000:1 or more can be used.

Collagen gel can be prepared, for example, by diluting the stock solution (4 mg/ml) with 0.1 N acetic acid and by mixing it with appropriate volume ratios of 20×DMEM or suitable buffer, and 1 N NaOH, as described in Example 1. The collagen in the preparation can be present, for example, at a range of from less than about 2 mg/ml to more than about 4 mg/ml.

Various dilutions of high MW HA can be prepared, for example, by diluting commercially prepared HA (Healon™ (10 mg HA/ml) (Pharmacia, LaJolla, Calif.) in DMEM or suitable buffer. Lyophilized powder and water-soluble forms of AM preparations can be diluted in a solution such as PBS, DMEM, or other solutions into the desired collagen concentration. The HA in the preparation can be present, for example, at a range of from less than about 2 μg/ml to more than about 129 μg/ml.

The following procedures represent illustrative methods for preparing the amniotic preparations and purified compositions described and used herein.

Preparation of Preserved Human AM:

Human placenta was collected at elective cesarean delivery (Heiligenhaus et al., Invest Ophthalmol Vis Sci. 42:1969-1974, 2001, Lee and Tseng, Am J Ophthalmol. 123:303-312, 1997, Prabhasawat et al., Ophthalmology, 104:974-985, 1997, Tseng et al., Arch Ophthalmol. 116:431-441, 1998). The AM was flattened onto nitrocellulose paper (Hybond N+, Amersham, England), with the epithelium surface up. The AM samples were stored at −80° C. in DMEM/glycerol 1:2 (v/v) until use.

Amniotic Membrane Extract Preparations

Fresh and frozen human placentas were obtained from Bio-Tissue, Bio-tissue, Inc. (Miami, Fla.). The entire procedure for preparation of total human AM extracts (AME) was carried out aseptically so as to be used for subsequent cell culture-based experiments. The AM was sliced into small pieces to fit into the barrel of a BioPulverizer (Biospec Products, Inc., Bartlesville, Okla.), frozen in the liquid nitrogen, pulverized into a fine powder, and weighed. Cold 1×PBS buffer, pH 7.4, containing protease inhibitors (protease inhibitor cocktail, P8340, Sigma, and supplemented with 1 mM PMSF) and phosphatase inhibitors (50 mM sodium fluoride and 0.2 mM sodium vanadate) was added to the powder at 1:1 (ml/g). The mixture was kept on ice and homogenized with a Tissue Tearor (Biospec Products, Inc., Dremel, Wis.) 5 times, 1 minute each, with a 2 minute cooling interval. These water-soluble extracts were designated as "Total" AM extracts (AME).

Total AM extracts were divided into two 50 ml conical centrifuge tubes. One was centrifuged at high speed (HS, 48,000×g) and the other one was centrifuged at a low speed (LS, 15,000×g) at 4° C. Aliquots of the HS and LS supernatant were transferred to sterile 1.5 ml Eppendorf tubes and were designated as AM/HS, AM/LS, respectively. Desired AM/HS samples were frozen at −20° C. for 1 h before lyophilization. The samples then were placed in the chamber of FreeZone (Labconco, Kansas City, Mo.) with holes on the cap. Samples were lyophilized at −50° C. at a vacuum of 0.85 mBar for 5 hours. Before use, the samples were reconstituted with the sterile distilled H$_2$O to the same volume. The same method was also used to prepare extracts from AM jelly, which was easily scraped from the adherent material on the AM stroma.

Total Soluble Human Amniotic Membrane and Amniotic Membrane Jelly Extract Preparations Frozen human placenta material was obtained from Bio-Tissue, Bio-tissue, Inc. (Miami, Fla.). The entire procedure for preparation of total human AM extracts (AME) was carried out aseptically so as to be used for subsequent cell culture-based experiments. The AM was sliced into small pieces to fit into the barrel of a BioPulverizer (Biospec Products, Inc., Bartlesville, Okla.), frozen in the liquid nitrogen, pulverized into a fine powder, and weighed. Cold 1×PBS buffer, pH 7.4, containing protease inhibitors (protease inhibitor cocktail, P8340, Sigma, and supplemented with 1 mM PMSF) and phosphatase inhibitors (50 mM sodium fluoride and 0.2 mM sodium vanadate) was added to the powder at 1:1 (ml/g). The mixture was kept on ice and homogenized with a Tissue Tearor (Biospec Products, Inc., Dremel, Wis.) 5 times, 1 minute each, with a 2 minute cooling interval. These water-soluble extracts were designated as "Total" AM extracts (AME).

The total water-soluble extract was mixed for 1 hr at 4° C., subsequently fractionated by two different speeds of centrifugation at 4° C. for 30 min, i.e., 15000×g and 48000× g, and the resultant supernatant was designated as L and H, respectively. Each supernatant was divided into aliquots and stored at −80° C. This method was also used to prepare extracts from AM jelly, which was easily scraped from the adherent material on the AM stroma.

Total Soluble Human Amniotic Membrane and Amniotic Membrane Jelly Extracts by Different Buffers and Fractionation Methods In examining preparations in different extraction buffers, the powder as prepared from above was weighed and mixed with Buffer A (Isotonic Low salt): 100 mM Tris-HCl, pH 7.6, 150 mM NaCl, 4 mM EDTA, 1% Triton X-100 at the wet weight (g) of AM to the buffer (ml) at 1:1 ratio by stirring at 4° C. for 1 hr. After centrifugation at 48000×g, the resultant pellet was subsequently extracted by Buffer B (high salt): 100 mM Tris-HCl, pH 7.6, 1 M NaCl, 4 mM EDTA, 1% Triton X-100 by stirring at 4° C. for 1 hr. Again after centrifugation at 48000×g, the pellet was finally extracted by Buffer C (4 M guanidine hydrochloride): 100 mM sodium acetate, pH 5.8, 4 M guanidine hydrochloride, 4 mM EDTA, 1% Triton X-100 by stirring at 4° C. for 24 hr. All the above three buffers were supplemented with the following protease and phosphatase inhibitors: 1 µg/ml aprotinin, 1 µg/ml leupeptins, 1 µg/ml pepstatin A, 0.5 mM PMSF, 50 µM sodium fluoride and 0.2 µM sodium vanadate. The resultant supernatants, designated as Extract A, B, and C, respectively, were dialyzed against the dislysis buffer (50 mM Tris-HCl, pH7.5, 0.15 M NaCl) supplemented with 0.5 mM PMSF at 4° C. for 6 hr and dialysis buffer was changed twice, each with 500× (the volume ratio—dialysis buffer: samples). After dialysis, the volume of each sample was measured and adjusted to the same volume with the dialysis buffer. The same method was also used to prepare extracts from AM jelly, which was the adherent material on the AM stroma that could be easily scraped off.

Preparation of Total Soluble Human Amniotic Membrane Extracts in PBS

The entire procedure for preparation of total soluble human AM extracts (T) was carried out aseptically so as to be used for subsequent cell culture-based experiments. Frozen human placenta was obtained from Bio-tissue, Inc. (Miami, Fla.), from which AM was retrieved. AM was sliced into small pieces to fit into the barrel of a BioPulverizer (Biospec Products, Inc., Bartlesville, Okla.), frozen in the liquid nitrogen, and then pulverized into a fine powder. The powder was weighed and mixed with cold PBS buffer (prepared by adding distilled $H_2O$ to 1×PBS, pH7.4, from 10×PBS, cat#70011-044, Invitrogen, Carlsbad, Calif.) with protease inhibitors (protease inhibitor cocktail, P8340, Sigma, and supplemented with 1 mM PMSF) and phosphatase inhibitors (50 mM sodium fluoride and 0.2 mM sodium vanadate) at 1:1 (ml/g). The mixture was kept in the ice and homogenized with a Tissue Tearor (Biospec Products, Inc., Dremel, Wis.) for 5 times, 1 min each with a 2 min interval cooling. This water-soluble extract was designated as "Total" (T). The total water-soluble extract was mixed for 1 hr at 4° C., centrifuged at 4° C. for 30 min at 48000×g. The supernatant was divided into aliquots and stored at −80° C.

Preparation of Water-Soluble AM Stromal Extracts

Using aseptic techniques, frozen human AM obtained from Bio-Tissue, Inc. (Miami, Fla.) was briefly washed 2-3 times with HBSS to remove the original storage medium. The AM stroma was scraped by spatula, frozen in the air phase of liquid nitrogen and grounded to fine particles by BioPulverizer (Biospec Products, Inc., Bartlesville, Okla.) followed by homogenization on ice with Tissue Tearor (Biospec Products, Inc., Dremel, Wis.) in PBS, pH 7.4, for 1 min. The homogenate was mixed by rotation for 1 h and centrifuged at 14,000×g for 30 min at 4° C. The supernatant in PBS was then collected, and stored in aliquots at −80° C. The protein concentration was determined by BCA assay. This water-soluble protein extract, designated as amniotic stromal extract (ASE), was used for experiments described herein.

AM Stromal Extract Preparation

The complete procedure for preparation of protein extracts was carried out aspectically. Frozen human AM obtained from Bio-Tissue (Miami, Fla.) was briefly washed 2-3 times with HBSS (Invitrogen, Carlsbad, Calif.) to remove the storage medium. AM stroma was scraped from the stromal side of the AM by spatula for AM stroma extract preparation. Human placenta as well as chorion obtained from Baptist Hospital (Miami, Fla.) was rinsed 3 times with HBSS to remove blood. To prepare the water-soluble protein extract, total AM, scraped AM stroma, stroma-removed AM, placenta, and chorion were each frozen in the air phase of liquid nitrogen and each ground to fine particles using a BioPulverizer (Biospec Products, Inc., Bartlesville, Okla.) followed by homogenization on ice with Tissue Tearor (Biospec Products, Inc., Dremel, Wis.) in PBS (pH 7.4) for 1 min. Each homogenate was mixed for 1 hour and centrifuged at 14,000 g for 30 min at 40° C. Each supernatant (in PBS) was then collected and stored in aliquots (0.5 ml) at −80° C. A BCA assay (Pierce, Rockford, Ill.) was used to quantitate the total protein in different extracts.

Preparing Water-Soluble and Lyophilized Powder Forms of Human AM Extracts

In a typical procedure for preparing human AM extracts, the entire procedure is carried out aseptically. Unless otherwise noted, the AM extracts can be handled at room temperature during the steps of the procedure. First, fresh or frozen human AM is obtained, preferably from Bio-Tissue, Inc. (Miami, Fla.). Frozen AM is briefly washed 2-3 times with HBSS (Invitrogen, Carlsbad, Calif.) to remove the storage medium. Fresh human placenta or chorion is rinsed 3 times with HBSS to remove blood.

To prepare the water-soluble form of AM extracts, the AM (e.g., AM stroma, stroma-removed AM, placenta, chorion) is transferred to a sterile 50 ml centrifuge tube and centrifuged at 4° C. for 5 min at 5000×g to remove the excess fluid. The AM is weighed, transferred to a 100 mm or 150 mm sterile Petri dish, and frozen in the air phase of a liquid nitrogen container for 20 min to facilitate the subsequent homogenization. The frozen AM is then sliced into small pieces with a disposable scalpel or ground to fine particles using a BioPulverizer (Biospec Products, Inc., Bartlesville, Okla.) or other suitable device, and homogenized with Tissue Tearor (Biospec Products, Inc., Dremel, Wis.), or other suitable device, in phosphate buffered saline (PBS) or DMEM without phenol red (Invitrogen, Carlsbad, Calif.) at neutral pH. For biochemical characterization and purification, the above solutions are supplemented with the following proteinase inhibitors: 1 µg/ml aprotinin, 1 µg/ml leupeptin, 1 µg/ml pepstatin A, and 1 mM PMSF. However, if the extract is to be directly added to cell culture, no protease inhibitor is added. The homogenate is mixed at 4° C. for 30 min and centrifuged at 15,000×g for 30 min. The supernatant (i.e., AM extract) is collected and stored in aliquots (0.5 ml) at −80° C. A BCA assay (Pierce, Rockford, Ill.) is used to quantitate the total protein in each AM extract.

To prepare the lyophilized powder form of AM extracts, frozen AM is ground to fine particles using a BioPulverizer (Biospec Products, Inc., Bartlesville, Okla.), or other suitable device, and further homogenized as described herein. Aliquots of approximately 0.5 ml are lyophilized by Speed-Vac (Savant Instruments Inc., Farmingdale, N.Y.) at 4° C. for 4 h to decrease the weight from 280 mg to 32 mg (~89% reduction). The lyophilized powder is weighed and stored at −80° C. Before use, the lyophilized powder can be reconstituted in a suitable buffer.

To prepare AM stromal extracts, the AM stroma is scraped from the stromal surface of intact total AM leaving the basement membrane and the amniotic epithelium intact, and the frozen AM stroma is ground using a BioPulverizer as described herein. The stroma is extracted with PBS (e.g., 1.4 mg/ml) at a neutral pH at 4° C. for 30 min and centrifuged at 15,000×g for 30 min. The supernatant is collected and stored in aliquots (0.5 ml) at −80° C. A BCA assay (Pierce, Rockford, Ill.) is used to quantitate the total protein in the AM stromal extract.

Methods involving conventional molecular biology techniques are described herein. Such techniques are generally known in the art and are described in detail in methodology treatises such as Molecular Cloning: A Laboratory Manual, $3^{rd}$ ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 2003 (with periodic updates). Various techniques for culturing animal cells are known in the art and are described in Culture of Animal Cells: A Manual of Basic Technique, $4^{th}$ ed., R. Ian Freshney, Wiley-Liss, Hoboken, N.J., 2000, and Animal Cell Culture Techniques (Springer Lab Manual), M. Clynos, Springer-Verlag, New York, N.Y., 1998. Methods involving protein analysis and purification are also known in the art and are described in Protein Analysis and Purification: Benchtop Techniques, $2^{nd}$ ed., Ian M. Rosenberg, Birkhauser, New York, N.Y., 2004.

Pharmaceutical Compositions

AM preparations can be formulated for administration purposes as a non-solid dosage form, for example, by combining with a delivery vehicle to create compositions such as solutions, drops, suspensions, pastes, sprays, ointments, oils, emulsions, aerosols, a coated bandage, a patch, creams, lotions, gels, and the like. The formulation used will depend upon the particular application. Gels are useful for administering the compositions because they allow better retention of the active ingredient at the site of introduction, allowing the active ingredient to exert its effect for a longer period of time before clearance of the active ingredient. Alternatively, AM preparations can be formulated as extended-release solid dosage forms (including oral dosage forms). A description of exemplary pharmaceutically acceptable carriers or vehicles and diluents, as well as pharmaceutical formulations, is provided herein and can also be found in Remington's Pharmaceutical Sciences, a standard text in this field, and in USP/NF.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery* Systems, Seventh Ed. (Lippincott Williams & Wilkins; 1999), herein incorporated by reference in their entirety.

In certain embodiments, the compositions include a pharmaceutically acceptable diluent(s), excipient(s), or carrier(s). In addition, the AM preparations and purified compositions described herein can be administered as pharmaceutical compositions in which AM preparations and purified compositions described herein are mixed with other active ingredients, as in combination therapy. In some embodiments, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions can also contain other therapeutically valuable substances.

A pharmaceutical composition, as used herein, refers to a mixture of a AM preparations and purified compositions described herein with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of AM preparations and purified compositions described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

Topical Formulations

Formulations of the AM preparations and purified compositions described herein include those suitable for topical administration. The formulations may conveniently be presented in unit dosage form and may be prepared by any methods well known in the art of pharmacy. The amount of active ingredients which can be combined with a carrier material to produce a single dosage form will vary depending upon the host being treated, the particular mode of administration.

Suspensions may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Typical compositions described herein include a wide variety of physical forms. These include, but are not limited to, solutions, lotions, creams, oils, gels, sticks, sprays, ointments, balms, shampoo, and pastes. Generally, such carrier systems can be described as being solutions, emulsions, gels, solids, and aerosols. The compositions may be applied topically to the skin, or may be applied in the form of a transdermal delivery device, such as a microneedle, a patch, bandage, or gauze pad known in the art.

The ointments, pastes, creams and gels may contain, in addition to the AM preparations and purified compositions described herein, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the AM preparations and purified compositions described herein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Solvents are generally employed in the preparation of suitable topical compositions. Such solvents can either be aqueous or organic based. The solvent must be capable of having dispersed or dissolved therein the active ingredients while not being irritating to the animal being treated. Water forms the basis for all aqueous solvents, while suitable organic solvents include propylene glycol, butylene glycol, polyethylene glycol, polypropylene glycol, glycerol, 1,2,4-butanetriol, sorbitol esters, 1,2,6-hexanetriol, ethanol, isopropanol, butanediol, and mixtures thereof. Solvents can be included in the overall composition in amounts ranging from 0.1% to 99% and preferably from 2.0% to 75%. In some embodiments, the compositions are produced in the form of an emollient-containing composition. A wide variety of suitable emollients are known and may be used herein.

In some embodiments, the compositions are formulated as lotions containing from about 0.01% to 10% of the AM preparations and purified compositions described herein. In other embodiments, the compositions are formulated in a solution carrier system as a cream. A cream composition would preferably comprise from about 0.1% to 15% and preferably from 1% to 5% of the the AM preparations and purified compositions described herein. Lotions and creams can be formulated as emulsions as well as solutions. The compositions may also be administered in liquid form, including in the form of liposomes suspended in liquid, as in the different type of sprays available in this industry.

In other embodiments, the active ingredients are formulated as ointments. Suitable ointments may comprise simple bases of animal or vegetable oils, or semi-solid hydrocarbons (oleaginous). Suitable ointments may also comprise absorption ointment bases which absorb water to form emulsions. Ointment carriers may also be water soluble. An ointment may comprise from 1% to 99% of an emollient plus to about 0.1% to 99% of a thickening agent.

The proportion of the AM preparations and purified compositions described herein in the compositions can vary from between about 0.01 wt. % to about 100 wt. %, more preferably from about 0.1 wt. % to about 99.9 wt. %, and especially from about 1.0 wt. % to about 99.0 wt. %.

"Carriers" or "vehicles" preferably refer to carrier materials suitable for topical administration and include any such materials known in the art, such as any liquid, gel solvent, liquid diluent, solubilizer, or the like, which is non-toxic, and which does not interact with other components of the composition in a deleterious manner. Examples of suitable carriers for use herein include water, silicone, liquid sugars, waxes, oils, petroleum jelly, and a variety of other materials.

In some embodiments, the carrier or vehicle includes one or more solvents, oils, surfactants, humectants, thickening agents, antioxidants, chelating agents, buffers, and preservatives.

Examples of solvents include $C_2$-$C_{10}$ alcohols, such as hexanol, cyclohexanol, benzyl alcohol, 1,2-butanediol, glycerol, and amyl alcohol; $C_5$-$C_{10}$ hydrocarbons such as n-hexane, cyclohexane, and ethylbenzene; $C_4$-$C_{10}$ aldehydes and ketones, such as heptylaldehyde, cyclohexanone, and benzylaldehyde; $C_4$-$C_{10}$ esters, such as amyl acetate and benzyl propionate; ethereal oils, such as oil of eucalyptus, oil of rue, cumin oil, limonene, thymol, and 1-pinene; halogenated hydrocarbons having 2-8 carbon atoms, such as 1-chlorohexane, 1-bromohexane, and chlorocyclohexane.

Examples of oils comprise fats and oils such as olive oil and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate.

Examples of surfactants include anionic surfactants such as sodium stearate, sodium cetyl sulfate, polyoxyethylene laurylether phosphate, sodium N-acyl glutamate; cationic surfactants such as stearyldimethylbenzylammonium chloride and stearyltrimethylammonium chloride; ampholytic surfactants such as alkylaminoethylglycine hydrochloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxypropylene glycol (e.g., the materials sold under the trademark "Pluronic"), polyoxyethylene castor oil, and polyoxyethylene lanolin.

Examples of humectants include glycerin, 1,3-butylene glycol, and propylene glycol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid.

In certain embodiments, the carrier/vehicle is composed of the foregoing materials to achieve a controlled occlusion of the skin, thereby resulting in optimal enhancement of biologically active moiety penetration across the skin with minimal skin irritation. In certain embodiments, the carrier/vehicle may include a dispersing agent that aids in maintaining a particulate phase of the active ingredients dispersed in the continuous phase. In other embodiments, non-ionic excipients, such as lauric alcohol, propylene glycol monolaurate, myristyl lactate, lauryl lactate, or the like, facilitate dispersion. The rate of biologically active moiety delivery across a dermal surface can be increased by transdermal delivery enhancers. Suitable transdermal delivery enhancers include proton-accepting solvents such as dimethylsulfoxide and dimethylacetamide. Other suitable transdermal delivery enhancers include 2-pyrrolidine, N,N-diethyl-m-toluamide, 1-dodecylazacycloheptan-2-one, N,N-dimethylformamide, N-methyl-2-pyrrolidine, terpenes, surfactants, and calcium thioglycolate.

Suitable dermal penetration enhancers include 1-5 carbon fatty acid esters of para-aminobenzoic acid, isopropyl palmitate, isopropyl myristate, ethanol, isobutyl alcohol, isobutyl alcohol, stearyl alcohol, glycerol, 2-pyrrolidone, urea, propylene glycol, oleic acid, palmitic acid, dimethyl sulfoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, 2-pyrrolidone-5-carboxylic acid, N,N-dimethyl-m-toluamide, urea, ethyl acetate, 1-dodecylazacycloheptan-2-one, oleic acid, imidazoline, butylurea, and pyrrolidone carboxylic acid esters.

Wetting agents, emulsifiers, surfactants, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

As appropriate compositions for topical application there may be cited all compositions usually employed for topically administering therapeutics, e.g., creams, jellies, dressings, shampoos, tinctures, pastes, ointments, salves, powders, liquid or semiliquid formulations, and the like. Application of said compositions may be by aerosol, e.g., with a propellant such as nitrogen carbon dioxide, a freon, or without a propellant such as a pump spray, drops, lotions, or a semisolid such as a thickened composition which can be applied by a swab. In particular compositions, semisolid compositions such as salves, creams, pastes, jellies, ointments, and the like will conveniently be used.

Ophthalmic Formulations

The AM preparations and purified compositions described herein can be administered in a variety of ways, including all forms of local delivery to the eye. Additionally, the AM preparations and purified compositions described herein can be administered systemically, such as orally or intravenously. The AM preparations and purified compositions described herein can be administered topically to the eye and can be formulated into a variety of topically administrable ophthalmic compositions, such as solutions, suspensions, gels or ointments. Thus, "ophthalmic administration" encompasses, but is not limited to, intraocular injection, subretinal injection, intravitreal injection, periocular administration, subconjuctival injections, retrobulbar injections, intracameral injections (including into the anterior or vitreous chamber), sub-Tenon's injections or implants, ophthalmic solutions, ophthalmic suspensions, ophthalmic ointments, ocular implants and ocular inserts, intraocular solutions, use of iontophoresis, incorporation in surgical irrigating solutions, and packs (by way of example only, a saturated cotton pledget inserted in the fornix).

A composition comprising the AM preparations and purified compositions described herein can illustratively take the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition may include a gel formulation. In other embodiments, the liquid composition is aqueous. Alternatively, the composition can take the form of an ointment.

Useful compositions can be an aqueous solution, suspension or solution/suspension, which can be presented in the form of eye drops. A desired dosage can be administered via a known number of drops into the eye. For example, for a drop volume of 25 µl, administration of 1-6 drops will deliver 25-150 µl of the composition. Aqueous compositions typically contain from about 0.01% to about 50%, more typically about 0.1% to about 20%, still more typically about 0.2% to about 10%, and most typically about 0.5% to about 5%, weight/volume of the AM preparations and purified compositions described herein.

Typically, aqueous compositions have ophthalmically acceptable pH and osmolality. "Ophthalmically acceptable" with respect to a formulation, composition or ingredient typically means having no persistent detrimental effect on the treated eye or the functioning thereof, or on the general health of the subject being treated. Transient effects such as minor irritation or a "stinging" sensation are common with topical ophthalmic administration of agents and consistent with the formulation, composition or ingredient in question being "ophthalmically acceptable."

Useful aqueous suspension can also contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Useful compositions can also comprise an ophthalmically acceptable mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful compositions may also include ophthalmically acceptable solubilizing agents to aid in the solubility of components of the AM preparations and purified compositions described herein. The term "solubilizing agent" generally includes agents that result in formation of a micellar solution or a true solution of the agent. Certain ophthalmically acceptable nonionic surfactants, for example polysorbate 80, can be useful as solubilizing agents, as can ophthalmically acceptable glycols, polyglycols, e.g., polyethylene glycol 400, and glycol ethers.

Useful compositions may also include one or more ophthalmically acceptable pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an ophthalmically acceptable range.

Useful compositions may also include one or more ophthalmically acceptable salts in an amount required to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful compositions may also include one or more ophthalmically acceptable preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions may include one or more ophthalmically acceptable surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions may include one or more antioxidants to enhance chemical stability where required. Suitable antioxidants include, by way of example only, ascorbic acid and sodium metabisulfite.

Aqueous suspension compositions can be packaged in single-dose non-reclosable containers. Alternatively, multiple-dose reclosable containers can be used, in which case it is typical to include a preservative in the composition.

The ophthalmic composition may also take the form of a solid article that can be inserted between the eye and eyelid or in the conjunctival sac, where it releases the AM preparations and purified compositions described herein. Release is to the lacrimal fluid that bathes the surface of the cornea, or directly to the cornea itself, with which the solid article is generally in intimate contact. Solid articles suitable for implantation in the eye in such fashion are generally composed primarily of polymers and can be biodegradable or non-biodegradable.

Injectable Formulations

Formulations suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, AM preparations and purified compositions described herein may be formulated in aqueous solutions, in physiologically compatible buffers such as Hank's solution, Ringer's solution, physiological saline buffer, or other suitable solutions. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Transdermal Formulations

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety.

The transdermal dosage forms described herein may incorporate certain pharmaceutically acceptable excipients which are conventional in the art. In one embodiments, the transdermal formulations described herein include at least three components: (1) a formulation as described herein; (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of AM preparations and purified compositions described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the AM preparations and purified compositions described herein can be accomplished by means of iontophoretic patches and the like. Additionally, transdermal patches can provide controlled delivery of the composition. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Solid Oral Dosage Forms

The pharmaceutical solid dosage forms described herein can include one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences,* 20th Edition (2000).

Compressed tablets are solid dosage forms prepared by compacting the bulk blend of the formulations described herein. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of the composition from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the composition described herein, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the composition and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

The pharmaceutical solid dosage forms including AM preparations and purified compositions described herein can be further formulated to provide a controlled release of the composition. Controlled release refers to the release of the composition from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

In other embodiments, the formulations described herein are delivered using a pulsatile dosage form. A pulsatile dosage form is capable of providing one or more immediate release pulses at predetermined time points after a controlled lag time or at specific sites. Pulsatile dosage forms may be administered using a variety of pulsatile formulations known in the art. For example, such formulations include, but are not limited to, those described in U.S. Pat. Nos. 5,011,692, 5,017,381, 5,229,135, and 5,840,329, each of which is specifically incorporated by reference. Other pulsatile release dosage forms suitable for use with the present formulations include, but are not limited to, for example, U.S. Pat. Nos. 4,871,549, 5,260,068, 5,260,069, 5,508,040, 5,567,441 and 5,837,284, all of which are specifically incorporated by reference.

Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms,* 2 Ed., Vol. 1, pp. 209-214 (1990); Singh et al., *Encyclopedia of Pharmaceutical Technology,* $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference.

In some embodiments, pharmaceutical formulations are provided that include particles of the compositions described herein and at least one dispersing agent or suspending agent for administration to a subject. The formulations may be a powder and/or granules for suspension, and upon admixture with water, a substantially uniform suspension is obtained.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium docusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Intranasal Formulations

Intranasal formulations are known in the art and are described in, for example, U.S. Pat. Nos. 4,476,116, 5,116,817 and 6,391,452, each of which is specifically incorporated by reference. Formulations can be prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). These compositions and formulations can be prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present.

For administration by inhalation, the compositions described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the AM preparations and purified compositions described herein and a suitable powder base such as lactose or starch.

Other Formulations

The AM preparations and purified compositions described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Methods of Dosing and Treatment Regimens

The compositions can be administered by any suitable technique. Typically, the compositions will be administered directly to a target site (e.g., ocular surface, skin). The administration of formulations to the ocular surface is well known in the art. If delivery of AM preparations to the skin is desired, topical administration can be used. An injectable composition is also envisioned. Administration can also be parenteral (e.g., subcutaneous). Other methods of delivery, e.g., liposomal delivery, diffusion from a device impregnated with the composition, and microemulsion-based transdermal delivery in both cosmetic and pharmaceutical applications, are known in the art.

The compositions containing the AM preparations and purified compositions described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the AM preparations and purified compositions described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, preferably 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the AM preparations and purified compositions described herein are from about 0.01 to 2.5 mg/kg per body weight. An indicated daily dosage in the larger mammal, including, but not limited to, humans, is in the range from about 0.5 mg to about 100 mg, conveniently administered in divided doses, including, but not limited to, up to four times a day or in extended release form. Suitable unit dosage forms for oral administration include from about 1 to 50 mg active ingredient. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

The compositions and methods described herein may also be used in conjunction with other well known therapeutic reagents that are selected for their particular usefulness against the condition that is being treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the skilled physician after evaluation of the disease being treated and the condition of the patient.

It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the AM preparations and purified compositions described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The AM preparations and purified compositions described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, preferably about 1 month to about 5 years, and more preferably from about 1 month to about 3 years.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition.

For example, the container(s) can include one or more AM preparations and purified compositions described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may include one or more additional containers, each with one or more of various materials (such as reagents, optionally in concentrated form, and/or devices) desirable from a commercial and user standpoint for use of the AM preparations and purified compositions described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

Methods of Treatment

The AM preparations and purified compositions described herein have many uses including research and clinical applications. Based on the results described herein, the AM preparations and purified compositions described herein can be applied to tissues or cells to achieve a desired modulation of physiology. AM preparations and purified compositions described herein can further be added to cell cultures or tissue cultures to achieve a desired effect (as described herein).

AM Preparations and Purified Compositions Described Herein Suppress TGF Promoter Activity The anti-scarring, anti-inflammatory, and anti-angiogenic activities of AM preparations and purified compositions described herein is demonstrated by the suppression of TGF-$\beta$1 promoter activity as shown herein. The fetal portion of the frozen amniotic membrane has a significantly higher anti-scarring effect than that of fresh amniotic membrane; the placental portion of the frozen amniotic membrane also has a significantly higher anti-scarring effect than the fresh amniotic membrane (Example 1). Therefore, the frozen AM, either the placental or fetal portion, showed more potent suppressive effects in TGF-$\beta$ than the fresh AM. This suppressive effect mediated by total AM extract obtained from frozen AM was dose-dependent over a range of 0.4 to 125 μg/ml. Furthermore, such a suppressive effect could not be substituted by high MW HA alone (exceeding 100× of equivalent AM extract), and was lost after digestion with hyaluronidase, suggesting that it was mediated by a complex between HA-I$\alpha$I. Centrifugation at low or high speed did not affect the suppressive effect significantly. However, subsequent lyophilization and reconstitution produced a more potent suppressive effect. Additionally, the overall suppressive effect of AM was more potent than that of AM jelly.

TGF-$\beta$ is the prototypic cytokine that is involved in tissue inflammation, in addition to wound healing and scar formation. See Border, et al., J. Clin. Invest., 90:1-7 (1992); Grande, Proc. Soc. Exp. Biol. Med., 214:27-40 (1997); Jester, et al., Prog. Retin. Eye Res., 18(3):311-356 (1999); and Marek, et al., Med. Sci. Monit., 8(7):RA145-151 (2002). Mammalian cells express three different TGF-$\beta$s: TGF-$\beta$1, TGF-$\beta$2, and TGF-$\beta$3. TGF-$\beta$ is the most potent cytokine promoting myofibroblast differentiation by up-regulating expression of $\alpha$-SMA, integrin $\alpha$5$\beta$1, and EDA domain-containing fibronectin (Fn) in a number of cell types, including fibroblasts. See Tseng, et al., Ocular Surface J., 2(3):177-187 (2004); Ronnov-Jessen, et al., Lab. Invest., 68:696-707 (1993); Verbeek, et al., Am. J. Pathol., 144:372-82 (1994); Hales, et al., Curr. Eye Res., 13:885-90 (1994); Jester, et al., Cornea, 15:505-16 (1996); Serini, et al., J. Cell. Biol., 142:873-81 (1998); Grande, Proc. Soc. Exp. Biol. Med., 214(1):27-40 (1997); and Jester, et al., Prog. Retin. Eye. Res., 18:311-56 (1999). TGF-$\beta$ also up-regulates the expression of such matrix components as collagens and proteoglycans, down-regulates proteinase and matrix metalloproteinases, and up-regulates their inhibitors. Collectively, these actions result in increased cell-matrix interactions and adhesiveness, as well as deposition and formation of scar tissue. See Tseng, et al., Ocular Surface J., 2(3):177-187 (2004); Grande, Proc. Soc. Exp. Biol. Med., 214(1):27-40 (1997); Jester, et al., Prog. Retin. Eye. Res., 18:311-56 (1999); and Lawrence, Eur. Cytokine Netw., 7:363-74 (1996).

TGF-$\beta$s exert their actions via binding with TGF-beta receptors (TGF-$\beta$Rs) on the cell membrane. In human cells, there are three TGF-$\beta$Rs, namely TGF-$\beta$R type I (TGF-$\beta$RI), type II (TGF-$\beta$RII), and type III (TGF-$\beta$RIII). TGF-$\beta$s, serving as ligands, bind with a serine, threonine kinase receptor complex made of TGF-$\beta$RI and TGF-$\beta$RII; such a binding is facilitated by TGF-$\beta$RIII, which is not a serine, threonine kinase receptor. See Tseng, et al., Ocular Surface J., 2(3):177-187 (2004); and Massague, et al., Genes and Development., 14:627-44 (2000). Binding with TGF-$\beta$RII activates TGF-$\beta$RI, which is responsible for direct phosphorylation of a family of effector proteins known as Smads, which modulate transcription of a number of target genes, including those described herein, participating in scar formation. See Tseng, et al., Ocular Surface J., 2(3):177-187 (2004); Massague, et al., Genes and Development., 14:627-44 (2000); and Derynck, et al., Biochem. Biophys. Acta., 1333:F105-F150 (1997).

Suppression of TGF-β can be achieved by neutralizing antibodies to TGF-β and agents that intercede the signaling mediated by TGF-β such as decorin. See Shahi, et al., Lancet, 339:213-214 (1992); Petroll, et al., Curr. Eye Res., 1739:736-747 (1998); Yamaguchi, et al., Nature, 346(6281): 281-284 (1990); and Logan, et al., Exp. Neurol., 159:504-510 (1999). Most of the literature has shown suppression of TGF-β being achieved at the level of modulating the TGF-β activation, binding with its receptor, or its signal transduction. It has been shown that amniotic membrane can achieve such an inhibition at the level of transcription, i.e., to turn off transcription of TGF-β genes. In particular, amniotic membrane has been shown to suppress TGF-β signaling in human corneal and limbal fibroblasts, and human conjunctival and pterygium body fibroblasts. See Tseng, et al., J Cell Physiol., 179:325-335 (1999); and Lee, et al., Curr. Eye Res., 20(4): 325-334 (2000).

Application of the AM preparations and purified compositions described herein can be used to lower the production or activity of TGF-β. Several types of AM compositions, such as AME (total human AM extract), the AME supernatant after centrifugation, AM jelly, and AM stroma were prepared as detailed in Example 1. The effect of various buffers, such as PBS, low salt buffer, high salt buffer, and guanidine HCl on TGF-β activity was examined. Additionally, the effect of various freeze-grinding procedures on TGF-β activity was examined.

Figure 3:
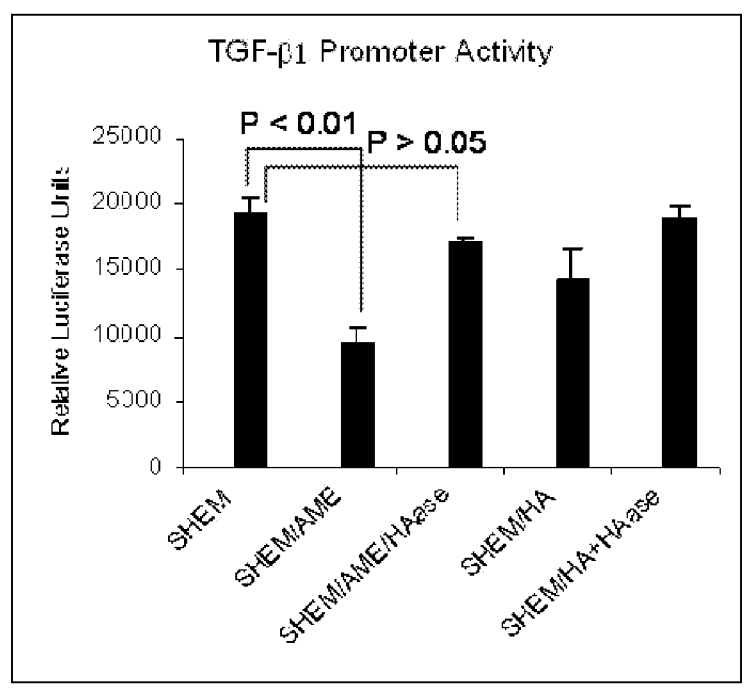
FIG. 3 is a non-limiting example of a bar graph showing the effect of various AM extract preparations on the suppression of TGF-β1 promoter activity.
Figure 4:
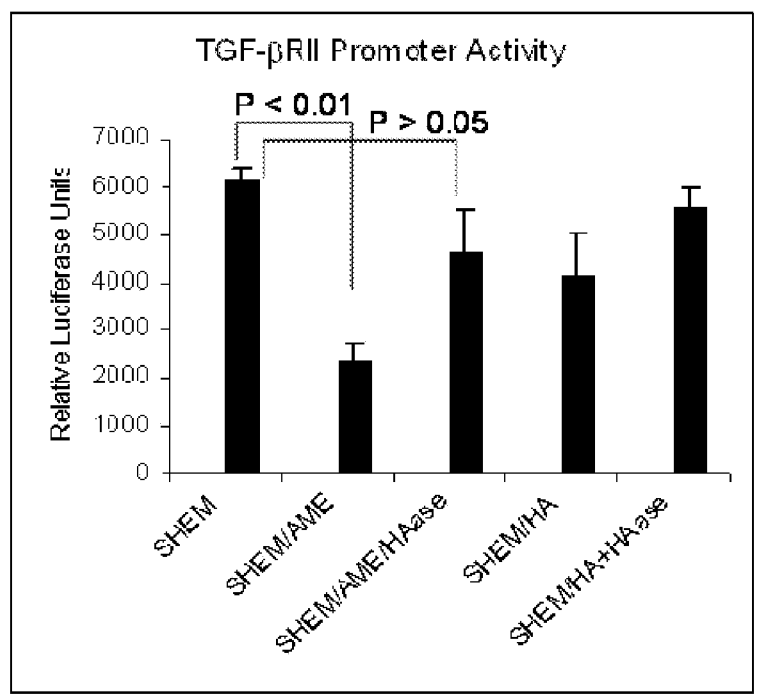
FIG. 4 is a non-limiting example of a bar graph showing the effect of various AM extract preparations on the suppression of TGF-βRII promoter activity.
Figure 5:
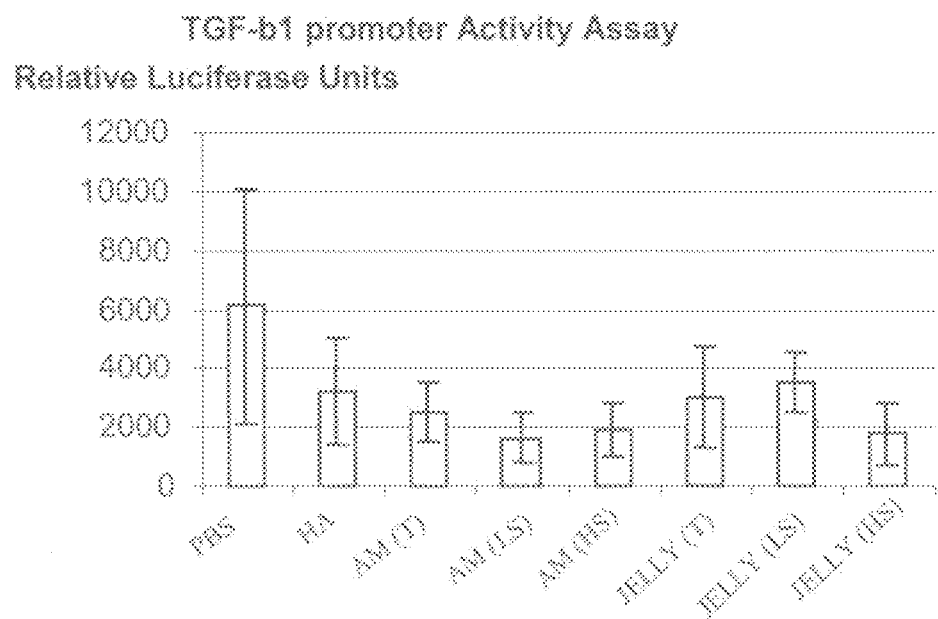
FIG. 5 is a non-limiting example of a bar graph demonstrating that soluble AME and jelly extracts derived after centrifugation do not alter the suppressive effect on TGF-β Promoter Activities. HA, AM (Total (T), Low Speed (LS), High speed (HS)) and Jelly (Total (T), Low Speed (LS), High Speed (HS)) showed suppression of TGF-β□1 promoter activation compared to the PBS control when normalized with beta-galatosidase activity.
Figure 6:
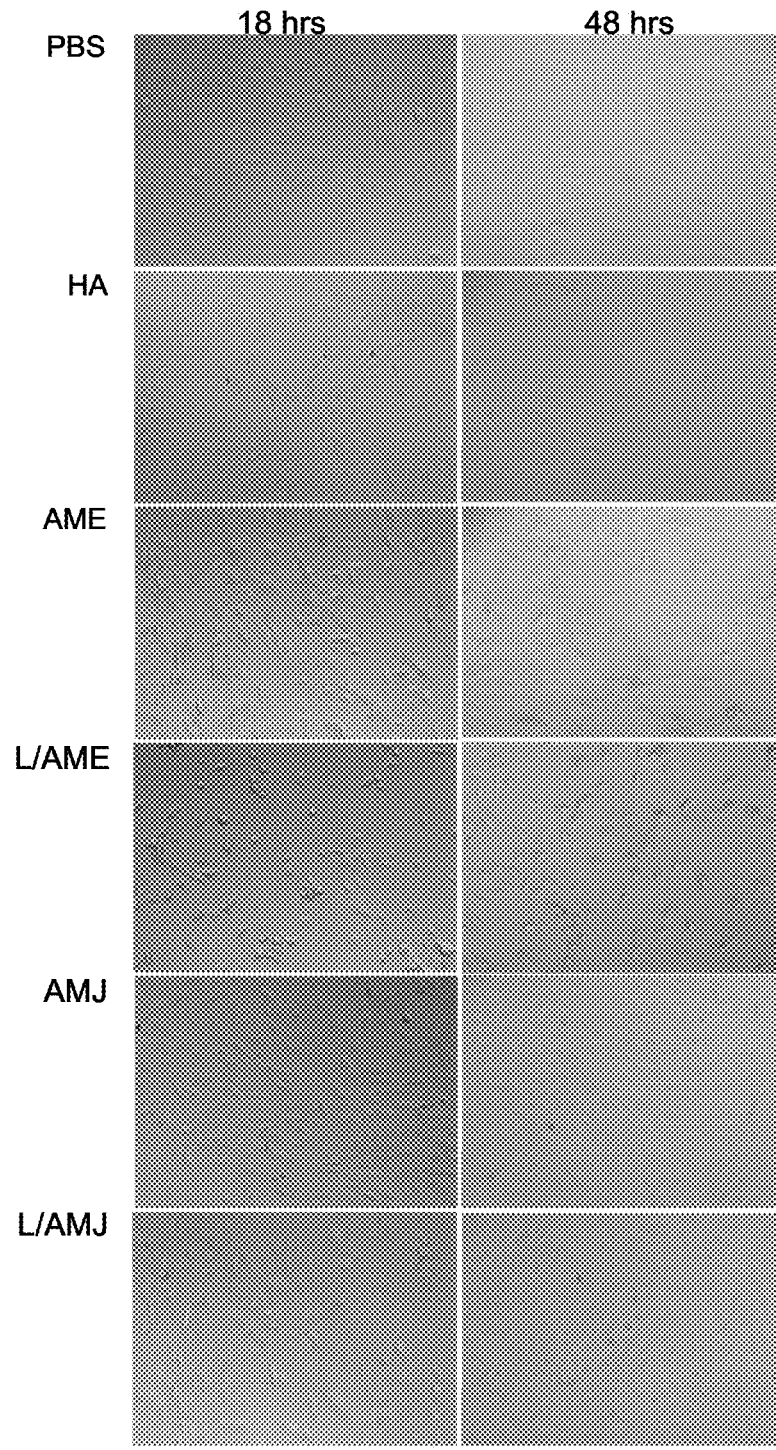
FIG. 6 is a non-limiting example of a set of microscopic images of human corneal fibroblasts showing cell morphology changes either 18 or 48 hours after treatment with various compounds. PBS: the PBS control; HA: hyaluronic acid; AME: amniotic membrane extract; L/AME: lyophilized amniotic membrane extract; AMJ: amniotic membrane jelly; L/AMJ: lyophilized amniotic membrane jelly.
Figure 8:
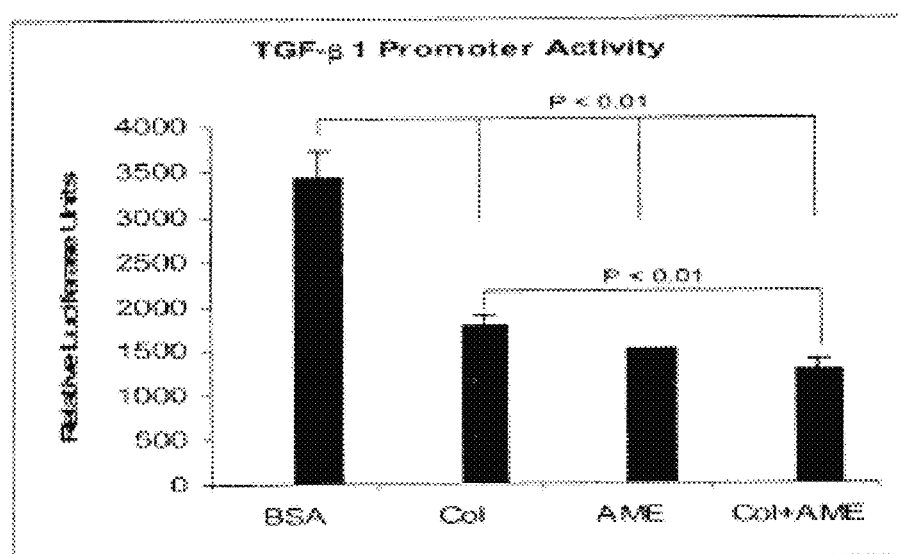
FIG. 8 is a non-limiting example of a bar graph showing the effect of the addition of collagen gel (Col), AM extract AME, or collagen gel mixed with AM extract (Col+AME) on the suppression of TGF-β promoter activity. BSA was used as a control.
Figure 9:
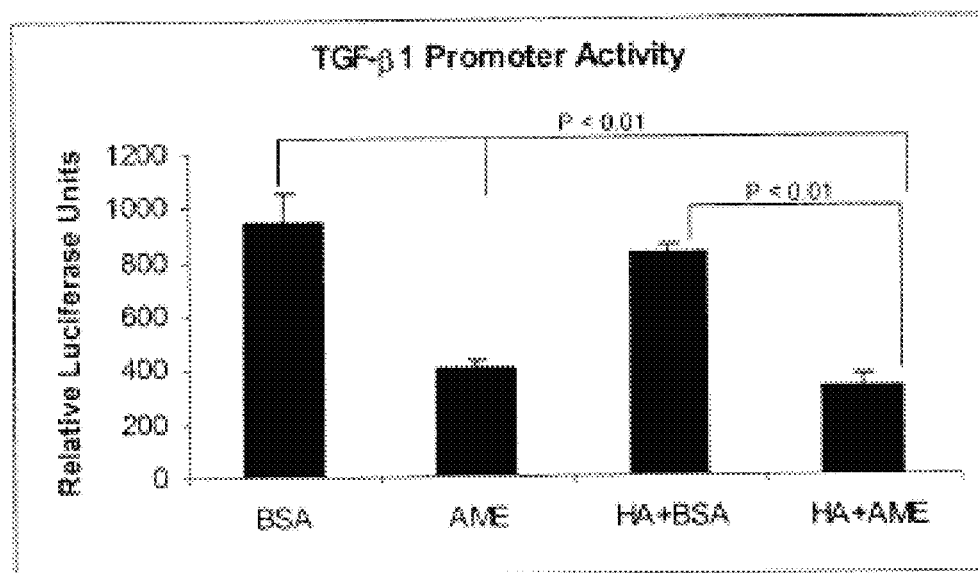
FIG. 9 is a non-limiting example of a bar graph comparing the effect of treatment with AME, HA, or HA+AME, compared to a control assay with BSA alone, on the suppression of TGFβ1 activity. The promoter activity is displayed as relative luciferase units (RLU).

The suppression of TGF-β activity was lost after hyaluronidase digestion, demonstrating that the suppressive effect may be mediated by a HA-related complex (FIG. 3). The suppressive effect was not recovered by addition of HA. The centrifugation step did not alter the suppression of TGF-β activity, in either AME or AM jelly extracts (FIG. 5). Lyophilization enhanced the suppression of TGF-β activity of both AME and jelly extract (FIG. 6). FIG. 8 and FIG. 9 demonstrate that collagen and HA, when added to AME, can enhance the suppression of TGF-β activity. Accordingly, addition of collagen and HA to the AM-based compositions may be useful to treat various diseases involving TGF-β.

As shown herein, TGF-β is downregulated by the disclosed compositions. Accordingly, the compositions described herein can be used to treat diseases related to TGF-β is downregulation, such as angiogenesis, wound healing, and tissue inflammation.

AM Preparations and Purified Compositions Described Herein can Prevent Apoptosis The AM preparations and purified compositions described herein can be used to prevent, lessen, or treat apoptosis in tissues. In some embodiments, the AM preparations and purified compositions described herein can decrease or prevent apoptosis in tissues that have been injured. This anti-apoptotic effect demonstrates that the compositions can be used to prolong the life of organs being stored prior to transplant. The compositions can also be used to treat or prevent damage during and after surgical procedures. Example 3 demonstrates the anti-apoptotic effect of AM extract using a murine model of eye damage. Mouse eyes were collected and damaged either by enzymatic treatment or by mechanical injury, AM extract was administered, and the effect on cellular damage was determined, using an assay that measures apoptotic damage to the nucleus. Incubation with AM extract was found to decrease the levels of apoptosis.

Because of the anti-apoptotic effects exerted by AM preparation, AM preparations and compositions are expected to be useful for preserving tissues (e.g., cornea) before transplantation. The addition of AM preparations to tissues that are being stored can be helpful in lessening cellular damage due to the storage process. For example, the AM preparations and purified compositions described herein can be used to decrease the amount of degradation that occurs in a tissue that is being stored prior to transplantation or surgical procedures. The AM preparations and purified compositions described herein can be added to the storage medium, with or without collagen and/or HA. Stored tissues such as eyes, organs, skin, and the like can benefit from the decreased cellular apoptosis that occurs when an AM composition is added.

Once a donor tissue is harvested, it is typically stored in a storage medium until transplantation. The compositions can be added to the storage medium to prevent cellular apoptosis. For example, the compositions can be added to storage media for preserving limbal epithelial stem cells. Similarly, AM preparation-containing compositions can be added to cell culture medium or digestion medium to prevent cellular (e.g., keratocyte) apoptosis. Because studies described herein show that incubation of AM preparation during dispase digestion (a treatment which mimics surgical and pathological insults such as excimer ablation in PRK and recurrent corneal erosion, respectively) significantly reduced apoptosis of both epithelial cells and keratocytes, the compositions can also be administered to an eye receiving mechanical scraping or excimer laser photoablation to attempt to reduce keratocyte apoptosis, and hence reduce corneal haze. As another example, AM preparation-containing formulations can also be used in surgical conditions or diseases such as recurrent corneal erosion or keratoconus where the basement membrane is dissolved to reduce the keratocyte apoptosis.

The AM Preparations and Purified Compositions Described Herein can Prevent or Reverse Scar Formation and can be Used to Assist in Wound Healing In adult humans and other mammalian vertebrates, wound healing in tissue such as skin is generally a reparative process, in contrast to a regenerative process which appears to take place in healing of fetal and embryonic tissue. The outcome of a wound repair process appears to be influenced by a number of different factors, including both intrinsic parameters, e.g. tissue oxygenation; and extrinsic parameters, e.g. wound dressings. There is, however, considerable evidence indicating that the overall process of healing and repair of wound damaged tissue, including the necessary cellular communication, is regulated in a coordinate manner in adult humans and other mammals by a number of specific soluble growth factors which are released within the wound environment and which, among other things, appear to induce neovascularization, leukocyte chemotaxis, fibroblast proliferation, migration, and deposition of collagen and other extra-cellular matrix molecules within the wounds. Such growth factors that have been identified and isolated are generally specialized soluble proteins or polypeptides and include transforming growth factor alpha (TGF-α), transforming growth factor beta (TGF-β1, TGF-β2, TGF-β3, etc.), platelet derived growth factor (PDGF), epidermal growth factor (EGF), insulin-like growth factors I and II (IGFI and IGFII) and acidic and basic fibroblast growth factors (acidic FGF and basic FGF).

Myofibroblasts are phenotypically intermediate between smooth muscle cells and fibroblasts. Myofibroblasts play an important role in morphogenesis and oncogenesis, inflammation, wound healing, and fibrosis in most organs and tissues. During normal wound healing, fibroblasts migrate to the wound area and differentiate into myofibroblasts under the influence of growth factors such as TGF-β1 and the mechanical stress developed within a given tissue. Normally, myofibroblasts gradually disappear by apoptosis in the resolution phase. However, under certain pathological situations, myofibroblasts persist and continue to remodel the extracellular matrix, resulting in scar formation. Thus, the ability to control myofibroblast differentiation can be useful to prevent scar formation in various tissues during wound healing. The AM preparations and purified compositions described herein are able to both prevent and reverse scar formation, and can thus be useful for treatment of any diseases where scar formation can occur.

In some embodiments, the AM preparations and purified compositions described herein can decrease or prevent the formation of scar tissue. This effect is demonstrated in Example 5. AMSCs were cultured on either plastic, collagen, or AM tissue surface material. The AMSCs cultured on plastic rapidly differentiated to myofibroblasts in vitro. However, these differentiated myofibroblasts could be reversed to AMSCs when subcultured on AM stromal matrix (FIG. 23). Reversal of myofibroblast differentiation could also be obtained when amniotic stromal extract was added to differentiated myofibroblasts (FIG. 25). Further, AM stromal extract was also found to prevent myofibroblast differentiation of AMSCs (FIG. 26).

Accordingly, the AM preparations and purified compositions described herein can be used to prevent or reverse scar formation that is caused by any means. The compositions can be administered to treat wrinkles, stretch marks, surgical scars, wound scars, scars from burns or mechanical injuries, and the like.

The AM preparations and purified compositions described herein can be used to treat or prevent scar formation due to wounds. Wounds are internal and external bodily injuries or lesions caused by physical means, such mechanical, chemical, viral, bacterial, fungal and other pathogenic organisms, or thermal means, which disrupt the normal continuity of tissue structures. Wounds may be caused by accident, surgery, pathological organisms, or by surgical procedures.

Additionally, the AM preparations and purified compositions described herein can suppress fibroblast migration. As shown in Example 6 and FIGS. 27 through 29, AME was found to suppress migration of fibroblasts. Human limbal explants (HLE) were cultured in SHEM or SHEM supplemented with AME to study the biological activity of AME. AME (at 25 μg/ml) delayed the onset of epithelial outgrowth from the limbal explant. AME suppressed migration of explant fibroblasts from the stroma, resulting in an outgrowing epithelial sheet with much less fibroblasts. Furthermore, the epithelial sheet expanded in SHEM containing AME had a smooth edge, a phenomenon resembling when HLE was cultured in SHEM with 10 μM SB203580—a MAPK p38 inhibitor. Histological sections of the remaining explant after outgrowth revealed that without AME, an increase in dissolution of the stromal matrix was evident. Thus, AME may be able to inhibit fibroblast migration by preventing stromal matrix lysis. These discoveries indicate that AME can be used for developing new products to modify wound healing in the direction promoting expansion of human corneal stem cells and against inflammation, scarring, and angiogenesis.

The AM preparations and purified compositions described herein can be used during or after surgery, to improve healing and to decrease the amount of tissue damage from mechanical insults to the tissue. The applicable use of the compositions and methods described herein is widespread and includes, but is not limited to all types of surgery, such as plastic, spinal cord, or caesarian section; disease, such as cancer, congestive heart failure, and kidney disease; and conditions as a result of burns, acne, or other injuries. The methods described herein can be used by physicians in reconstructive or plastic surgeries. The AM preparations and purified compositions described herein can also be applied topically on the body surface or tissues to achieve short-term and long-term therapeutic effects.

The AM preparations and purified compositions described herein can be used to treat or prevent damage due to eye disease. Types of eye diseases that can be treated by administering the AM preparations and purified compositions described herein include but are not limited to dry eye, corneal injury, corneal ulcer, Sjogren's syndrome, damage from contact lenses, fungal infection, viral infection, or bacterial infection, mechanical injury, surgical damage, burn damage, conjunctival inflammation, ocular pemphigoid, Stevens-Johnson syndrome, chemical injury, and the like. The AM preparations and purified compositions described herein can also be used to treat epidermal diseases. Types of epidermal layer diseases that can be treated by administering the AM preparations and purified compositions described herein include but are not limited to fungal diseases, viral diseases, bacterial diseases, rash, eczema, psoriasis, ichthyosis, epidermalytic hyperkeratosis, and the like.

The compositions and methods described herein are provided further detail in the following examples. These examples are provided by way of illustration and are not intended to limit the invention in any way.

EXAMPLES

Example 1: Suppressive Activities of Various Amniotic Membrane Preparations

Hyaluronidase Digestion

AM total water-soluble extracts (AME) prepared from frozen AM were mixed with or without 10 units/ml hyaluronidase (Sigma #H1136) in the reaction buffer (50 mM HEPES, pH7.5, 0.1 M NaCl, 1% Triton X-100, 0.1% BSA supplemented with the above protease and phosphatase inhibitors for 2 hours at 37° C. using a positive control of high MW HA (cat# H1876, Sigma) purified from human umbilical cords.

Cell Culture and TGF-β1 Promoter Suppression

When human corneal fibroblasts cultured on 100 mm plastic dish in DMEM/10% FBS reached 80% confluency (~$1.0 \times 10^6$ cells), cells were washed twice with DMEM/10% FBS. Adenoviruses-TGF-β1 promoter-luciferase (MOI=37.5) and Adeno-CMV-beta-gal (MOI=30) were added to the culture plates with 10 ml of the fresh DMEM/10% FBS and cells were incubated at 37° C. for 4 hours, and trypsinized for 5 minutes using 4 ml prewarmed trypsin/EDTA. After trypsin/EDTA activity was neutralized with 8 ml of DMEM/10% FBS, cells were collected into a 15 ml tube and centrifuged at 1,500 rpm (~600×g) for 5 min. After decanting the medium, cells were resuspended in 15 ml DMEM/10% FBS, and cell viability was measured by trypan blue stain. Viable $3 \times 10^4$ cells were seeded on a plastic 24 well or on the stromal surface of AM inserts. A total of 4 wells or inserts were prepared. Cells were then incubated at 37° C. in a $CO_2$ incubator for 48 hours.

After carefully removing the growth medium from each well, cells were rinsed with 0.5 ml PBS at lease twice, taking care not to dislodge attached cells. After removing as much as PBS in the well, 100 µl 1× lysis buffer was added to cover the cells, and cells were mechanically scraped and transferred to a microcentrifuge tube placed on ice. Cell lysates were collected by vortexing for 10-15 sec and centrifuging at 12,000×g for 15 sec at room temperature. The supernatant designated as cell lysate was stored at −80° C. prior to assaying for luciferase activities.

Suppression of TGF-β1 Promoter Activity by Different AM Extracts

In FIG. 1, compared to the plastic control (PL), both the placental portion and the fetal portion of frozen amniotic membrane (FRO/P and FRO/F, respectively) showed significant suppression of TGF-β1 promoter activity (each $P<0.01$). For the fresh placenta, the placental portion of amniotic membrane (FRE/P) also exhibited a significant suppression of TGF-β1 promoter activity ($P<0.05$). Nevertheless, the fetal portion of the fresh amniotic membrane (FRE/F) did not show any suppressive effect ($P=0.5$). These results indicated that the fetal portion of the fresh amniotic membrane does not have the same anti-scarring effect as the frozen counterpart. For the frozen amniotic membrane, the suppressive effect by the placental portion (FRO/P) was not significantly different from that by the fetal portion ($P=0.3$). For the fresh amniotic membrane, the suppressive effect by the fetal portion (FRE/F) was not significantly from the placental portion (FRE/P) ($P=0.1$). For the placental portion, the suppressive effect by the frozen amniotic membrane (FRO/P) was significantly better than the fresh amniotic membrane (FRE/P) ($P<0.05$). In the fetal portion, however, the suppressive effect by the frozen amniotic membrane (FRO/F) was not significantly different than the suppressive effect of the fresh amniotic membrane (FRE/F) ($P=0.1$).

Figure 2:
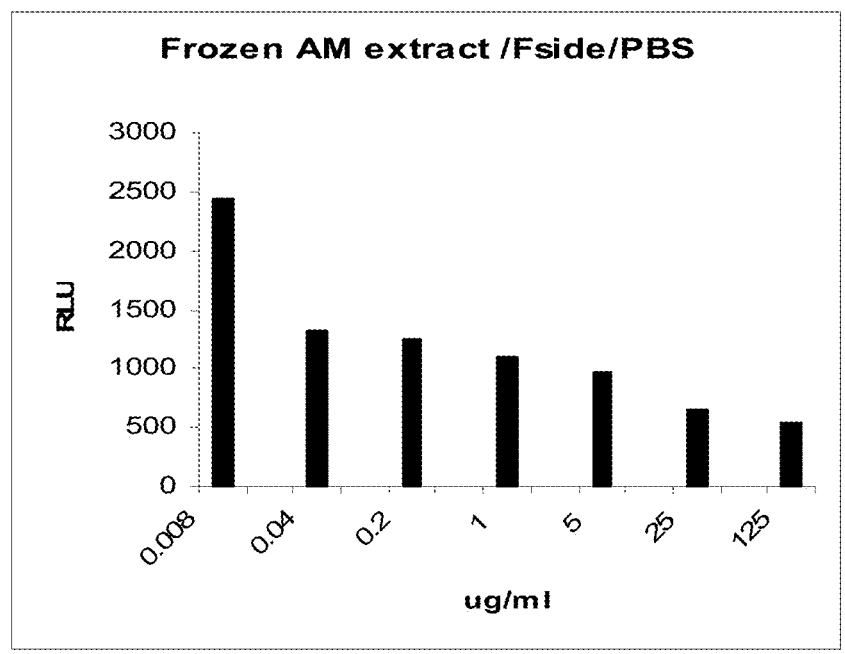
FIG. 2 is a non-limiting example of a bar graph showing the dose response curve of TGF-β1 promoter activity suppression. RLU: Relative luciferase units.

Suppression of TGF-β1 Promoter Activity is Dose-Dependent and Lost after Digestion with Hyaluronidase The suppression of TGF-β1 promoter activity by total water-soluble AM extracts prepared from frozen AM obeyed a dose-responsive curve from 0.04 to 125 µg/ml (FIG. 2). As shown by the promoter activity of TGF-β1 and TGF-βRII, the suppressive effect of 25 µg/ml of total water-soluble AM extracts prepared from frozen AM was lost when pre-treated with hyaluronidase, indicating that such a suppressive effect was mediated by an HA-related complex (FIG. 3). It should be noted that 25 µg/ml AM extracts contained less than 0.78 µg/ml HA.

Lost Suppressive Effect from Hyaluronidase Cannot be Recovered by Addition of HA Although 100 µg/ml high MW HA alone showed a mild suppressive activity, its magnitude was still significantly less than 25 µg/ml AM extracts. Taken together, these data suggest that the suppressive effect of AM extracts was mediated by HA-linked complex, i.e., HA-IαI complex.

Soluble AME and Jelly Extracts Derived after Centrifugation do not Change the Suppressive Effect on TGF-β1 Promoter Activities Compared to the PBS control, HA, AM (Total, Low Speed, High speed) and Jelly (Total, Low Speed, High Speed) showed suppression of TGF-β1 promoter activation when normalized with beta-galatosidase activity. P value indicated there was not statistically significant due to the variation among the control group (data not shown). By comparing total AME and two conditions of centrifuged soluble AME, results suggested that there was no significant difference. However, without centrifugation of AME showed less suppression compare with low or high soluble AME. Likewise, Jelly/T indicated less TGF-β suppression activities in comparison with Jelly/HS (FIG. 5).

Lyophilization Enhanced the Suppressive Effect of AME and Jelly Extract

Human corneal fibroblasts showed no change in cell morphology in the control, HA alone, and low concentrations of AME or jelly extracts (Data not shown). However, cells showed a marked change to slender and small cells after the treatment with high concentration of AME and L/AME, as early as 18 hrs after seeding (FIG. 6). Furthermore, the cell density also decreased. The above changes were even more dramatic in lyophilized AME or L/AME than their non-lyophilized counterparts in AME or Jelly extracts, respectively (FIG. 6).

Figure 7:
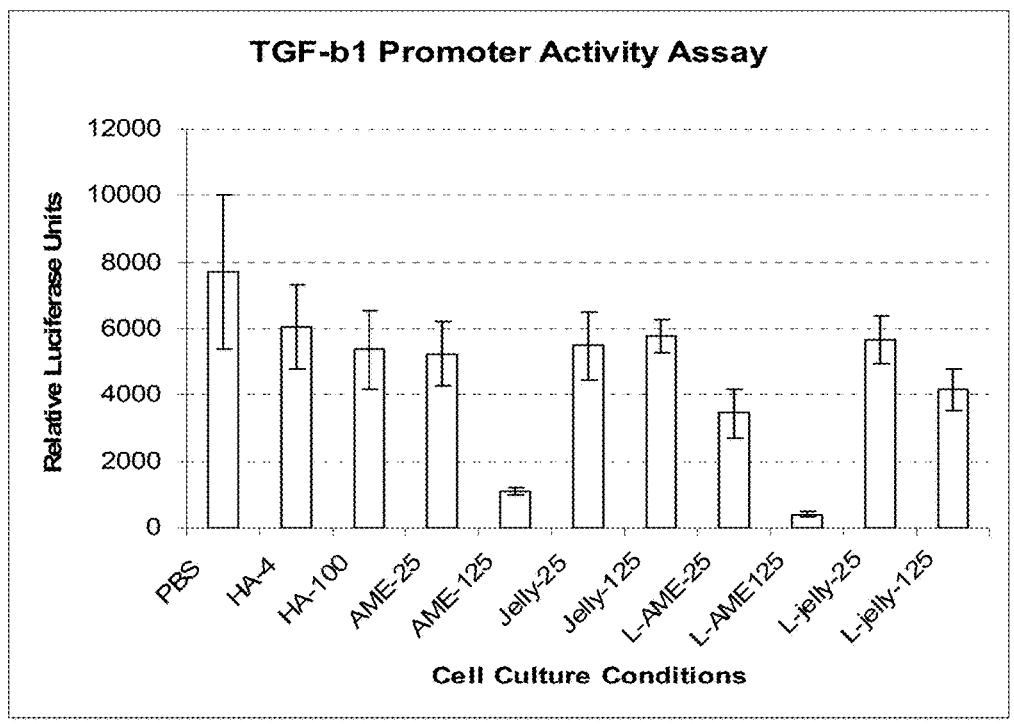
FIG. 7 is a non-limiting example of a bar graph demonstrating the effect of AME (at 25 or 125 μg/ml), with or without lyophilized (L), on the suppression of TGFβ1 activity. The activity is measured in relative luciferase units (RLU).

To examine whether the TGF-beta promoter was suppressed during AME treatment, luciferase assays were performed. Beta-galatosidase assay was used as the transfection control. The result indicated that AME-125, L-AME-25, L-AME-125, L-Jelly-125 showed a significant differences in inhibiting TGF-beta 1 promoter activities, the percentage of inhibitions were 86% ($P<0.01$), 55% ($P<0.1$), 95% ($P<0.01$), and 46% ($P<0.1$), respectively (FIG. 7). The data suggests that lyophilized form of AME or Jelly at a high concentration of 125 µg/ml was more effective than the non-lyophilized AME form. Although the lowest concentration of commercial HA (4 µg/ml) was close to the concentration HA (3.8 µg/ml) in AME/125, the effectiveness suppression in AME/125 is far more potent than HA. (Data not shown) Furthermore, the AME form overall illustrated a better TGF-beta suppression than the Jelly form.

Suppression of TGF-β1 Promoter Activity by AM Extracts Mixed with Collagen Gel or HA A mixture of native type 1 collagen gel and water-soluble AM extract was then prepared. To prepare this mixture, collagen gel was first prepared by diluting a 4 mg/ml stock collagen solution prepared from rat tail tendon (BD Biosciences, San Jose, Calif.) with 0.1 N acetic acid and mixing it with a 1/20 volume ratio of 20×DMEM and 1 N NaOH. A collagen gel formed after incubation at 37° C. Next, water-soluble AM extract (prepared as described herein) was diluted in DMEM to a concentration of 25 µg/ml and then mixed with the collagen gel. The suppressive effect of AM extract mixed in type 1 collagen gel was similar to that of AM extracts (AME) used alone, when compared to the control which was added with BSA alone (FIG. 8, $p<0.01$). Although collagen gel alone (Col) also showed a similar suppressive activity when compared to the plastic control (FIG. 8, $p<0.01$), addition of AME in collagen gel (Col+AME) resulted in further suppression (FIG. 8, $p<0.01$). When water-soluble AM extracts (AME) were mixed in HA gel, the suppressive effect on TGF-β1 promoter activity was better preserved as compared to HA alone (mixed with BSA as a control) (FIG. 5, $p<0.01$) similar to that exerted by AME alone (FIG. 9). Accordingly, an AM extract composition, or its combination with collagen can be useful to suppress TGF-β activity in eye tissue.

Example 2: Characterization of Amniotic Membrane Components

Material and Methods

The concentration of proteins in each extract was quantitated by the BCA Protein Assay Kit (Pierce, Rockford, Ill.). The concentration of hyaluronic acid (HA) in each extracts was assayed with Hyaluronic Acid (HA) Quantitative Test Kit (Corgenix, Westminster, Colo.) based on ELISA using a standard curve provided by the manufacturer prepared by serial dilution of HA.

HA Molecular Weight Range Analysis by Hyaluronidase Digestion

The HA molecular weight ranges of the extracts were analysed by agarose gel electrophoresis according to the method described by Lee and Cowman (Lee H. G. and Cowman, M. K. An Agarose Gel Electrophoretic Method for Analysis of Hyaluronan Molecular Weight Distribution. Analytical Biochemistry, 1994, 219, 278-287). The samples were subjected to 0.5% agarose gel electrophoresis followed by staining using 0.005% Stains-All (Sigma, cat#23096-0) in 50% ethanol. The gel was stained overnight under a light-protective cover at room temperature (Shorter staining periods of 3-4 hr can also give acceptable results). HA was visualized as blue bands after destaining by transferring the gel to H$_2$O and exposed to the room light for approximately 6 hr. The molecular weight standards included lamda DNA-BstE II digested restriction fragments (cat# D9793, Sigma) ranging in MW from 0.9 to 5.7×10$^6$. The authenticity of HA was further verified by incubation of the extract with or without 10 units/ml hyaluronidase (Sigma #H1136) in the reaction buffer (50 mM Tris-HCl, pH7.5, 0.1 M NaCl, 1% Triton X-100, 0.1% BSA supplemented with the above protease and phosphatase inhibitors) for 2 h at 37° C. using a positive control of high MW HA (cat# H1876, Sigma) purified from human umbilical cords.

Western Blot Analyses

The above extracts were electrophoresized on 4-15% denatured acrylamide gels and transferred to the nitrocellulose membrane, and then immunoblotted with a rabbit anti-human inter-α-trypsin inhibitor (rabbit polyclonal antibody (cat# A0301, DAKO at 1:1000), a rabbit anti-human TSG-6 polyclonal antibody (provided by Dr. Tony Day at 1:1000 dilution), a rat monoclonal anti-PTX3 antibody (Alexis Biochemicals, ALX-804-464, 1 μg/ml), an anti-thrombospondin-1 antibody obtained from Calbiochem (Cat# BA24), and a goat anti-human Smad 7 antibody (AF2029, 1:1000, R & D Systems). Imunoreactive protein bands were detected by Western Lighting™Chemiluminesence Reagent (PerkinElmer).

Results

Experiments showed that the observed suppressive effect on the TGF-β1 promoter activity was abolished when water-soluble AM extracts were pre-heated at 90° C. for 10 minutes, suggesting that the responsible component(s) most likely contained protein(s), of which the conformation is important.

Quantitation of HA and Proteins in AM Extracts

The results summarized in the Table below showed that all AM and jelly extracts contained both HA and proteins. In general, the weight ratio between proteins and HA was high in the Total Extract than the supernatant (e.g., L and H for PBS, and A for Buffer A) after centrifugation for AM, suggesting that most protein-containing materials were eliminated by centrifugation. However, this trend was not noted in AM Jelly, suggesting that AM extracts contained more proteins than Jelly (see T under PBS and T under A/B/C). The ratio between proteins and HA was also increased from Extract A to Extracts B and C for both AM and AM jelly, further supporting that HA was mostly present in the soluble form, and vice versa proteins were found more in the water-insoluble components. Furthermore, HA was largely removed from AM Jelly after centrifugation in A/B/C.

TABLE 1

| Tissue | AM | | | | | | | Jelly | | | | | | |
|---|---|---|---|---|---|---|---|---|---|---|---|---|---|---|
| Buffer | PBS | | | A/B/C | | | | PBS | | | A/B/C | | | |
| Fraction | T | L | H | T | A | B | C | T | L | H | T | A | B | C |
| Protein (μg/ml) | 8645 | 1370 | 1467 | 8645 | 2731 | 930 | 2698 | 3836 | 3645 | 3589 | 3836 | 3893 | 527 | 1364 |
| HA (μgml) | 75 | 62 | 44 | 60 | 74 | 7 | 35 | 80 | 90 | 96 | 129 | 94 | 2 | 7 |
| Protein/HA | 115 | 22 | 33 | 144 | 37 | 133 | 77 | 48 | 41 | 37 | 30 | 41 | 264 | 195 |

[Note]:
T: Total, L: the supernatant following the low speed centrifugation of the total extract, H: the supernatant following the low speed centrifugation of the total extract, A, B, C: Extracts, see text.

Figure 10:
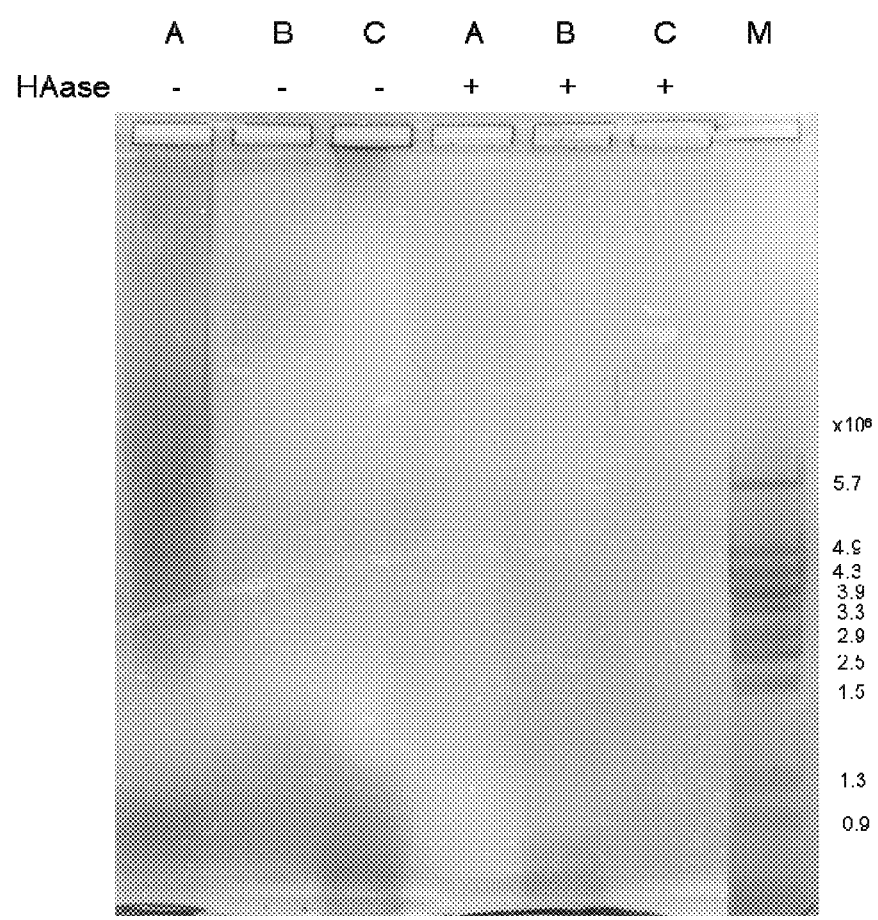
FIG. 10 is a non-limiting example of an analysis of hyaluronan MW Ranges in AM Extracts of various AM extracts, separated by agarose gel electrophoresis. Amniotic membrane extracted by buffer A, B, C were treated with or without hyaluronidase and electrophoretically separated by a 0.5% agarose gel.
Figure 11:
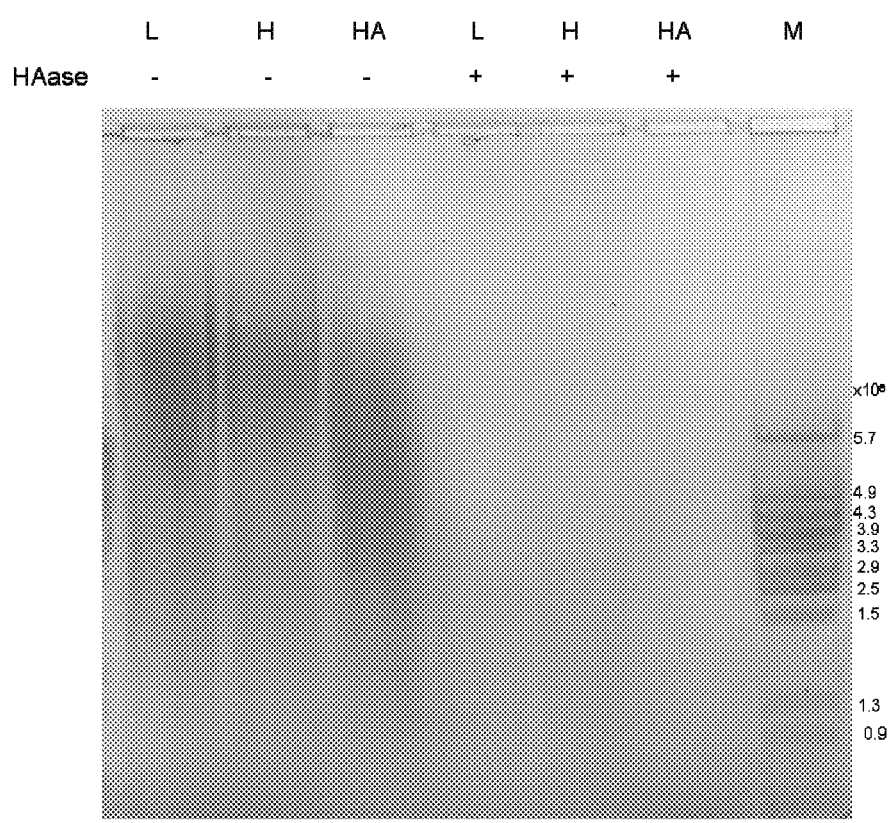
FIG. 11 is a non-limiting example of an analysis of hyaluronan MW Ranges in AM Extracts of various AM extracts, separated by agarose gel electrophoresis. Amniotic membrane extracted by buffer PBS were treated with or without hyaluronidase (10 units/ml in Tris-HCl, pH 7.5, 150 mM NaCl) for 2 hr at 37° C. and run through 0.5% agarose gels. HA: positive hyaluronic acid control; L: AM extract after low speed centrifugation; H: AM extract after high speed centrifugation.

HA in Different AM Extracts have Molecular Weights Greater than One Million Daltons High molecular weight (>10$^6$ daltons) of HA was present in the total extracts and Extract A (FIG. 10). However, even higher MW of HA was present in Extract B, while HA was found in a narrow band with even higher MW in Extract C (FIG. 10). All of the HA-containing components disappeared after hyaluoridase digestion, confirming that they indeed contained HA. Compared to the positive control of HA obtained from Sigma (cat# H1136), a similar high molecular weight (>10$^6$ daltons) of HA was also found in both supernatants obtained after low and high speeds of centrifugation (FIG. 11). Again these HA-containing bands disappeared after hyaluronidase digestion. A similar result was obtained for AM jelly (not shown).

Figure 12:
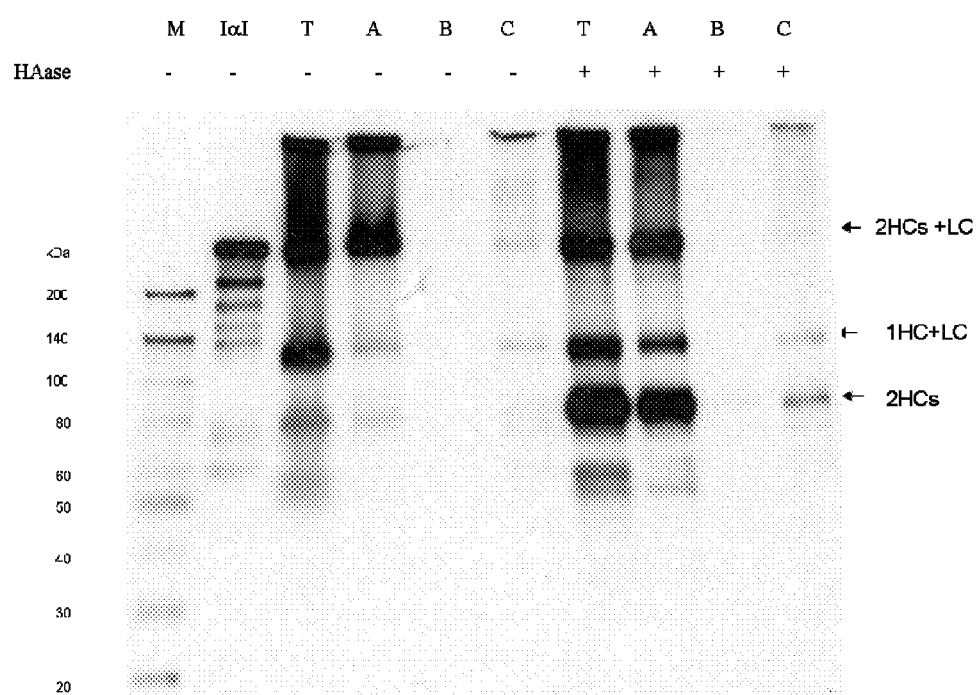
FIG. 12 is a non-limiting example of a photograph of a western blot demonstrating that the inter-α-trypsin inhibitor (IαI) is present in AM Extracts. IαI was present in AM extract A and C although the signal of bikunin was very weak (~39 kDa). Prior to transfer to the western blot, the extract was separated on a 4-15% denatured acrylamide gel.
Figure 13:
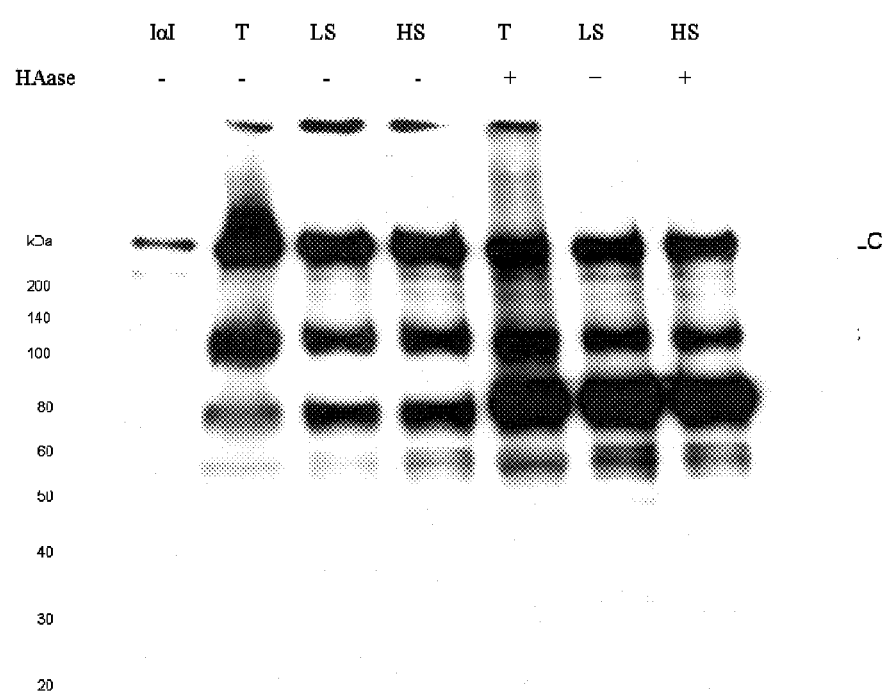
FIG. 13 is a non-limiting example of an immunoblot demonstrating that the inter-α-trypsin inhibitor (IαI) is present in the AM extracts even after low (LS) or high speed (HS) centrifugation.

Inter-α-Trypsin Inhibitor (IαI) is Present in Different AM Extracts and its Heavy Chains (HCs) are Covalently Linked with HA FIG. 12 showed that before digestion with hyaluronidase, free heavy chains were present in different complexes, and a small amount of light chain was also present (UTI or bikunin). However, in all extracts, i.e., total and Extracts A, B, and C, there was also a covalently linked complex between HA and heavy chains of IαI as the latter was released only after hyaluronidase digestion. The same result was obtained in Extracts H and L obtained by two different speeds of centrifugation (FIG. 13).

Tumor Necrosis Factor-Stimulated Gene 6 (TSG-6) is Also Present in AM Extracts

Figure 14:
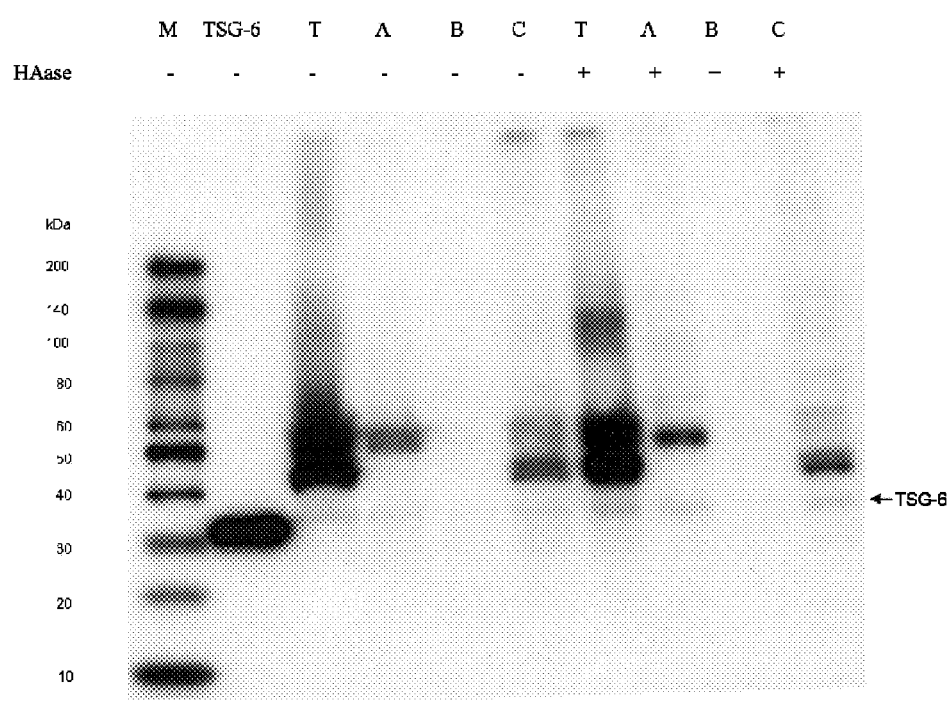
FIG. 14 is a non-limiting example of an immunoblot of TSG-6 (Tumor Necrosis Factor-Stimulated Gene 6), either with (+) or without (−) hyaluronidase treatment. The samples included total AM extract without centrifugation (T), AM Extract after extraction in isotonic low salt buffer (buffer A); high salt buffer (B); or 4 M guanidine HCl (C); as detailed in Example 2. TSG-6 was present in the total extract, buffer A extract, and buffer C extract. The addition of hyaluronidase did not appear to alter the TSG-6 level in the extracts.
Figure 15:
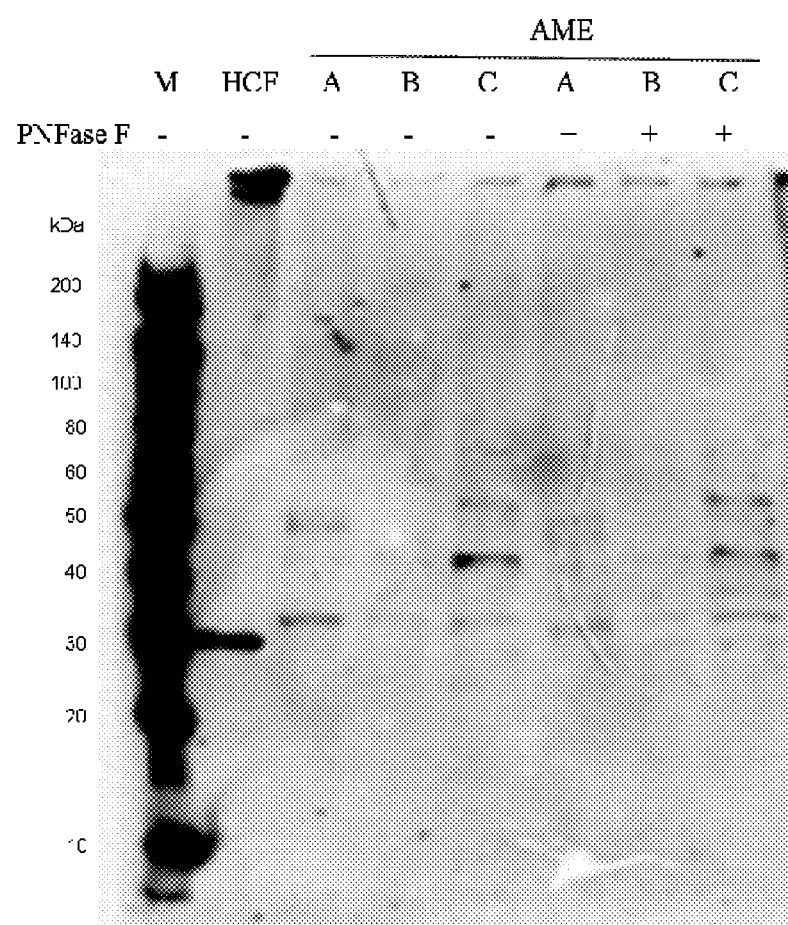
FIG. 15 is a non-limiting example of an immunoblot analysis of the deglycosylation of TSG-6 in AM. AM extract A, B, and C were treated with (+) or without 20 units/ml PNGase F at 37° C. for 3 hours. Glycosylation of TSG-6 in AM was then analyzed by western blot. The cell lysate of human corneal fibroblast (HCF) was used as a positive control.
Figure 16:
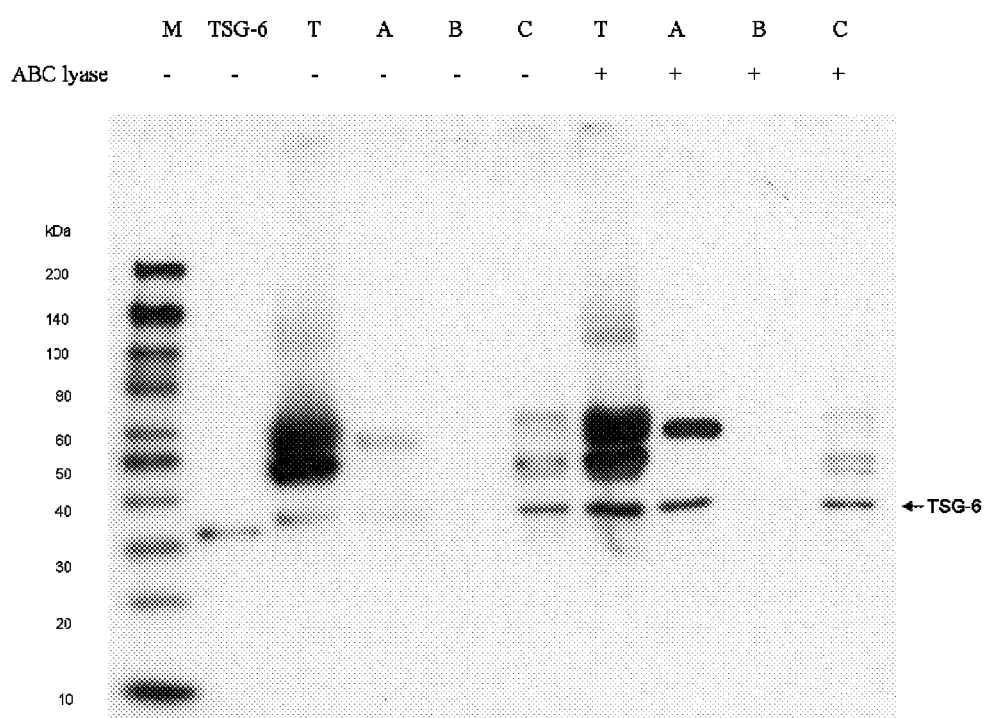
FIG. 16 is a non-limiting example of an immunoblot analysis of potential TSG-6 complexes in AM by digestion with Chondroitin Sulfate ABC lyase. AM extract A, B, and C were treated without (−) or with (+) 1 unit/ml ABC lyase at 37° C. for 2 hours. The possible disruption of TSG-6 complexes was then analyzed by western blot using an anti-TSG-6 antibody RAH-1:1:1000.
Figure 17:
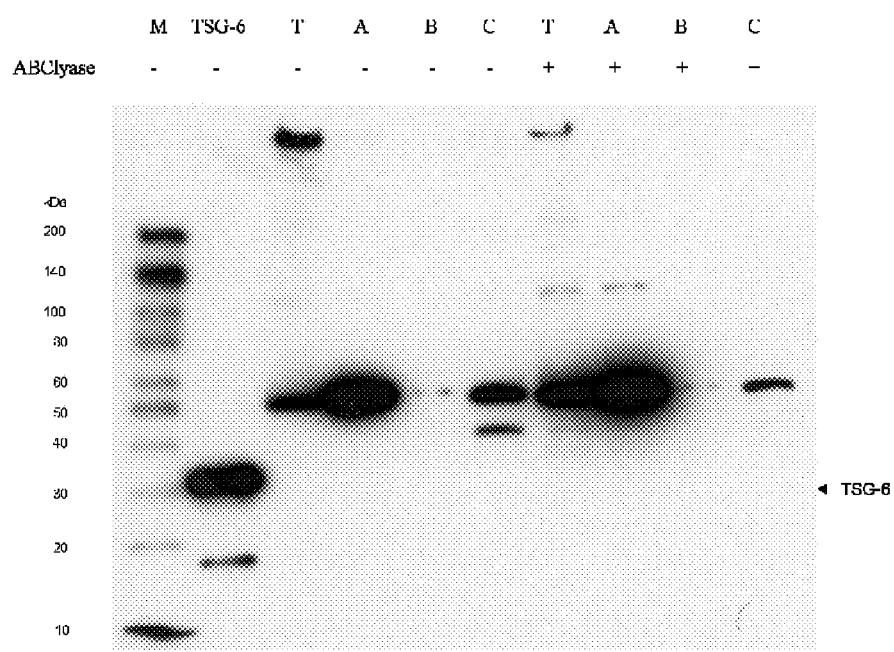
FIG. 17 is a non-limiting example of an immunoblot of potential TSG-6 complexes in AM by digestion with Chondroitin Sulfate ABC lyase. This is the same experiment as shown in FIG. 16 except that a different TSG-6 antibody was used. Here, the anti-TSG-6 antibody was obtained from R & D Systems (cat# MAB2104).

FIG. 14 showed that TSG-6 (~38 kDa) was present in Total, Extract A and Extract C. In Extract A, there was a band of ~38 kDa migrated close to that of the purified TSG-6 (35 kD). The identity of other bands of ~45 and 55 kDa was unknown. Total AM extract (without centrifugation) "T" showed two bands (both above 35 kD), and the higher one (55 kD) that were found in Extract A (after centrifugation), while the lower one (45 kD) was found in Extract C. All of these bands were not significantly altered when samples were treated with hyaluronidase (FIG. 14) or with F-glycosidase (FIG. 15). However, digestion with chondroitin sulfate ABC lyase resulted in more noticeable 38 kD band using antibody RAH-1 (FIG. 16) but not using antibody MAB2104 (FIG. 17).

Figure 18:
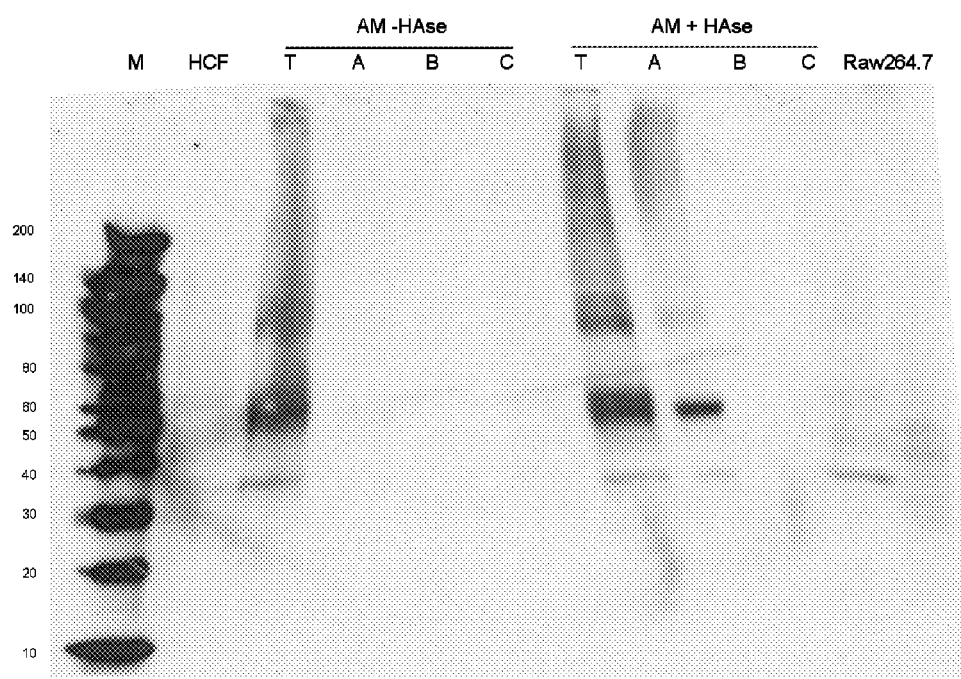
FIG. 18 is a non-limiting example of an immunoblot demonstrating the presence of Pentraxin (PTX3) in AM, using a rat monoclonal anti-PTX3 antibody obtained from Alexis Biochemicals. HCF: human corneal fibroblast, T, A, B, C: AM extract Total, A, B, C, respectively; HAse, Hyaluronidase.

Pentraxin (PTX-3) is Exclusively Present in Water-Soluble AM Extracts and Forms a Complex with HA FIG. 18 showed that PTX3 could also be present in AM extracts and is complexed with HA in the water soluble extract A only.

Thrombospondin (TSP-1) is Present in Different AM Extracts

Figure 19:
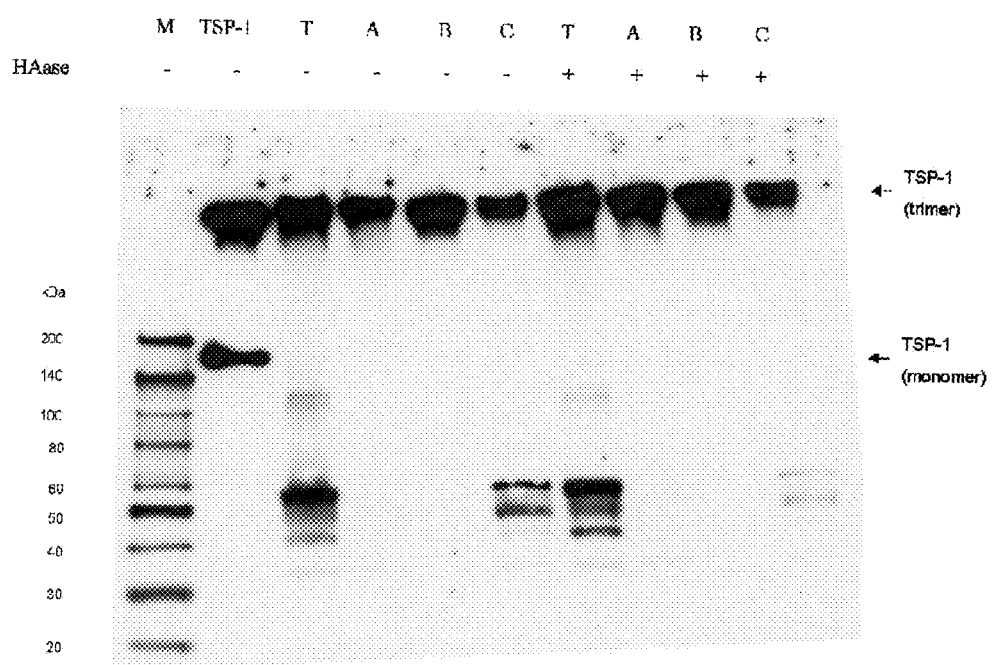
FIG. 19 is a non-limiting example of an immunoblot demonstrating the presence of TSP-1 in AM. The monomeric TSP-1 (180 kDa) and the putative trimeric TSP-1 (540 kDa) are indicated. The positive control, TSP-1, was purified from human platelets (Calbiochem, Cat#605225) and loaded as 100 ng/lane.

FIG. 19 showed that all AM extracts had a high molecular weight band of TSP-1 while the total extract (T) and Extract C also had some bands between 35-120 kDa. Hyaluronidase digestion did not change the reactive pattern except some bands became a little stronger or weaker.

Smad7 is Present in Mostly in Water-Insoluble AM Extracts

Figure 20:
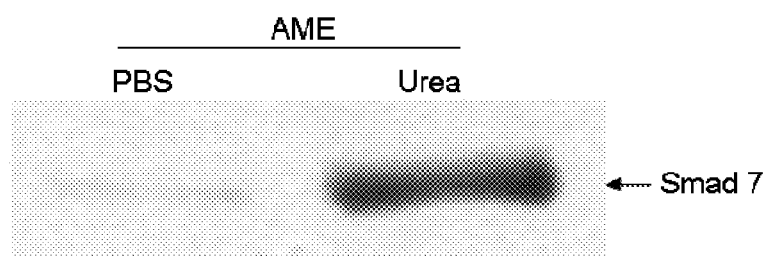
FIG. 20 is a non-limiting example of an immunoblot demonstrating the presence of Smad 7 in AM. AM was extracted with PBS or urea (2M urea in 50 mM Tris-HCl, pH 7.5). 20 µg of total protein was loaded for each extract. Smad 7 was detected with goat anti-human Smad 7 (AF2029, 1:1000, R & D Systems). Smad 7 migrated as a band of ~51 kDa.

Smad 7 was found in both PBS extracts and urea extracts of AM (FIG. 20).

Example 3: Water-Soluble AM Extracts Prevent Cell Death of Corneal Epithelial Cells (Basal Cells and Keratocytes) Induced by Storage and by Injuries Caused by Mechanical and Enzymatic Means Results To demonstrate that AM extracts can prevent apoptosis in injured tissues, the following experiment was performed using a murine model. A total of 22 mouse eye balls were enucleated, two of which were immediately embedded in OCT for frozen sections as a pretreatment control. The remaining of 20 eye balls were subdivided into three subgroups, namely, 1) mechanical scraping (n=8), 2) dispose digestion (enzymatic) (n=6), and 3) without treatment control (n=6). For each group, equal numbers of eye balls were preincubated at 4° C. for 24 h in the presence (+) or absence (−) of 125 µg/ml AM extracts in keratinocyte serum-free medium (KSFM) with defined supplement (Gibco, Carlsbad, Calif.) prior to the treatments. At the end of the first 24 h of incubation in KSFM+/−AM extract (prepared as described herein), 8 eyeballs in Subgroup 1 were then subjected to mechanical scraping with a surgical blade, and were further divided into two groups (n=4 each) and incubated at 37° C. in KSFM+/−AM extract. Six eye balls in Subgroup 2 were subjected to enzymatic digestion with 10 mg/ml Dispase II in KSFM+/−AM extract (n=3 each) for 18 h at 4° C. One eye ball from each group was embedded in OCT for frozen sections. The remaining two eye balls from each group were incubated in KSFM+/−AM extract for another 24 h before analysis. For the non-treatment control (n=6), 3 eye balls each were incubated in KSFM+/−AM extract at 37° C. continuously for two days; one eye ball was removed at the end of the first day while two eye balls were removed at the end of 2 days.

The frozen sections from these eyeballs were subjected to TUNEL staining. In short, terminal deoxyribonucleotidyl transferase-mediated FITC-linked dUTP nick-end DNA labeling (TUNEL) assay was performed using DeadEnd™ fluorometric TUNEL system obtained from Promega (Madison, Wis.) according to the manufacturer's instructions. Sections were fixed in 4% formaldehyde for 20 min at room temperature and permeabilized with 1% Triton X-100. Samples were then incubated for 60 min at 37° C. with exogenous TdT and fluorescein-conjugated dUTP for repair of nicked 3'-hydroxyl DNA ends. Cells were treated with DNase I as the positive control, while the negative control was incubated with buffer lacking rTdT enzyme. The apoptotic nuclei were labeled with green fluorescence, and the nuclei were counterstained with DAPI as red fluorescence.

The water-soluble form of AM extract was prepared by the method for preparing water-soluble AM extract. A BCA assay (Pierce, Rockford, Ill.) was used to quantitate the total protein in the AM extract.

The normal mouse eye ball showed a minimal amount of apoptosis only in the superficial layer of the corneal epithelium of the uninjured control before incubation in KSFM; no apoptosis was noted in the stromal keratocytes. However, after 24 h incubation at 4° C. in KSFM, there was a mild increase of apoptosis in keratocytes of the superficial stroma. Such an increase of keratocyte apoptosis was suppressed by AM extract.

The AM extract was also shown to reduce apoptosis after mechanical damage to the cells. After mechanical scraping, the mouse eye ball showed a significant increase of keratocyte apoptosis. However, incubation with AM extract following mechanical scraping resulted in a decrease in keratocyte apoptosis.

The mouse eyes were also treated enzymatically to damage the cells. Dispase digestion at 4° C. for 18 h in KSFM resulted in a significant amount of apoptosis in not only keratocytes but also in epithelial cells; for the latter apoptosis was found to be present not only in the superficial epithelial cells, but also in the basal epithelial cells. The extent of epithelial and keratocyte apoptosis was far greater than that noted after mechanical scraping. Incubation of AM extract during dispase digestion significantly reduced apoptosis of both epithelial cells and keratocytes. This is significant because dispase treatment mimics the surgical (e.g., excimer ablation in PRK) and pathological insults (e.g., recurrent corneal erosion) that can be directed to the basement membrane. The results of this experiment demonstrate that the application of AM extract to tissues with damaged cells can be used to reduce or prevent cellular damage.

Example 4: Comparing the Relative Potency of Using Collagen or HA as a Vehicle to Deliver Two Different AM Extracts To determine the optimal concentration of the water-soluble and lyophilized forms of AM extracts (prepared by the methods described herein for preparing water-soluble and lyophilized forms of AM extracts, respectively) and compare the relative potency between the two different vehicles containing an appropriate concentration of each form of AM extracts in suppressing TGF-β promoter activity and in promoting macrophage apoptosis, respectively, these two forms of AM extracts are compared by serial dilution in either type I collagen gel or HA and their protein concentrations are monitored accordingly. For type I collagen gel, the protein concentration varies from 0.05 to 2 mg/ml; for HA gel, the concentration varies from 0.05 to 10 mg/ml. These serially diluted solutions or gels of these two forms of AM extracts are pre-coated on plastic dishes before human corneal fibroblasts are seeded or added directly in DMEM with 10% FBS while cells are seeded on the plastic. The anti-scarring effect is measured by assaying the promoter activity of TGF-β1, β2, β3 and RII and comparing the promoter activity to the positive or negative controls where cells are seeded on plastic with or without a given form of AM extracts (without the vehicle), respectively. The positive control, in which cells were seeded on plastic with DMEM plus 10% FBS, showed a high promoter activity. In contrast, the negative control, in which cells were seeded on plastic with DMEM plus 10% FBS but added with 25 µg/ml AM extracts, showed at least 50% reduction of the promoter activity. Based on these control values, the experimental groups using different concentrations of AM extracts mixed in either collagen gel or HA can be measured.

Once the most effective concentration of these two forms of AM extracts in either collagen or HA is determined, the results are verified by repeating the experiment in serum-free DMEM with ITS added with 10 pg/ml to 5 ng/ml TGF-β1. The anti-scarring effect is further correlated with suppression of Smad-mediated signaling by immunocytolocalization of Smads 2, 3 and 4 and α-smooth muscle actin (α-SMA), a marker for myofibroblasts (Gabbiani G., J Pathol. 200:500-503, 2003; Jester and Petroll, Prog Retin Eye Res. 18:311-356, 1999). Another positive control is performed by adding 10 μg/ml neutralizing antibody to all three isoforms of TGF-β. The anti-inflammatory effect is similarly tested in murine macrophages with or without activation by 200 U/ml IFN-γ in DMEM with ITS by measuring the extent of apoptosis using Cell Death Detection ELISAPLUS kit (Roche, Mannheim, Germany), and correlating the data with those obtained by cell morphology, LIVE/DEAD assay (Molecular Probes, Carlsbad, Calif.), Hoechst-33342 nuclear staining, and TUNEL assay (Promega, Madison, Wis.) as recently reported (Li et al., Exp Eye Res. 2005, In Press).

Example 5: Amniotic Membrane Stromal Extract De-Differentiates Myofibroblasts Materials Dulbecco's modified Eagle's medium (DMEM), Hank's balanced salt solution (HBSS), amphotericin B, gentamicin, fetal bovine serum (FBS), 0.25% trypsin/0.53 mM EDTA, Live and Dead cell viability assay reagent, and FITC conjugated phalloidin were purchased from Invitrogen (Carlsbad, Calif.). Bovine serum albumin (BSA), insulin-transferrin-sodium selenite media supplement, formaldehyde, protease inhibitor cocktail, mouse anti-desmin antibody, FITC conjugated anti-mouse, goat, and rat IgG, propidium iodide, and Hoechst-33342 dye were from Sigma (St. Louis, Mo.). Transwell inserts were from Corning Incorporated (Corning, N.Y.). Type I collagen was from BD Biosciences (Bedford, Mass.). BCA™ protein assay kit was from Pierce (Rockford, Ill.). Dispase II and collagenase were from Roche (Penzberg, Germany). Mouse anti-αSMA and Ki67 antibodies were from DakoCytomation (Carpinteria, Calif.). Rabbit anti-vimentin antibody was from Abcam (Cambridge, Mass.). Mouse anti-EDA fibronectin antibody was from Chemicon (Temecula, Calif.). HRP conjugated anti-mouse IgG was from BioRad (Hercules, Calif.). Anti-fade mounting solution was from Vector Laboratories (Burlingame, Calif.). Cryopreserved human AM was obtained from Bio-Tissue (Miami, Fla.).

Cell Cultures

Human tissue was handled according to the Declaration of Helsinki. The fresh human placenta was obtained from Baptist Hospital (Miami, Fla.) after cesarean section after an informed consent was obtained under an IRB-approved protocol. After two times rinse with PBS including gentamicin and amphotericin B, AM was mechanically peeled from the chorion, cut into pieces (~30 mm in diameter), and digested with 10 mg/mL Dispase II in DMEM with 10% FBS at 37° C. for 20 min. After that, the amniotic epithelium was removed by surgical peeling under dissecting microscope, and the remaining stroma was further digested by 2 mg/mL collagenase in DMEM with 10% FBS at 37° C. for 14 h. Cells were collected by centrifuge at 800×g for 5 min, and resuspended and cultured in DMEM with 10% FBS under a humidified atmosphere of 5% $CO_2$ in air at 37° C., the culture medium was changed every two days. AM before enzyme digestion was also embedded in O.C.T for cryosectioning. Human corneoscleral tissues were obtained from the Florida Lions Eye Bank (Miami, Fla.), from which corneal fibroblasts (HCFs) were harvested, and cultured in DMEM containing 10% FBS, secondary passage (P1) cells were used in all experiments.

Preparation of Water-Soluble AM Stromal Extract and AM Inserts

Using aseptic techniques, cryopreserved human AM was briefly washed 2-3 times with HBSS to remove the storage medium. The AM stroma was scraped off by a spatula, frozen in the air phase of liquid nitrogen, and grounded to fine particles by BioPulverizer (Biospec Products, Inc., Bartlesville, Okla.) followed by homogenization on ice with Tissue Tearor (Biospec Products, Inc., Dremel, Wis.) in PBS, pH 7.4, for 1 min. The homogenate was mixed by rotation for 1 h and centrifuged at 14,000×g for 30 min at 4° C. The supernatant in PBS was then collected, and stored in aliquots at −80° C. BCA assay was used to quantitate the protein concentration. This water-soluble protein extract was designated as amniotic stromal extract (ASE). For preparation of AM inserts, AM was thawed immediately before use, washed three times with HBSS, cut into pieces approximately 2.5×2.5 cm in size, and fastened onto a culture insert with the stromal matrix side facing up.

Immunostaining

Cryostat sections (4-μm) of AM were fixed in acetone for 10 min at −20° C.; cultured AMSCs and AM whole mount with AMSCs were fixed in 4% paraformaldehyde for 30 min at 4° C. Sections or cultured cells were rinsed three times for 5 min each with PBS, and then incubated in 0.2% Triton X-100 for 10 min. After three rinses with PBS for 5 min each and preincubation with 2% BSA to block nonspecific staining, sections or cells were incubated with anti-αSMA (1:200), anti-desmin (1:200), and anti-vimentin (1:200) antibodies for 1 h. After three washes with PBS for 15 min, they were incubated with an FITC or Texas Red conjugated secondary antibodies for 45 min. For labeling of F-actin, cells were further stained with FITC conjugated phalloidin at the concentration of 200 units/mL for 15 min. After three additional PBS washes for 15 min each, nuclei were stained with PI (1:2000) for 1 min or Hoechst-33342 for 15 min, then analyzed with a fluorescence microscope. For immunohistochemical staining of Ki67, endogenous peroxidase activity was blocked by 0.6% hydrogen peroxide for 10 min. Nonspecific staining was blocked by 1% normal goat serum for 30 min. Cells were then incubated with anti-Ki67 antibody (1:50) for 1 h. After three washes with PBS for 15 min each, cells were incubated with biotinylated rabbit anti-mouse IgG (1:100) for 30 min, followed by incubation with ABC reagent for 30 min. The reaction product was developed with DAB for 5 min, and examined under a light microscope.

Western Blot Analysis

Cultured AMSCs or myofibroblasts from plastic, collagen, or AM surface were collected and extracted in cold RIPA buffer [50 mM Tris.Cl, pH 7.5, 150 mM NaCl, 1% Nonidet P-40, 0.5% sodium deoxycholate, 0.1% SDS, and protease inhibitor cocktail]. Equal amounts of proteins extracted from lysates were separated on 4%-15% sodium dodecyl sulphate-polyacrylamide gels (SDS-PAGE), and then electrophorectically transferred to nitrocellulose membranes. After 1 h of blocking in 5% nonfat milk, the blots were incubated with primary antibodies to αSMA and ED-A fibronectin using α-actin as a loading control. The specific binding was detected by anti-mouse or anti-rabbit horseradish peroxidase (HRP)-conjugated antibodies, and visualized by enhanced chemiluminescence method.

Statistical Analysis

All experiments described above were repeated three times, each in triplicate or more. Group means were compared using the appropriate version of Student's unpaired t-test. Test results were reported as two-tailed p values, where p<0.05 was considered statistically significant. Summary data are reported as means±S.D.

Results

The In Vivo Phenotype of AMSCs

Figure 21:
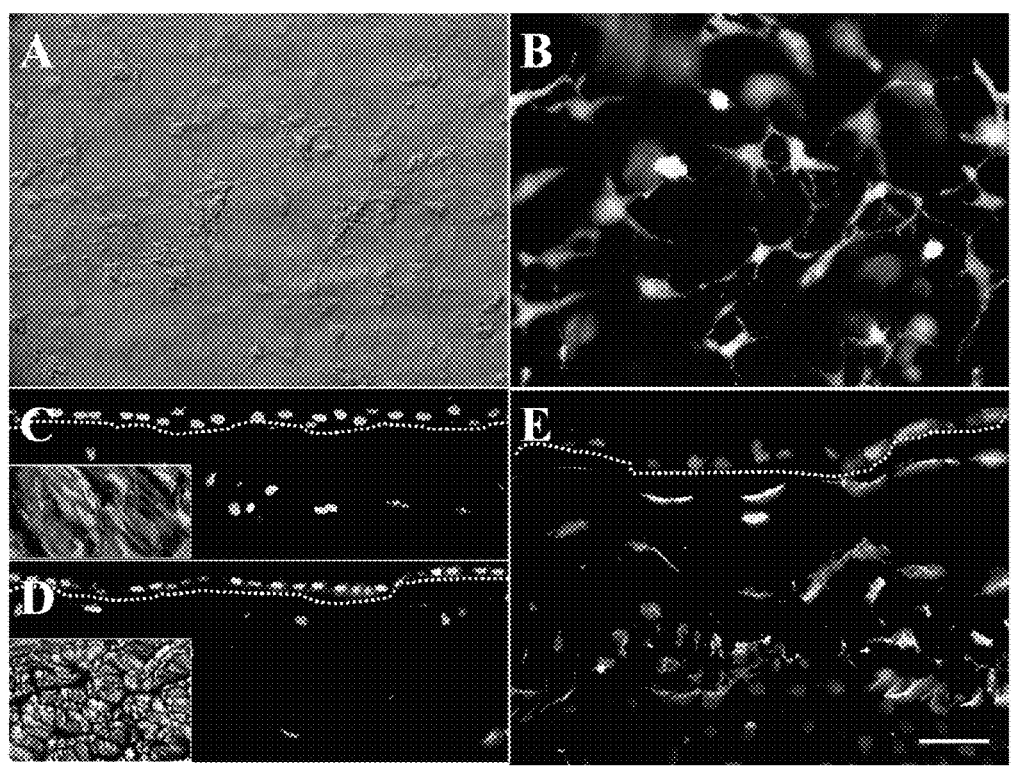
FIG. 21 a non-limiting example of microscopic images of amniotic membrane stromal cells (AMSC) in AM. A: AMSCs exhibited dendritic morphology and maintained intercellular contacts in situ. B: Staining with Live and Dead assay for cell viability. The dendritic morphology and intercellular contacts were better visualized by this method. C: AMSCs did not express α-SMA. D: AMSCs did not express desmin. In contrast, as a positive control, umbilical cord mesenchymal cells showed strong staining to both α-SMA and desmin (insert of C and D, respectively). E: All AMSCs expressed vimentin. Dotted lines indicate the separation between the AM epithelium and AM stromal layers. Nuclear counterstaining was performed by DAPI (C, D) and PI (E), respectively. Bar represents 50 µm.

After removal of amniotic epithelial cells by Dispase II, AMSCs in AM could be observed in situ. Through a phase contrast microscope, they exhibited a dendritic morphology and maintained intercellular contacts via thin processes (FIG. 21A). Cell viability, the dendritic morphology and intercellular contacts were better visualized by staining with Live and Dead assay (FIG. 21B). Immunostaining of AM cross-sections showed that AMSCs did not express α-SMA (FIG. 21C) and desmin (FIG. 21D). In contrast, as a positive control, umbilical cord mesenchymal cells showed strong staining to both α-SMA and desmin (see the inset of FIGS. 21C and 21D, respectively). However, all AMSCs expressed vimentin (FIG. 21E). These data collectively indicated that AMSCs are of a fibroblast phenotype in vivo.

Rapid Myofibroblast Differentiation of AMSCs In Vitro

To investigate the differentiation of AMSCs in vitro, collagenase-isolated AMSCs were plated on plastic dishes and cultured in DMEM with 10% FBS at a density of 200 cells/mm$^2$. Within 4 to 5 days, cells adopted a typical fibroblast cell shape (FIG. 22A) and remained α-SMA negative (FIG. 22E). However, some cells started to increase the cell size, change the shape (FIG. 22B), and express α-SMA (FIG. 22F) at the end of 1 week of culturing. After subcultured to another plastic dishes in the same medium, the majority of cells exhibited a typical myofibroblastic cell shape at the end of one week of the passage one (FIG. 22C), and eventually almost all cells turned into a myofibroblastic shape and had prominent microfilaments at the end of one week of the second passage (FIG. 22D). Accordingly, α-SMA-positive myofibroblasts dramatically increased from 71.9±3.7% at 1 week primary culture to 93.9±4.1% at passage one culture and 98.5±1.7% at passage two culture (FIG. 22I). Nevertheless, expression of desmin was still negative at the passage two culture (data not shown). Western blot analysis revealed that AMSCs in vivo weakly expressed ED-A fibronectin but did not express α-SMA. However, α-SMA and ED-A fibronectin expression dramatically increased at the end of the primary culture and maintained at the passage 2 (FIG. 22J). These results indicated that AMSCs rapidly differentiated into myofibroblasts on plastic in this serum-containing medium.

Differentiated Myofibroblasts from AMSCs could be Reversed if Subcultured on AM Stromal Matrix In our previous studies, we have shown that AM can inhibit myofibroblast differentiation of human or mouse keratocytes when cultured on the stromal matrix of AM from the primary culture. To further investigate whether AM stromal matrix was also potent in modulating the phenotype of differentiated myofibroblasts or not, myofibroblasts differentiated from AMSCs at passage 2 were subcultured onto the stromal matrix of AM, and compared to those subcultured on collagen I-coated dish as a control. After 7 days of cultivation in DMEM with 10% FBS, AMSCs on collagen I still maintained a myofibroblastic shape (FIG. 23A). In contrast, cells seeded on AM stromal matrix exhibited a mixture of round, spindle, elongated, and dendritic shapes (FIG. 23B). Live and Dead assay confirmed that cells on both collagen I (FIG. 23C) and AM matrix (FIG. 23D) remained 100% viability, but revealed a significant difference in the cell shape. Immunostaining to phalloidin showed vivid stress fibers (FIG. 23E), which also contained strong α-SMA expression (FIG. 23G) in myofibroblasts seeded on collagen I. In contrast, the phalloidin staining became weak and spotty (FIG. 23F), and α-SMA staining became obscured while cells were seeded on AM stromal matrix (FIG. 23H). Western blot analysis confirmed that myofibroblasts derived from AMSCs continuously expressed abundant amounts of ED-A fibronectin and α-SMA when seeded on type I collagen (FIG. 23I). In contrast, expression of ED-A fibronectin was decreased and that of α-SMA became undetectable when seeded on AM stromal matrix (FIG. 23I). These results collectively indicated that myofibroblasts differentiated from AMSCs could still be reversed to a fibroblast phenotype when subcultured on the AM stromal matrix.

Amniotic Stromal Extract Prevented Myofibroblast Differentiation of AMSCs and Reverse Differentiated Myofibroblasts To further investigate whether the aforementioned reversal activity by the AM stromal matrix was retained in the water-soluble AM stromal extracts, primary AMSCs (P0) were cultured on plastic in DMEM containing 10% FBS with or without 100 μg/ml ASE. The results showed that AMSCs maintained a spindle fibroblastic shape after 4 days of cultivation with or without ASE (FIGS. 24A and 24B, respectively). However, at that time, cells already expressed α-SMA without ASE (FIG. 24E), but remained devoid of α-SMA expression when ASE was added (FIG. 24F). When cultures were extended to 10 days, as shown in FIG. 2, AMSCs showed an enlarged cell shape, and vividly expressed phalloidin-positive stress fibers (FIG. 24C) containing positive expression of α-SMA (FIG. 24G). Strikingly, AMSCs aggregated into spheres of varying sizes with a smaller nucleus in the presence of ASE (FIG. 24D). These cells in the sphere remained viable based on the Live and Dead assay (data not shown). Some spheres were detached from the plastic dish, but they could reattach to a new plastic dish to generate new growth of myofibroblasts when switched back to DMEM/10% FBS (data not shown). Phalloidin staining did not show any stress fiber (FIG. 24D), while α-SMA expression in the sphere was weak (FIG. 24H). These results indicated that ASE indeed could prevent myofibroblast differentiation of AMSCs.

To examine whether the aforementioned reversal activity of AM stromal matrix was retained in ASE, we added 100 μg/ml ASE for 1 week to passage 2 AMSCs cultures on plastic containing DMEM with 10% FBS. As described earlier (FIG. 22), by this time nearly all cells turned into myofibroblasts with a squamous morphology, prominent stress fibers and strong expression of α-SMA. Addition of ASE allowed cells to be reverted to an elongated or spindle shape (FIG. 25A) with a significant decrease of α-SMA expression (FIG. 25B). Western blot analysis further confirmed decrease of EDA fibronectin and α-SMA expression after the addition of ASE (FIG. 25C). These results indicated that AM stroma contained soluble factor(s) that could suppress myofibroblast differentiation of AMSCs if added before, but could reverse differentiated myofibroblasts to fibroblasts if added later.

Reversal of Myofibroblasts was not Associated with Cell Proliferation

Figures 26A, 26B, 26C, 26D:
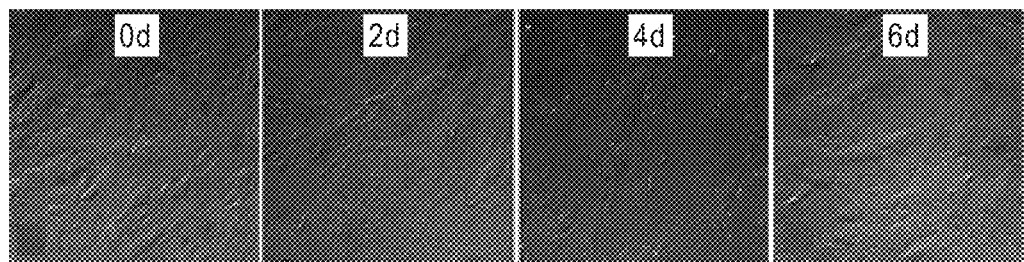
FIGS. 26A through 26L are non-limiting examples of microscopic images demonstrating that the reversal of myofibroblasts by ASE was not associated with cell proliferation. AMSCs (passage 2) were cultured in DMEM/ITS without (A, B, C, D) or with ASE (E, F, G, H) for 0, 2, 4, or 6 days as indicated. α-SMA-expressing stress fibers were gradually decreased from day 0 to day 6 after addition of ASE (I, J, K, L), and correlated with morphological changes (E to H).
Figures 26E, 26F, 26G, 26H:
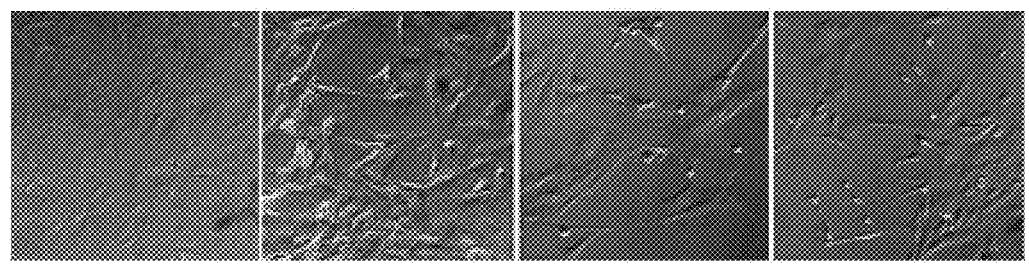
Figures 26I, 26J, 26K, 26L:
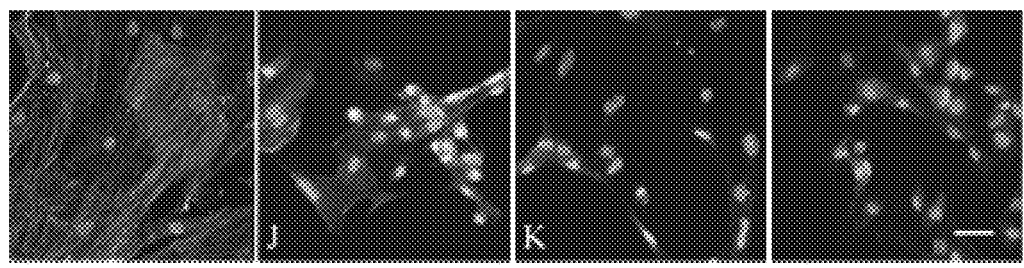

To further determine whether the aforementioned phenotypic reversal of AMSCs from myofibroblasts to fibroblasts by ASE was accompanied by cellular proliferation or not, we switched the medium from DMEM plus 10% FBS to serum-free DMEM/ITS in passage 3 cultures, in which as described in FIG. 2 nearly all cells turned into myofibroblasts. During a course of 6 days of observation, cells in the control culture maintained the same myofibroblast morphology with prominent stress fibers in the cytoplasm (FIG. 26A to 26D). However, cells in the experimental cultures with addition of ASE gradually changed the shape from being large and flattened on day 0 (FIG. 26E) to spindle and elongated on day 2 and day 4 (FIGS. 26F and 26G, respectively), and finally some cells shrank to a small size on day 6 (FIG. 26H). Such a dramatic morphological change caused by addition of ASE was accompanied by the loss of α-SMA-expressing stress fibers (FIGS. 26I to 26L). Ki67 staining confirmed that myofibroblasts in DMEM/ITS of P3 cultures did not exhibit any cellular proliferation no matter if ASE was added or not (FIGS. 26M and 26N, respectively). As a control, AMSCs in P1 cultures showed occasional Ki67-positive nuclei when cultured on plastic in DMEM/10% FBS (FIG. 26O), while many human corneal fibroblasts cultured on plastic in DMEM/10% FBS showed Ki67-positive nuclei (FIG. 26P). These results strongly supported the notion that ASE not only prevented myofibroblast differentiation of AMSCs, but also reversed differentiated myofibroblasts of AMSCs to fibroblast without affecting their cellular proliferation.

Differences of Morphology and Stead Signaling and Suppression of TGF-β Promoter Activity by AM Stromal Matrix Mouse stromal cells freshly isolated by collagenase exhibited a fibroblastic morphology when cultured on plastic in DMEM with 10% FBS, but a dendritic morphology when cultured on AM stromal matrix in the same medium. Immunostaining showed nuclear exclusion of Smad4 for dendritic keratocytes cultured on AM in DMEM with ITS even after being challenged with 10 ng/ml TGF-β1. In contrast, an increasing percentage of cells from 13% when cultured on plastic to 67% and 85% after 10 ng/ml TGF-β1 was added for 3 hours and 5 days, respectively. These results suggest that AM stromal matrix suppresses Smad-mediated T-TGF-β signaling, which helps maintain the keratocyte phenotype.

Mouse corneal fibroblasts cultured on plastic and intact cryopreserved AM (prepared as described herein for preparing cryopreserved intact AM) were cotransfected with TGF-β2 promoter-luciferase plus CMV-β-galactosidase or TGF-βRII promoter-luciferase plus CMV-β-galactosidase for 48 hours. Cell extracts were assayed for both activities of luciferase and β-galactosidase. The relative luciferase unit of the promoter activity of TGF-β2 and TGF-βRII was suppressed in cells cultured on AM.

Example 6: AM Extracts Suppress Fibroblast Migration from Human Limbal Explants

Materials and Methods
Preparation of Total Soluble Human Amniotic Membrane Extracts in PBS The entire procedure for preparation of total soluble human AM extracts (T) was carried out aseptically so as to be used for subsequent cell culture-based experiments. Frozen human placenta was obtained from Bio-tissue, Inc. (Miami, Fla.), from which AM was retrieved. AM was sliced into small pieces to fit into the barrel of a BioPulverizer (Biospec Products, Inc., Bartlesville, Okla.), frozen in the liquid nitrogen, and then pulverized into a fine powder. The powder was weighed and mixed with cold PBS buffer (prepared by adding distilled $H_2O$ to 1×PBS, pH7.4, from 10×PBS, cat#70011-044, Invitrogen, Carlsbad, Calif.) with protease inhibitors (protease inhibitor cocktail, P8340, Sigma, and supplemented with 1 mM PMSF) and phosphatase inhibitors (50 mM sodium fluoride and 0.2 mM sodium vanadate) at 1:1 (ml/g). The mixture was kept in the ice and homogenized with a Tissue Tearor (Biospec Products, Inc., Dremel, Wis.) for 5 times, 1 min each with a 2 min interval cooling. This water-soluble extract was designated as "Total" (T). The total water-soluble extract was mixed for 1 hr at 4° C., centrifuged at 4° C. for 30 min at 48000×g. The supernatant was divided into aliquots and stored at −80° C.

Human Corneolimbal Explant Cultures

Human tissue was handled according to the Tenets of the Declaration of Helsinki. Limbal rims were obtained either from the donor corneas (Medical Eye Bank of Florida, Orlando, Fla.) or after transplantation of donor corneas (Florida Lions Eye Bank, Miami, Fla.). The excessive sclera, iris, corneal endothelium, conjunctiva, and Tenon's capsule were removed, and the remaining rims were briefly rinsed 3 times with SHEM media made of an equal volume mixture of HEPES-buffered DMEM and Ham's F12 supplemented with 5% FBS, 0.5% DMSO, 2 ng/ml mouse EGF, 5 μg/ml insulin, 5 μg/ml transferrin, 5 ng/ml selenium, 0.5 μg/ml hydrocortisone, 10 nM cholera toxin, 50 μg/ml gentamicin, 1.25 μg/ml amphotericin B. Each limbal rim was equally divided into two halves and each half was further equally subdivided into 6 explants, i.e., to make 12 explants per limbal rim. To eliminate variations of age, sex, and race, explants from the corresponding position of the same donor cornea were selected for the control and the experimental group, respectively. An explant was placed on the center of each 6 well with the epithelial side up and cultured in SHEM or SHEM with 25 μm/ml the above total AM extract. The culture was maintained at 37° C. under 95% humidity and 5% $CO_2$, the medium was changed every other day, and their outgrowth was monitored daily for 14 days using an inverted phase microscope (Nikon, Japan). The outgrowth area was digitized every other day by Adobe Photoshop 5.5 and analyzed by NIH ImageJ 1.30v (NIH, Bethesda, Md.)

MTT Assay

The MTT assay (Cell Proliferation Kit I, cat#11465007001, Roche Applied Science, Indianapolis, Ind.) is a colorimetric assay based on the cleavage of the yellow tetrazolium salt MTT to purple formazan crystals by metabolic active cells. The outgrowing cells from human limbal explants cultured in SHEM (the Ctrl group) or SHEM with 25 μg/ml AME (the AME group) for 14 days were harvested separately by trypsin/EDTA digestion and resuspended into SHEM medium. Cells were counted with hemacytometer and seeded at 2000 cells/per 96 well with 100 μl medium. Each group was further divided into 3 subgroups (Ctrl, PBS, AME) in which no supplement, 2 μl of PBS, or 2 μl of 1250 μg/ml AME (to make a final concentration of 25 μg/ml AME) was added immediately after the cell seeding. Each subgroup had a total of 16 wells (from the duplicate). Cells were incubated at 37° C. under 95% humidity and 5% $CO_2$ for 10 days with the medium being changed every other day. When MTT assay was performed, 10 μl of the MTT labeling reagent (final concentration 0.5 mg/ml) was added to each 96 well. The 96 well plates were incubated for 4 hr under the same culture conditions. Then 100 μl of the Solubilization solution was added to each well and the plate was further incubated at the same condition for 20 hr. The spectrophotometrical absorbance of samples was measured using a microplate reader (Fusion™, Meriden, Conn.) with a wavelength of 550 nm minus the absorbance of a reference wavelength at 650 nm.

Hematoxylin and Eosin (H & E) Staining

After cultured for 14 days, explants were removed from wells and embedded with OCT (Tissue-Tek), briefly frozen in liquid nitrogen, and stored at −80° C. Tissues were sectioned with Microtome Plus (Triangle Biomedical Sciences, Durham, N.C.) at 6 µm on snowcoat X-Tra™ microslides (Surgipath, Richmond, Ill.), fixed in 10% formalin for 10 min, and sequentially stained with Harris hematoxylin for 5 min, 1% Eosin yellowish for 1 min at 25° C. Tissues were dehydralated with a series of 70%, 95%, and 100% alcohol, each for at least 5 min, and finally treated in xylene (SUB-X™ Xylene Substitute, Surgipath) and mounted with a cover slip. The slides were observed under an inverted microscopy (ECLIPSE, TE 2000-U, Nikon).

Results

AM Extract Slowed Down Epithelial Migration from Human Limbal Explants and Resulted in Less Epithelial Cells in the Outgrowth but with More Progenitor Cells The Table shown below indicates that the onset of epithelial outgrowth from the limbal explant was delayed and the resultant epithelial outgrowth contained less cells in cultures added with AM extracts.

TABLE 2

Explant Outgrowth

| Outgrowth | Explant (6) SHEM/PL | Explant (6) SHEM/AME/PL 25 µg/ml |
|---|---|---|
| Day 3 | 2 | 0 |
| Day 4 | 6 | 1 |
| Day 5 | 6 | 6 |
| Day 14 (cells from 4 explants) | $7.35 \times 10^6$ (3.6) | $2.05 \times 10^6$ (1.0) |

Figures 27A, 27B:
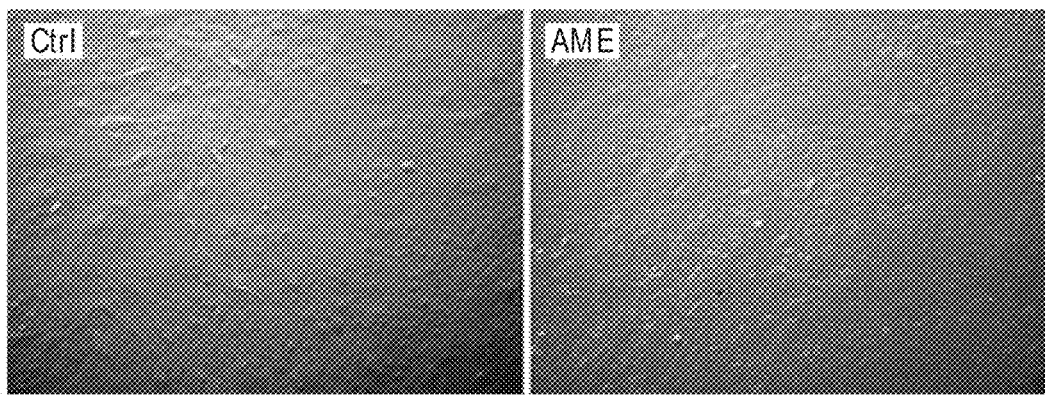
FIGS. 27A through 27D are non-limiting examples of microscopic images demonstrating that AM extract suppressed fibroblast migration from human limbal explants and resulted in less fibroblasts in the outgrowth. A, B: The outgrowth from human limbal explants cultured in both SHEM (Ctrl) and SHEM/AME (AME). C, D: After 14 days in culture, human limbal explants were removed from culture wells, embedded, sectioned, and stained with Hematoxylin and Eosin staining.
Figures 27C, 27D:
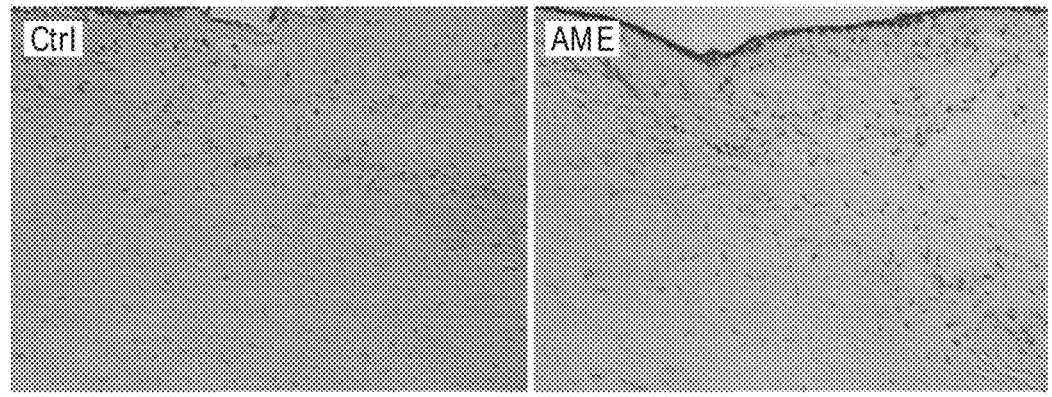

AM Extract Suppressed Fibroblast Migration from Human Limbal Explants and Resulted in Less Fibroblasts in the Outgrowth In FIG. 27A, the outgrowth from human limbal explants cultured in both SHEM (Ctrl) and SHEM/AME (AME) formed a similar epithelial sheet. However, some fibroblast-like cells only appeared in Ctrl but not in AME culture, indicating AME may suppress the migration of fibroblasts. In FIG. 27B, after 14 days culture, human limbal explants were removed from culture wells, embedded, sectioned, and stained with H & E. There were much more stromal cells in the AME than those in the Ctrl. This is possibly caused by AME suppressing the migration of fibroblasts.

Suppression of Fibroblast Outgrowth by AME

Figure 28A:
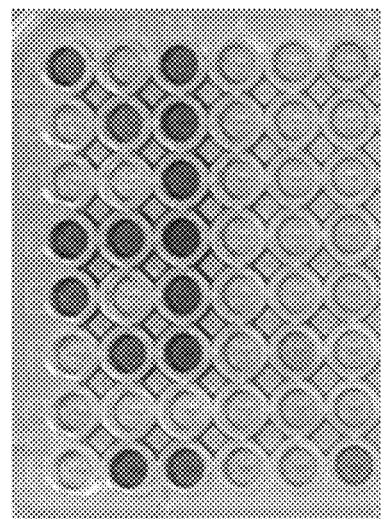
FIG. 28A is a non-limiting example of a photograph of a 48 well assay plate demonstrating the suppression of fibroblast outgrowth by AME. A. The outgrowth from human limbal explants after 14 days of growth in either SHEM (Ctrl) and SHEM with 25 μg/ml AME (AME) was separately harvested and seeded in each 96 well at 2000 cells/well. Cells from the Ctrl were seeded in columns 1-3 (1: Ctrl; 2: PBS; 3: AME; and those from the AME were seeded in columns 4-6 (1: Ctrl; 2: PBS; 3: AME. An MTT assay was performed after 10 days of culture.
Figure 28B:
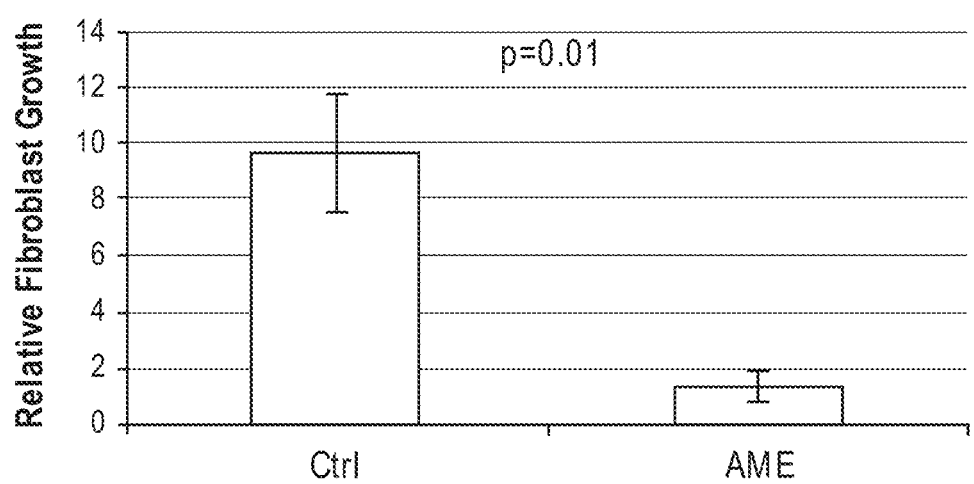
FIG. 28B is a non-limiting example of a bar graph showing the quantitation and statistical analysis of the relative suppression of fibroblast outgrowth by AME.
Figures 29A, 29B:
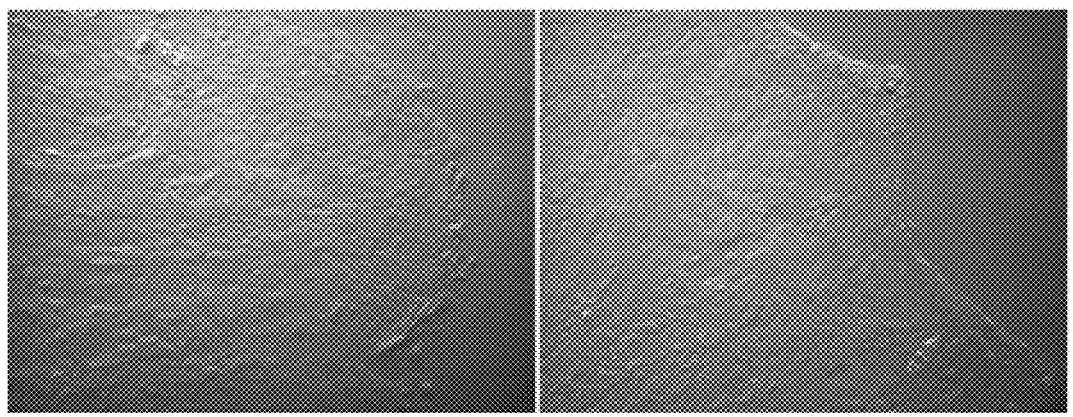
FIGS. 29A and 29B are non-limiting examples of microscopic images of the outgrowth from human limbal explants cultured in both SHEM control (FIG. 29A) and SHEM with AME (FIG. 29B) for 14 days.

The outgrowth from human limbal explants cultured in both SHEM (Ctrl) and SHEM/AME (AME) for 14 days were separately harvested and seeded in each 96 well at 2000 cells/well as described in MTT Assay. Cells from the Ctrl were seeded in columns 1-3 (1: Ctrl; 2: PBS; 3: AME; n=8 for one plate shown here but n=16 for the duplicate with the similar result) and those from the AME were in columns 4-6 (1: Ctrl; 2: PBS; 3: AME). After cultured 10 days, cells were used for MTT assay. There was no significant difference of fibroblast growth among subgroups (Ctrl, PBS, and AME) but there was statistically significant difference of fibroblast growth between cells derived from outgrowth in SHEM and in SHEM/AME (FIG. 28A). Because fibroblasts grew much quickly than epithelial cells did so wells became pink after adding MTT reagents contained fibroblasts. Statistical analysis of the fibroblast growth in Ctrl and AME showed AME significantly suppressed the fibroblast growth (p=0.01) (FIG. 28B).

More Clonal Growth from Outgrowth Epithelial Cells Cultured in SHEM/AME than Those from Cultured with SHEM Only Human limbal explants were cultured in either SHEM only (Ctrl) or SHEM/AME (100 µg/ml). After cultured for 10 days, outgrowing epithelia cells were harvested with trypsin/EDTA and counted again, the growth of epithelial cells were significantly suppressed by AME. That is, total cells from 3 explants cultured in SHEM is $9 \times 10^5$ while total cells from 3 explants cultured in SHEM/AME is $2.3 \times 10^5$, ratio is Ctrl/AME=3.9. When these cells were seeded at 500 or 1000 cells in each 60 mm dish (~18 or 36 cell/cm$^2$) on a swiss 3T3 feeder layer with MMC pre-treatment (4 µg/ml for 2 hr at 37° C.) in SHEM medium. After seeding for 4-5 days, epithelial clones started to form. Clones from cells cultured previously with SHEM/AME were more and larger than those cultured previously with SHEM only (P<0.05). Clones were allowed to grow until day 10 and then clones were stained with the crystal violet dye to show the number and size of clones.

AME Inhibited MAPKp38 of the Outgrowth

The outgrowth from human limbal explants cultured in both SHEM (Ctrl) and SHEM/AME (AME) for 14 days formed a similar epithelial sheet. However, the edges of epithelial sheets were different: the edge of the Ctrl epithelial sheet appeared rough while that of the AME was smooth (FIG. 29, Ctrl—left panel; AME—right panel). This phenomenon resembled the effect of MAPK p38 inhibitor (10 µM SB203580 in SHEM) on the outgrowth of human limbal explants (data not shown). It provided another evidences that AME contained component(s) that can inhibit MAPK p38.

Example 7: Skin Lotion Composition Containing AM Extract

A skin lotion is prepared by the following method. 0.25 g methyl hydroxybenzoate and 7.5 g glycerin are dissolved in 75 ml of water at 150° F. 0.7 g sorbitan monolaurate, 0.7 g polysorbate 20, and 1.0 g cetostearyl alcohol are melted at 150° F. and are then compounded into the solution. The mixture is allowed to cool while mixing. When the mixture reaches a temperature below approximately 90° F., 4 ml of AM preparations and purified compositions described herein is added while mixing. A trace amount of fragrance is also added while mixing. The lotion is packaged into 10 ml aliquots and stored at room temperature.

Example 8: Ophthalmic Solution Composition and Treatment of an Eye Disease

An ophthalmic eye drop solution is prepared by mixing 100 mg of ground, lyophilized AM extract with 0.9 g of NaCl in 100 mL of purified water and filtered using a 0.2 micron filter. The resulting isotonic solution is then incorporated into ophthalmic delivery units, such as eye drop containers, which are suitable for ophthalmic administration. Two drops of the composition is applied to a burn-damaged eye 4 times per day. By use of this method, the eye returns to normal health.

Example 9: Eye Ointment Composition and Treatment of Eye Disease Using Same

A sterile eye ointment composition is prepared by compounding 90 grams white petrolatum, 10 grams liquid petrolatum, and 0.5 grams lyophilized AM powder. The mixture is pasteurized and packaged into individual tube containers of 2.0 g each.

To treat an eye disease using the composition, an aliquot of approximately 0.1 g is gently applied directly from the tube to the inner edge of the bottom eye lid. The ointment is applied 4 times per day. The patient progress is monitored every other week by an opthamologist. By use of this method, the eye disease improves.

Example 10: Treatment of Human Eye Disease Using AM Preparation

An individual with burn damage to the eye is identified. A preparation of 1% AM, 0.5% collagen in DMEM is prepared. The individual is treated 4× per day with 2 drops of the composition. By use of this method, the eye damage improves as compared to a non-treated burn damaged eye.

Example 11: Treatment of Human Skin Disease Using AM Preparation

An individual with psoriasis is identified. The individual is treated with a 5% preparation of reconstituted AM, supplemented with 1 mg/ml purified Smad7 derived from a commercial source. The formulation is dissolved in a lotion composition. The treatment is administered 2 times per day. By use of this method, the psoriasis is alleviated or disappears.

Example 12: Rectal Gel Composition Containing AM Extract

A rectal gel composition is prepared by combining 100 mg of commercially available HA and TSG-6 (purified) with 5 ml sterile AM extract prepared from frozen AM membrane material as described in Example 1. To this mixture is added 2.5 g of methylcelluose (1500 mPa), 100 mg of methylparapen, 5 g of glycerin and 95 mL of purified water. The resulting gel mixture is then incorporated into rectal delivery units, such as syringes, which are suitable for rectal administration.

What is claimed is:

1. A method of preventing or reversing scar formation in a subject in need thereof, comprising administering to the subject a composition comprising a water-soluble extract of amniotic membrane from frozen or previously frozen placenta, wherein the water-soluble extract comprises tumor necrosis factor-stimulated gene 6 (TSG-6), pentraxin (PTX-3), thrombospondin (TSP-1), and cross-linked high molecular weight hyaluronan (HA).

2. The method of claim 1, wherein the extract further comprises Smad7.

3. The method of claim 1, wherein the composition further comprises a pharmaceutically acceptable diluent, excipient, carrier, or combination thereof.

4. The method of claim 3, wherein the composition is formulated as a non-solid dosage form.

5. The method of claim 3, wherein the composition is formulated as a solution, drops, suspension, aerosol, paste, spray, ointment, oil, emulsion, cream, lotion, gel, a coated bandage, a patch, sticks, balms, shampoo, or combination thereof.

6. The method of claim 3, wherein the composition is formulated for ophthalmic administration, systemic administration, or topical administration.

7. The method of claim 3, wherein the composition is formulated for intraocular injection, subretinal injection, intravitreal injection, periocular injection, subconjuctival injection, retrobulbar injection, intracameral injection, sub-Tenon's injection, implantation, ocular implantation, ocular insertion, insertion between an eye and eyelid, or insertion in a conjunctival sac.

8. The method of claim 3, wherein the composition further comprises a penetration enhancer and an aqueous adjuvant.

9. The method of claim 3, wherein the composition is formulated as a solid dosage form.

10. The method of claim 3, wherein the composition is formulated for controlled release.

11. The method of claim 1, wherein the subject has a surgical scar, a wound scar, a scar from a burn, or a scar from a mechanical injury.

* * * * *